(12) United States Patent
Pesach et al.

(10) Patent No.: US 11,602,418 B2
(45) Date of Patent: Mar. 14, 2023

(54) DEVICE AND METHOD FOR SUBGINGIVAL MEASUREMENT

(71) Applicant: DENTLYTEC G.P.L. LTD., Tel-Aviv (IL)

(72) Inventors: Benny Pesach, Rosh HaAyin (IL); Ygael Grad, Tel-Aviv (IL); Blanc Zach Lehr, Tel-Aviv (IL); Georgy Melamed, Ramat-Gan (IL)

(73) Assignee: DENTLYTEC G.P.L. LTD., Tel-Aviv (IL)

( * ) Notice: Subject to any disclaimer, the term of this patent is extended or adjusted under 35 U.S.C. 154(b) by 374 days.

(21) Appl. No.: 15/274,756

(22) Filed: Sep. 23, 2016

(65) Prior Publication Data
US 2017/0007377 A1 Jan. 12, 2017

Related U.S. Application Data

(63) Continuation of application No. 14/655,286, filed as application No. PCT/IL2013/051059 on Dec. 24, 2013, now Pat. No. 9,454,846.
(Continued)

(51) Int. Cl.
*A61C 9/00* (2006.01)
*A61C 19/04* (2006.01)
(Continued)

(52) U.S. Cl.
CPC ............ *A61C 9/0033* (2013.01); *A61B 1/247* (2013.01); *A61C 9/006* (2013.01); *A61C 9/0053* (2013.01);
(Continued)

(58) Field of Classification Search
CPC ........... A61B 1/24; A61B 1/247; A61C 9/008; A61C 9/0033; A61C 9/0053; A61C 19/043; A61M 25/0122
See application file for complete search history.

(56) References Cited

U.S. PATENT DOCUMENTS 4,279,598 A * 7/1981 Scheicher ............ A61C 8/0043
433/173
4,571,180 A 2/1986 Kulick
(Continued)

FOREIGN PATENT DOCUMENTS

CN 101677757 3/2010
EP 2165674 A1 * 3/2010 ............ A61C 19/043
(Continued)

OTHER PUBLICATIONS

Official Action dated Sep. 28, 2016 for the U.S. Patent and Trademark Office re U.S. Appl. No. 15/115,196 (19 Pages).
(Continued)

*Primary Examiner* — John P Leubecker
(74) *Attorney, Agent, or Firm* — Cooley LLP

(57) ABSTRACT

A method for measuring regions of a tooth in a mouth including: measuring at least one surface point on a surface of the tooth with respect to an element mechanically coupled to said surface point; determining a location of at least one visible reference mechanically coupled to said surface point with respect to said element; estimating a location of said surface point with respect to said visible reference. A device used for such measuring may include a main body comprising a final optical element of an imager which defines an optical field of view directed in a first direction; and a measurement element coupled to said main body extending generally in said first direction; where a tip of said measurement element is sized and shaped to be inserted between a tooth and adjacent gingiva; where said optical field of view is sized to image at least part of a tooth.

38 Claims, 23 Drawing Sheets

Related U.S. Application Data

(60) Provisional application No. 61/745,744, filed on Dec. 24, 2012.

(51) Int. Cl.
*A61B 1/247* (2006.01)
*G06T 17/30* (2006.01)
*H04N 5/225* (2006.01)
*G06T 7/00* (2017.01)
*G06T 15/08* (2011.01)
*A61C 13/00* (2006.01)
*G06T 7/30* (2017.01)
*G06T 7/70* (2017.01)

(52) U.S. Cl.
CPC ........ *A61C 9/0066* (2013.01); *A61C 13/0004* (2013.01); *A61C 19/04* (2013.01); *A61C 19/043* (2013.01); *G06T 7/0014* (2013.01); *G06T 7/30* (2017.01); *G06T 7/70* (2017.01); *G06T 15/08* (2013.01); *G06T 17/30* (2013.01); *H04N 5/225* (2013.01); *G06T 2207/10028* (2013.01); *G06T 2207/30036* (2013.01); *G06T 2215/16* (2013.01); *H04N 2005/2255* (2013.01)

(56) References Cited

U.S. PATENT DOCUMENTS

| | | | |
|---|---|---|---|
| 4,665,621 A | 5/1987 | Ackerman et al. | |
| 4,764,114 A * | 8/1988 | Jeffcoat | A61C 19/043 33/514 |
| 4,790,751 A * | 12/1988 | Reinhardt | A61B 1/247 433/140 |
| 4,883,425 A * | 11/1989 | Zimble | A61C 19/043 433/32 |
| 5,049,070 A * | 9/1991 | Ademovic | A61B 1/0623 433/29 |
| 5,178,536 A * | 1/1993 | Werly | A61B 1/24 348/66 |
| 5,178,537 A * | 1/1993 | Currie | A61C 19/043 433/72 |
| 5,224,049 A | 6/1993 | Mushabac | |
| 5,230,621 A * | 7/1993 | Jacoby | A61B 1/24 433/29 |
| 5,244,387 A * | 9/1993 | Fuierer | A61C 19/043 433/72 |
| 5,257,184 A | 10/1993 | Mushabac | |
| 5,313,053 A | 5/1994 | Koenck et al. | |
| 5,318,442 A * | 6/1994 | Jeffcoat | A61B 9/00 433/27 |
| 5,320,462 A | 6/1994 | Johansson et al. | |
| 5,372,502 A | 12/1994 | Massen et al. | |
| 5,423,677 A * | 6/1995 | Brattesani | A61C 19/043 433/141 |
| 5,435,722 A * | 7/1995 | Mandell | A61C 1/052 433/165 |
| 5,634,790 A * | 6/1997 | Pathmanabhan | A61B 1/00087 433/29 |
| 5,743,731 A * | 4/1998 | Lares | A61B 1/00087 433/29 |
| 5,862,559 A * | 1/1999 | Hunter | A46B 7/08 15/167.1 |
| 5,897,509 A | 4/1999 | Toda et al. | |
| 5,919,129 A | 7/1999 | Vandre | |
| 5,969,321 A | 10/1999 | Danielson et al. | |
| 5,993,209 A * | 11/1999 | Matoba | A61C 19/043 433/72 |
| 6,007,333 A * | 12/1999 | Callan | A61C 3/00 433/143 |
| 6,116,899 A * | 9/2000 | Takeuchi | A61C 19/043 433/29 |
| 6,179,611 B1 * | 1/2001 | Everett | A61B 5/0088 433/29 |
| 6,257,889 B1 * | 7/2001 | Boston | A61C 3/02 433/165 |
| 6,309,219 B1 * | 10/2001 | Robert | A61C 3/00 433/144 |
| 6,468,079 B1 | 10/2002 | Fischer et al. | |
| 6,885,464 B1 | 4/2005 | Pfeiffer et al. | |
| 7,346,417 B2 | 3/2008 | Lüth et al. | |
| 7,494,338 B2 | 2/2009 | Durbin et al. | |
| 7,625,335 B2 | 12/2009 | Deichmann et al. | |
| 7,813,591 B2 | 10/2010 | Paley et al. | |
| 8,439,682 B1 * | 5/2013 | Heath | A61C 5/44 433/224 |
| 8,744,194 B2 | 6/2014 | Kawasaki et al. | |
| 2002/0037490 A1 * | 3/2002 | Oyamada | A61C 3/02 433/165 |
| 2002/0133096 A1 * | 9/2002 | Toda | A61B 5/1076 600/590 |
| 2004/0087937 A1 * | 5/2004 | Eggers et al. | A61B 18/1485 606/41 |
| 2004/0117052 A1 * | 6/2004 | Geng | B82Y 15/00 700/117 |
| 2004/0191725 A1 * | 9/2004 | Szymaitis | A61C 3/02 433/165 |
| 2006/0085005 A1 * | 4/2006 | Kenealy, III | A61C 8/0089 606/80 |
| 2006/0154198 A1 | 7/2006 | Durbin et al. | |
| 2007/0042315 A1 * | 2/2007 | Boutoussov | A61B 1/00163 433/29 |
| 2007/0064242 A1 | 3/2007 | Childers | |
| 2007/0065782 A1 | 3/2007 | Maschke | |
| 2007/0172112 A1 | 7/2007 | Paley et al. | |
| 2007/0260231 A1 * | 11/2007 | Rose | A61B 18/22 606/13 |
| 2008/0002011 A1 | 1/2008 | Mizutani et al. | |
| 2008/0002869 A1 | 1/2008 | Scharlack et al. | |
| 2008/0160477 A1 | 7/2008 | Stookey et al. | |
| 2008/0261165 A1 | 10/2008 | Steingart et al. | |
| 2009/0017416 A1 | 1/2009 | Nguyen et al. | |
| 2009/0061383 A1 * | 3/2009 | Kang | A61C 19/04 433/72 |
| 2009/0087050 A1 | 4/2009 | Gandyra | |
| 2010/0189341 A1 | 7/2010 | Oota et al. | |
| 2010/0238279 A1 * | 9/2010 | Thoms | A61B 1/247 348/77 |
| 2010/0239996 A1 * | 9/2010 | Ertl | A61B 6/145 433/29 |
| 2010/0268069 A1 | 10/2010 | Liang | |
| 2010/0268071 A1 | 10/2010 | Kim | |
| 2010/0305435 A1 | 12/2010 | Magill | |
| 2012/0015329 A1 | 1/2012 | Gross et al. | |
| 2012/0040305 A1 | 2/2012 | Karazivan et al. | |
| 2012/0046536 A1 | 2/2012 | Cheung et al. | |
| 2012/0062557 A1 * | 3/2012 | Dillon | A61C 7/002 345/419 |
| 2012/0097002 A1 | 4/2012 | Thiedig | |
| 2012/0270177 A1 * | 10/2012 | Nakashima | A61C 17/20 433/86 |
| 2012/0271176 A1 | 10/2012 | Moghaddam et al. | |
| 2013/0273492 A1 | 10/2013 | Suttin, Sr. et al. | |
| 2014/0066784 A1 | 3/2014 | Yokota | |
| 2014/0120492 A1 * | 5/2014 | Ioannidis | A61C 19/043 433/27 |
| 2014/0199650 A1 | 7/2014 | Moffson et al. | |
| 2014/0309523 A1 | 10/2014 | Daon et al. | |
| 2014/0343395 A1 | 11/2014 | Choi et al. | |
| 2015/0348320 A1 | 12/2015 | Pesach et al. | |

FOREIGN PATENT DOCUMENTS

| | | |
|---|---|---|
| EP | 2165674 A1 | 3/2010 |
| FR | 2692773 A1 | 12/1993 |
| JP | 63-005742 A | 1/1988 |
| JP | 07-155297 A | 6/1995 |
| JP | 10-165425 A | 6/1998 |
| JP | 10262996 A * | 10/1998 ........... A61C 19/043 |

(56) References Cited

FOREIGN PATENT DOCUMENTS

| JP | H10262996 | 10/1998 | | |
|---|---|---|---|---|
| JP | 11-192207 A | 7/1999 | | |
| JP | 2002-125927 A | 5/2002 | | |
| JP | 2003-325451 | 11/2003 | | |
| JP | 2006-102497 A | 4/2006 | | |
| JP | 2007-152004 | 6/2007 | | |
| JP | 2007-296249 A | 11/2007 | | |
| JP | 2009-268614 | 11/2009 | | |
| JP | 2010-104652 | 5/2010 | | |
| JP | 2012-016573 | 1/2012 | | |
| WO | WO 1998/006352 A1 | 2/1998 | | |
| WO | WO-9806352 A1 * | 2/1998 | ........... | A61C 19/043 |
| WO | WO-2008013181 A1 * | 1/2008 | ............... | A61B 1/24 |
| WO | WO 2014/020247 A1 | 2/2014 | | |
| WO | WO 2014/102779 | 7/2014 | | |
| WO | WO 2015/107520 | 7/2015 | | |
| WO | WO 2016/110855 | 7/2016 | | |
| WO | WO 2016/113745 | 7/2016 | | |
| WO | WO 2016/178212 | 11/2016 | | |
| WO | 2017125926 A2 | 7/2017 | | |

OTHER PUBLICATIONS

Bouguet et al. "3D photography using shadows in dual-space geometry", The International Journal of Computer Vision, 35(2): 129-149, Nov./Dec. 1999.
Notification of Office Action dated Jan. 5, 2017 From the State Intellectual Property Office of the People's Republic of China Re. Application No. 201380071840.0 (7 Pages).
Translation of Notification of Office Action dated Jan. 5, 2017 From the State Intellectual Property Office of the People's Republic of China Re. Application No. 201380071840.0 (4 Pages).
Notice of Reasons for Rejection dated Feb. 14, 2017 From the Japan Patent Office Re. Application No. 2015-548888 and Its Translation Into English. (10 Pages).
Notice of Reasons for Rejection dated Sep. 25, 2018 From the Japan Patent Office Re. Application No. 2017-228103 and Its Translation Into English. (15 Pages).
Flügge, et al., "Precision of Intraoral Digital Dental Impressions with iTero and Extraoral Digitization With the iTero and A Model Scanner," American Journal of Orthodontics and Dentofacial Orthopedics, 144(3); 471-478; Sep. 2013.
Logozzo et al., "Recent Advances in Dental Optics—Part I: 3D Intraoral Scanners for Restorative Dentistry", Optics and Lasers in Engineering, 54: 203-221, Mar. 2014.
Salvi, et al., "Pattern Codification Strategies in Structured Light Systems", Pattern Recognition, 37(4): 827-849, 2004.
Savarese et al., "3D Reconstruction by Shadow Carving: Theory and Practical Evaluation", International Journal of Computer Vision, 71(3): 305-336, published online, Jun. 2006.
Maintz et al., "A Survey of Medical Image Registration," Medical Image Analysis, 2(1): 1-36, Mar. 1998.
Medeiros, et al., "Coded Structured Light for 3D-Photography: An Overview", IEEE-RITA, (Latin-American Learning Technologies Journal), IV(2): 109-124, Jul. 1999.
Geng, "Structured-Light 3D Surface Imaging: A Tutorial", Advances in Optics and Photonics, 3:128-160, 2011.
Communication Relating to the Results of the Partial International Search dated May 8, 2014 from the International Searching Authority re: Application No. PCT/IL2013/051059.
International Search Report and Written Opinion dated Sep. 2, 2014 from the International Searching Authority re: Application No. PCT/IL2013/051059.
International Preliminary Report on Patentability dated Jul. 9, 2015 from the International Bureau of WIPO re: Application No. PCT/IL2013/051059.
International Search Report and Written Opinion dated Apr. 18, 2016 from the International Searching Authority re: Application No. PCT/IL2016/050058.
International Search Report and Written Opinion dated Apr. 21, 2016 from the International Searching Authority re: Application No. PCT/IL2016/050023.
OmniVision "OVM6946 400×400. Compact, Cost-Effective Wafer-Level Camera Module for Single-Use Endoscopes", OmniVision, Product Brief, 2 P., Aug. 10, 2016.
Toshiba "IK-CT2: 0.7×0.7 mm, 220×220, CMOS", Toshiba Information Systems, Product Sheet, 1 P., Dec. 2016.
International Search Report and the Written Opinion dated Aug. 23, 2016 From the International Searching Authority Re. Application No. PCT/IL2016/050449.
Notification of Office Action dated Apr. 15, 2016 From the State Intellectual Property Office of the People's Republic of China Re. Application No. 201380071840.0.
Translation of Notification dated Apr. 15, 2016 From the State Intellectual Property Office of the People's Republic of China Re. Application No. 201380071840.0.
International Preliminary Report on Patentability dated Nov. 16, 2017 From the International Bureau of WIPO Re. Application No. PCT/IL2016/050449. (11 Pages).
Grounds of Reasons of Rejection dated Apr. 26, 2019 From the Korean Intellectual Property Office Re. Application No. 10-2015-7020305. (4 Pages).
Translation Dated May 9, 2019 of Notice Requesting Submission of Opinion dated Apr. 26, 2019 From the Korean Intellectual Property Office Re. Application No. 10-2015-7020305. (4 Pages).
Communication Pursuant to Article 94(3) EPC dated Nov. 19, 2018 From the European Patent Office Re. Application No. 13830124.7. (8 Pages).
Notice of Reasons for Rejection dated May 7, 2019 From the Japan Patent Office Re. Application No. 2017-228103 and Its Translation Into English. (8 Pages).
Communication Relating to the Results of the Partial International Search and the Provisional Opinion dated Jun. 14, 2017 From the International Searching Authority Re. Application No. PCT/IL2017/050072. (12 Pages).
Notice of Reasons for Rejection dated Jul. 11, 2017 From the Japan Patent Office Re. Application No. 2015-548888 and Its Translation Into English. (5 Pages).
International Preliminary Report on Patentability dated Jul. 20, 2017 From the International Bureau of WIPO Re. Application No. PCT/IL2016/050023. (10 Pages).
International Preliminary Report on Patentability dated Jul. 27, 2017 From the International Bureau of WIPO Re. Application No. PCT/IL2016/050058. (7 Pages).
Applicant-Initiated Interview Summary dated Aug. 2, 2017 From the US Patent and Trademark Office Re. U.S. Appl. No. 15/115,196. (3 pages).
Communication Pursuant to Article 94(3) EPC dated Aug. 10, 2017 From the European Patent Office Re. Application No. 13830124.7 (6 Pages).
Requisition by the Examiner dated Oct. 4, 2019 From the Innovation, Science and Economic Development Canada, Canadian Intellectual Property Office Re. Application No. 2,896,210. (3 Pages).
Decision of Rejection dated Jan. 14, 2020 From the Japan Patent Office Re. Application No. 2017-228103 and Its Translation Into English. (7 Pages).
Requisition by the Examiner dated Apr. 7, 2021 From the Innovation, Science and Economic Development Canada, Canadian Intellectual Property Office Re. Application No. 2,896,210. (16 Pages).
Communication Pursuant to Article 94(3) EPC dated Nov. 19, 2020 From the European Patent Office Re. Application No. 13830124.7. (6 Pages).
Summons to Attend Oral Proceedings Pursuant to Rule 115(1) EPC Dated Mar. 19, 2020 From the European Patent Office Re. Application No. 13830124.7. (13 Pages).

* cited by examiner

DEVICE AND METHOD FOR SUBGINGIVAL MEASUREMENT

RELATED APPLICATIONS

This application is a continuation of U.S. patent application Ser. No. 14/655,286 filed Jun. 24, 2015, now U.S. Pat. No. 9,454,846 which is a National Phase of PCT Patent Application No. PCT/IL2013/051059 having International filing date of Dec. 24, 2013, which claims the benefit of priority under 35 USC § 119(e) of U.S. Provisional Patent Application No. 61/745,744 filed on Dec. 24, 2012. The contents of the above applications are all incorporated by reference as if fully set forth herein in their entirety.

FIELD AND BACKGROUND OF THE INVENTION

The present invention, in some embodiments thereof, relates to dental measurements, and more particularly, but not exclusively, to a device and method for subgingival measurement.

Dental treatments often involve measurement of the patient's mouth. In particular, construction of crowns, bridges and other dental prosthetics generally involves measurement or acquisition of three dimensional model/s of existing dental structures. Often prosthetics extend below the gum line, and measurement of dental structures below the gum line is carried out. Accurate measurement/s and/or modeling can facilitate a good fit of the prosthetic constructed using the measurements/s and/or model/s to the patient's mouth.

Dental impressions are a traditional technique for providing a model of the mouth. Generally, a cast is produced from the impression and the cast then is used to produce the prosthetic. Such techniques suffer from inaccuracy due to multiple manual steps which can be technically demanding on the dentist as well as invasive and uncomfortable for the patient, especially if subgingival measurement is necessary.

More recently, digital scanning techniques have offered increased accuracy and detail of measurement. However, such techniques are only able to image, measure and model visible parts of the patient's mouth and generally do not provide imaging of subgingival areas. CT scanning can provide measurement of subgingival areas, however it does not provide soft tissue measurement.

Both existing physical impression methods and digital impression methods of measurement of subgingival areas usually include the step of physically separating the gingiva from the circumference of the tooth (or teeth) to be measured for the time that measurements are taken. This separation usually causes bleeding which needs to be stemmed or prevented before measurements can be made. The process of separation sometimes causes trauma to the gingiva, which can lead to inflammation and permanent damage to the gingiva.

One common technique for separating gingiva from the teeth for subgingival measurements is cord packing, where cord/s are inserted between the tooth/teeth and gingiva, holding the gingiva away from the tooth surface. Cord packing is generally a time consuming procedure, stressful and technically demanding for the dental practitioner and painful for the patient.

Dental practitioners may have a dilemma, either to use damaging, painful, technically challenging methods to expose subgingival tooth areas (e.g., cord packing) for measurement or to forgo subgingival measurements resulting in either ill-fitting prosthetics or prosthetics with unpleasing aesthetics where the border between the prosthetic and original tooth structure is visible above the gum line.

Additional background art includes U.S. Pat. Nos. 7,346,417, 5,257,184, 5,320,462, 7,625,335, U.S. Patent Application Publication No. US2008261165, U.S. Pat. No. 7,813,591, FR2692773, U.S. Pat. Nos. 5,224.049, 5,372,502, 7,494,338.

SUMMARY OF THE INVENTION

There is provided in accordance with an exemplary embodiment of the invention, a method for measuring regions of a tooth in a mouth comprising: measuring at least one surface point on a surface of the tooth with respect to an element mechanically coupled to said surface point;
determining a location of at least one visible reference mechanically coupled to said surface point with respect to said element;
estimating a location of said surface point with respect to said visible reference.

In an exemplary embodiment of the invention, measuring comprises measuring at least one surface point on a subgingival surface of the tooth. Optionally or alternatively, determining comprises:
capturing at least one image of said visible reference using an imager; and determining said location of said visible reference uses said at least one image. Optionally, the method comprises calibrating said imager using a known dimension of said visual reference. Optionally or alternatively, said measuring comprises measuring using a stylus, a tip of which contacts said location. Optionally, the method comprises detecting a contact of said tip with said location. Optionally or alternatively, measuring comprises measuring while scanning said tip along a surface of said tooth. Optionally, scanning comprises:
vibrating said stylus in a generally coronal-apical direction whilst keeping in contact with a tooth surface.

In an exemplary embodiment of the invention according to any of the previous embodiments, said determining comprises detecting a non-axial deflection of said stylus. Optionally or alternatively, said determining comprises determining a stylus tip location. Optionally, said determining a stylus tip location comprises analyzing an image smear in said image.

In an exemplary embodiment of the invention according to any of the previous embodiments, said element is part of a probe body including an imager final optical element; and measuring is measuring with respect to said body.

In an exemplary embodiment of the invention according to any of the previous embodiments, said element comprises a stylus or part thereof; and measuring is measuring with respect to said stylus.

In an exemplary embodiment of the invention according to any of the previous embodiments, said visible reference comprises a visible tooth portion.

In an exemplary embodiment of the invention according to any of the previous embodiments, said visible reference comprises at least one marker.

In an exemplary embodiment of the invention according to any of the previous embodiments, said visible reference comprises a stylus or a portion thereof.

In an exemplary embodiment of the invention according to any of the previous embodiments, generating a measurement tooth model using said estimated location. Optionally, generating comprises:

registering said visible reference with an existing tooth model;

extending said existing tooth model with said location of said surface point to create said measurement tooth model. Optionally, said registering comprises registering an image acquired for said determining to said model. Optionally or alternatively, said registering comprises registering using a marker on the tooth. Optionally or alternatively, said registering comprises generating a 3D model and registering said 3D model to said existing tooth model. Optionally, said generating a 3D model comprises generating a point cloud and registering said point cloud to said existing tooth model.

In an exemplary embodiment of the invention according to any of the previous embodiments, said determining uses an imager and wherein said generating comprises generating a tooth model using images acquired with said imager.

In an exemplary embodiment of the invention according to any of the previous embodiments, the method comprises generating a tooth model from said estimating and combining said generated tooth model with a different tooth model.

In an exemplary embodiment of the invention according to any of the previous embodiments, the method comprises repeating said measuring, determining and estimating for a plurality of locations of surface points. Optionally, the method comprises generating a sub-gingival model from said plurality of estimated locations. Optionally or alternatively, the method comprises illuminating said tooth during said determining.

In an exemplary embodiment of the invention according to any of the previous embodiments, the method comprises also estimating at least one location not on said tooth.

In an exemplary embodiment of the invention according to any of the previous embodiments, the method comprises associating, by a computer, a type information with said location, responsive to one or both of user indication or prompt by a computer system prior to said measuring.

There is provided in accordance with an exemplary embodiment of the invention, a device for measuring regions of a tooth comprising:
a main body comprising a final optical element of an imager which defines an optical field of view directed in a first direction; and
an elongate measurement element coupled to said main body and extending generally in said first direction;
wherein a tip of said measurement element is sized and shaped to be inserted between a tooth and adjacent gingiva;
wherein said a distance between said tip and said body is small enough so that said device can fit inside an adult human mouth and
wherein said optical field of view is sized to image at least part a tooth when such tooth is contacted by said tip.

In an exemplary embodiment of the invention, said tip is formed of or covered with a material softer than tooth dentin. Optionally or alternatively, said elongate measurement element is in the form of a stylus. Optionally or alternatively, said stylus is flexible. Optionally or alternatively, the device comprises at least one sensor which senses contact of said tip with said tooth. Optionally or alternatively, the device comprises at least one sensor which detects a deflection of said elongate element. Optionally or alternatively, the device comprises at least one sensor which detects a movement of said tip.

In an exemplary embodiment of the invention, said sensor is located at a coupling between said measuring element and said body. Optionally or alternatively, said sensor is located at or adjacent said tip.

In an exemplary embodiment of the invention, the device comprises an actuator which moves said tip in a scanning pattern. Optionally, said scanning pattern comprises a vertical scanning.

In an exemplary embodiment of the invention according to any of the previous embodiments, said optical field of view comprises at least two overlapping fields of view.

In an exemplary embodiment of the invention according to any of the previous embodiments, the device comprises said imager.

In an exemplary embodiment of the invention according to any of the previous embodiments, said final optical element comprises a mirror.

In an exemplary embodiment of the invention according to any of the previous embodiments, said elongate measurement element comprises at least one marking or light source positioned in said field of view.

In an exemplary embodiment of the invention according to any of the previous embodiments, the device comprises at least one illumination element which illuminates said tooth and said measurement element.

In an exemplary embodiment of the invention according to any of the previous embodiments, the device comprises a cover on which said elongate measurement element is mounted.

In an exemplary embodiment of the invention according to any of the previous embodiments, said tip is thicker than a thickness of said elongate measurement element adjacent said tip.

In an exemplary embodiment of the invention according to any of the previous embodiments, said tip is rounded.

In an exemplary embodiment of the invention according to any of the previous embodiments, the device comprises circuitry for estimating a location of said tip based on an image acquired via said imager.

In an exemplary embodiment of the invention, said circuitry estimates a movement of said tip relative to said body based on an image acquired via said imager. Optionally or alternatively, the device comprises circuitry for generating a surface of said tooth, including at least one sub-gingival surface portion using said estimated location. Optionally or alternatively, the device comprises circuitry for interpreting a contacting of said tip as an input to mark a tooth model with additional information.

There is provided in accordance with an exemplary embodiment of the invention, a device comprising a connector and an extending elongate measurement element with a tip adapted to be placed between a gingiva and a tooth, said device sized to fit in a human mouth, the connector having an inner geometry configured to mount on an intra-oral scanner. Optionally, said connector comprises a cover with a sealed window for said imager.

There is provided in accordance with an exemplary embodiment of the invention, an attachment sized for intraoral use and configured for rigid attachment to a handheld probe, comprising a mirror and an elongate measurement element, wherein said mirror defines an optical field of view directed in a first direction and wherein said elongate measurement element extends into said field of view and has a tip adapted to be placed between a gingiva and a tooth.

There is provided in accordance with an exemplary embodiment of the invention, a system comprising:
an imager;
an elongate measurement element with a tip adapted to be placed between a gingiva and a tooth; and circuitry configured to analyze an image acquired by said imager and reconstruct a location of said tip when said tip is invisible between said gingiva and said tooth.

There is provided in accordance with an exemplary embodiment of the invention, an intraoral scanner sized for intraoral use for scanning a tooth, comprising:

at least one light source;
at least one imager; and
circuitry configured to reconstruct a shape of a tooth from images acquired by said imager using light from said light source, wherein said circuitry is operative to recognize a tool used to retract a gingiva as not being part of said tooth. In an exemplary embodiment of the invention, said circuitry identifies said tool based on its moving between different images. Optionally or alternatively, said circuitry identifies image portion near a tip of said tool as portions to be considered when building a sub-gingival portion of said reconstruction.

There is provided in accordance with an exemplary embodiment of the invention, a method of intra-oral scanning of at least one tooth, comprising:

identifying, during scanning, the retraction of a gingiva by a tool; and
reconstructing a model of a tooth while not incorporating an image of said tool into the model and incorporated a portion of said tooth exposed by said retraction.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. In some cases elements in corresponding figures have corresponding numbers, which are not necessarily explicitly described.

In the drawings.

DESCRIPTION OF SPECIFIC EMBODIMENTS OF THE INVENTION

Figure 1A:
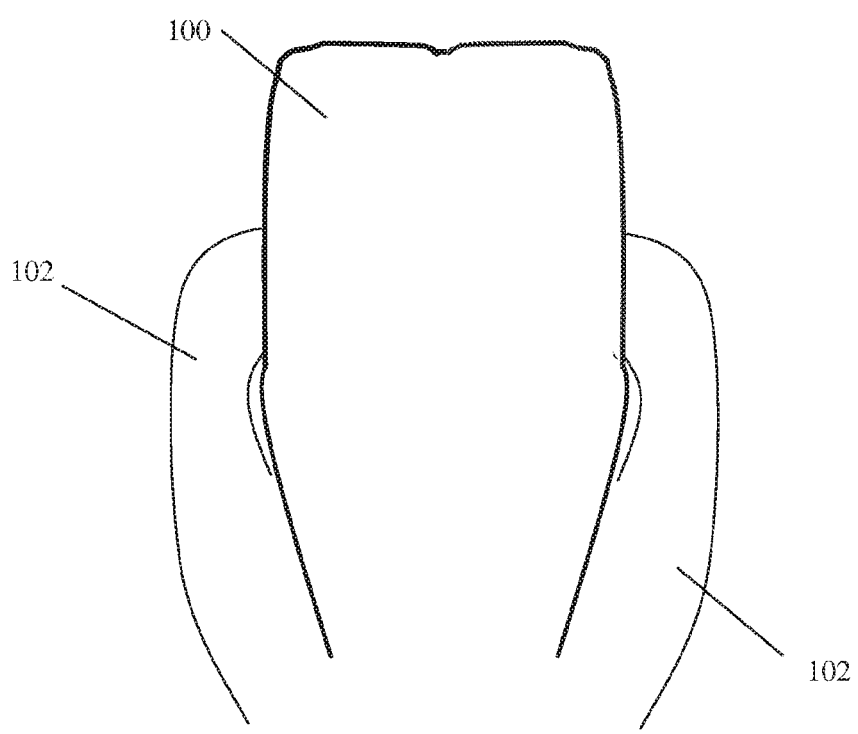
FIG. 1A is a is schematic drawing of an original tooth.

The present invention, in some embodiments thereof, relates to dental measurements, and more particularly, but not exclusively, to a device and method for subgingival measurement.

Overview

An aspect of some embodiments of the invention relates to measuring regions of a tooth, especially subgingival portions, for example, using contact measurement. In some embodiments a stylus tip is put into contact with a subgingival surface of a tooth. The subgingival surface of the tooth is then measured by estimating a location of the stylus tip with respect to a visible reference of a visible portion of the tooth (e.g., tooth portion surface topography, marker on the tooth, stylus) giving a stylus tip location. In some embodiments measurement is using images/s collected by an imager. In some embodiments the stylus is attached to the imager. In some embodiments the imager and the stylus are separate components.

The term 'stylus', as used in this document, refers to any elongated measurement element (EMD) with an elongated measurement element tip (stylus tip) sized and shaped to be inserted between a tooth and adjacent gingiva. In some embodiments a body of the elongated measurement element (stylus) is relatively uniform. In some embodiments the body of the elongated measurement device (stylus) is non-uniform in shape and/or dimension, e.g., conical, forked. In some embodiments the elongated measurement device includes a neck adjacent to the EMD tip which is of different dimension and/or shape than the EMD tip and/or EMD body e.g., the EMD neck is narrower than the EMD tip and EMD body.

In some embodiments, multiple measurements of different subgingival surfaces are combined to generate a surface topography model of at least a subgingival area of the tooth.

In some embodiments, measuring includes repeating measurement for different subgingival surfaces: In some embodiments the stylus tip is put into contact with a subgingival surface of a tooth and the stylus tip location is estimated, the stylus tip is then put into contact with a different surface of a tooth and the a stylus tip location is estimated again. In some embodiments, repeating measurement for different subgingival surfaces is manual, where the user places the stylus tip into contact with different subgingival surfaces or moves (scans) the stylus tip along the tooth surface. In some embodiments, measurement for different subgingival surfaces (e.g., stylus scanning) is automatic, for example where one or more actuators move the stylus and/or a main body to which the stylus in some embodiments is attached (in some embodiments, main body includes the imager). In some embodiments, the stylus moves, for example, vibrates, automatically performs vertical (coronal-apical) movements and the user manually moves the stylus around the tooth. In some embodiments, the stylus automatically performs complex movements e.g., horizontal vibration, combined vertical and horizontal movements, combined vertical movements and/or movements perpendicular to tooth surface.

In some embodiments stylus location and/or stylus tip location e.g., is measured. In some embodiments, stylus tip location is measured/by mechanical measurements, for example stylus deflection, stylus e.g., applied force magnitude and/or direction for example using one or more force sensor (e.g., load cell, strain gauge) In some embodiments one or more force sensor is located at a stylus connection to the main body and/or along a stylus length and/or at the stylus tip.

In some embodiments, stylus and/or stylus tip location is measured optically, for example by measuring a location of one or more stylus marking.

In some embodiments, stylus and/or stylus tip location is measured/tracked magnetically and/or using linear encoder/s and/or using proximity sensor/s.

In some embodiments, stylus location and/or stylus tip location is measured repetitively during stylus movement (e.g., during stylus scanning). In some embodiments a stylus movement is measured. Repetitive stylus location and/or stylus tip measurements and measuring a stylus and/or stylus tip movement are referred to by the term 'tracking'. In some embodiments optical tracking of the stylus and/or one or more stylus marking is by measuring an image smear.

In some embodiments, two or more stylus measurements are combined to generate a measured tooth model. In some embodiments, one or more stylus measurement is combined with a supragingival tooth model measured separately (e.g., from digital imaging, CT scan, MRI scan, 3D intraoral scanner, 3D scan of convention impression). In some embodiments one or more stylus measurement is combined with a supragingival tooth model extending the model. In some embodiments, a subgingival tooth model is combined with a supragingival tooth model.

In some embodiments, combining a two or more tooth measurements is by aligning of two or more images. In some embodiments aligning two or more images is by matching of 3D image information. In some embodiments aligning two or more images is by pattern matching of 2D features and/or natural marks on a tooth surface. In some embodiments aligning two or more images is by matching one or more marker placed on a portion of the mouth being measured (e.g. placed on a coronal portion of the prepared tooth).

In some embodiments, two or more tooth models (e.g., a model generated from stylus measurements and a model generated by another measurement device e.g. CT, MRI, optical scanner) are combined. In some embodiments combining two or more models is by matching of 3D topography information. In some embodiments combining two or more models is by pattern matching of 2D features and/or natural marks on a tooth surface. In some embodiments combining two or more models is by matching one or more marker placed on a portion of the mouth being measured (e.g. placed on a coronal portion of the prepared tooth).

In some embodiments, a tip of the stylus (stylus tip) is thin enough (e.g., a stylus thickness is less than 1 mm) to be easily inserted between a tooth surface and gingiva causing a reduced level of damage to the gingiva than the damage caused to the gingiva by cord packing or retraction paste, for example half the level of damage. In some embodiments, the stylus has varying cross-sectional area along the stylus length for example, for example so that the stylus preferentially bends at one or more point, so that the stylus is more rigid at one or more point.

In some embodiments, a vertical dimension of stylus and main body can be held inside a human adult mouth.

In some embodiments, one or more imaging parameters are selected and/or set for imaging mouth structures and the stylus when the stylus is in position in contact with a tooth to be measured. In some embodiments, one or more imaging parameters are selected to provide clear enough images from which measurements (e.g. 3D topography and/or marker or tooth feature location, stylus location) are determined, for example resolution, modulation transfer function (MTF), imaging wavelength/s. In some embodiments, parameters are selected so that at least a region adjacent to the stylus tip is imaged, for example field of view (FOV), depth of field (DOF), focal length. In some embodiments, one or more imaging parameter are selected at manufacture of the device. In some embodiments, one or more imaging parameter are selected during calibration after manufacture or before collecting measurements. In some embodiments, one or more imaging parameter are selected during measurements (e.g. focus, FOV, DOF, focal length).

In some embodiments, an illumination level of the mouth features to be measured and/or of the stylus is selected for measurements, for example, in some embodiments, high illumination levels and/or pulsed illumination for optical tracking of rapid stylus movements.

In some embodiments, patterned light (e.g. a grid) is projected onto one or more mouth structure and mouth structure 3D topography is estimated from images using the imaged patterned light as is known in the art of estimating 3D topography using patterned light.

In some embodiments, contact of the stylus tip to the tooth is verified in order to verify that collected measurements are of the tooth surface. In some embodiments, if contact of the stylus to the tooth portion is not verified, a user is informed (e.g. by alarm and/or message presented on a user interface). In some embodiments, during stylus measurements, contact of the stylus tip to the tooth is verified by a stylus parameter (e.g., stylus parameter is within a range or above or below a threshold) selected from applied force magnitude, applied force direction, stylus deflection, subgingival surface expected depth.

Optionally, the device is part of a system for producing dental prosthetics. The system can include a processing application operative to do one or more of; generate a tooth model from measurements and optional preexisting tooth model and/or generate a prosthetic model and/or to send the prosthetic model to a machine for construction of the prosthetic.

In some embodiments, the imager includes one or more camera. In some embodiments, the imager includes more than one camera to provide depth information. In some embodiments, the imager includes more than one camera for image around and obstruction (e.g., by the stylus). In some embodiments, the imager includes an image sensor (e.g., CMOS sensor, CCD (Charge Coupled Device) sensor). In some embodiments, the imager includes a plenoptic camera. In some embodiments, the imager includes an image sensor with more than one optical aperture e.g., a single CMOS camera with four lenses that produce four images over four quadrants of the CMOS sensor. In some embodiments, additional camera/s provide images of other teeth and/or other mouth areas. Some embodiments include additional camera/s which can optionally have a wide field of view. In some embodiments, additional camera/s provide jaw information for prosthetic design (e.g., neighboring teeth topography and/or opposite jaw tooth/teeth topography with respect to the prepared tooth is in some embodiments, used to guide prosthetic dimensions) and/or improve orientation accuracy of the imager in relation to tooth for image matching.

An aspect of some embodiments of the invention relates to using gingival retraction with existing intraoral scanners. In an exemplary embodiment of the invention, the oral scanner is programmed to identify and ignore or remove the form of a tool used for gingival retraction, form the image. Optionally, the tool includes a marking or color to assist such recognition. Optionally or alternatively, the shape of the tool sir provided to the intraoral scanner. Optionally, the shape of parts of the tooth that are exposed by the retractor are used to build a tooth model, and may comprise a sub-gingival portion thereof. Optionally, these locations are automatically identified based on their color and/or based on them being near the tip of the retraction tool.

Optionally or alternatively, a tool as described herein is used to scan mechanically such sub-gingival regions, while the intra-oral scanner is operating.

In an exemplary embodiment of the invention, the gingival retraction is provided using a stylus or other elongate measurement element which mounts to the intraoral scanner. Optionally, the intraoral scanner is programmed to ignore blockage of some of its field of view by such an element. Optionally, the connection of the element to the intraoral scanner is rigid.

In this and other embodiments, the tip of the measurement element is optionally rounded, for example, to reduce gingival damage. Optionally or alternatively, the tip includes a stop (e.g., a shelf extending away from the element, which stop interferes with over insertion of the tool under the gingiva. Optionally or alternatively, the tip is made flexible enough so that it bends if used to retract the gingiva too strongly. Optionally or alternatively, the stylus body is made flexible enough so that it bends (e.g., enough to slide past tooth) under a relatively low force, for example, at a force selected in the range between 1 and 500 grams, for example, between 1 and 100 grams.

In this and in other embodiments it is noted that circuitry which performs calculations such as image registration and tooth model generation, may be provided at a remote location. For example, raw image and/or sensor, may be sent remotely and a generated model and/or location position sent back. Optionally, a remote server which provides such functionality associates the model and/or data with a particular patient, tooth, intra-oral scanner (e.g., type and/or code and/or stylus code) and/or practitioner.

An aspect of some embodiments of the invention relates to disposable measurement elements. In some embodiments, a sterile cover with an extending elongate measurement element is used and is designed to mount on an existing or a novel intra-oral scanner. In another embodiment a connector rather than a cover is used. In some embodiments, only the stylus is disposable. In another embodiment, the body of the intraoral scanner is disposable, but with respect to imaging elements, these are provided in a probe to which the body is attached, and the body optionally includes an optical element such as a mirror to shape the desired imaging field.

In some embodiments, the imager is a separate component not connected to the stylus. In some embodiments the imager is not connected to the stylus and is an existing intraoral scanner and the stylus, during scanning, for example, moves one or more portion of the gingiva away from the tooth and/or provides a visible reference.

In some embodiments, the user moves the stylus within the patient's mouth and the stylus movement is measured. Optionally, user stylus movements within the mouth can be combined with a tooth model, for example the user can manually move the stylus over a tooth preparation finish line (user-inputted finish line) and the line is combined with a tooth model. Optionally, the user-inputted finish line is displayed on the tooth model to the user through a user interface.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

In this document directions and orientations are given using standard dental directions (e.g., coronal, apical, buccal, lingual) and/or are given with respect to the orientation of the figures (e.g., vertical, horizontal, above, below).

Crowning a Tooth

Figure 1B:
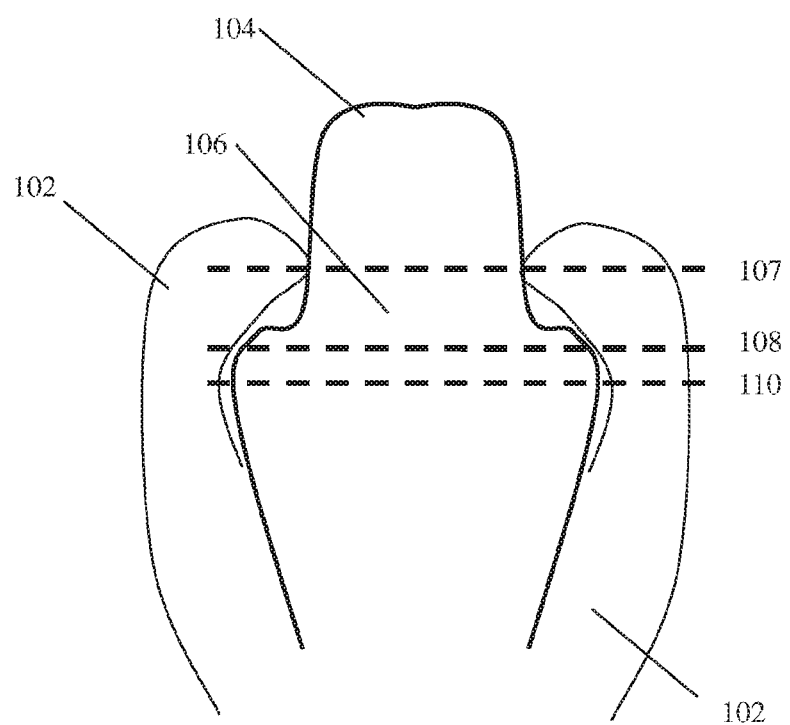
FIG. 1B is a schematic drawing of a prepared tooth.
Figure 1C:
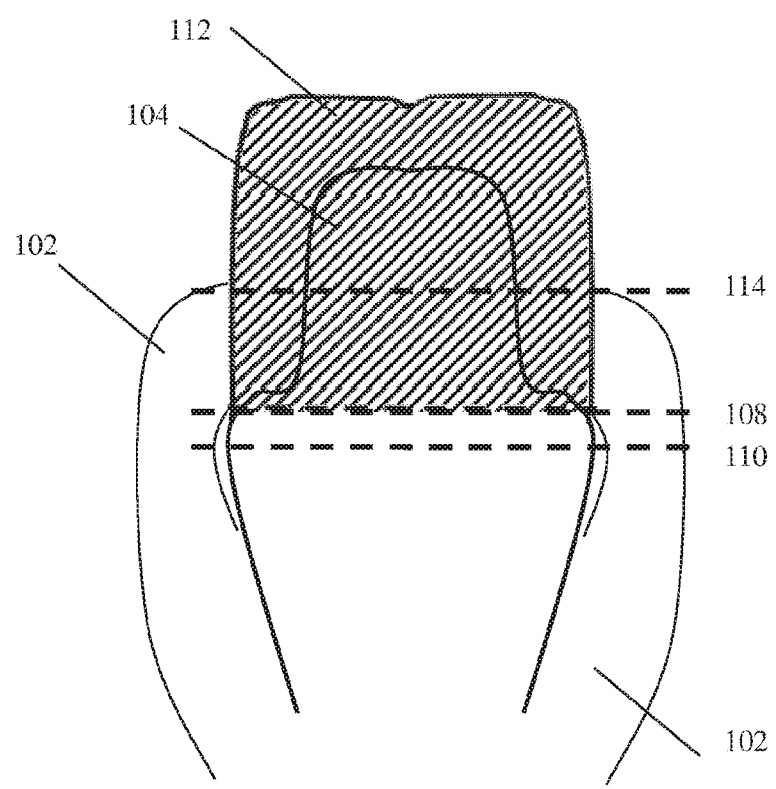
FIG. 1C is a schematic drawing of a crowned tooth.

Referring now to the drawings, FIG. 1A, FIG. 1B and FIG. 1C illustrate the process of crowning a tooth in preparation for using methods and devices in accordance with some embodiments of the invention. FIG. 1A is schematic drawing of an original tooth 100 and surrounding gingiva (or gums) 102. FIG. 1B is a schematic drawing the tooth of FIG. 1A after preparation (e.g., for a crown or a bridge). FIG. 1B shows prepared tooth 104 (also termed tooth peg), gingiva 102, and subgingival preparation area 106. As can be seen, only a supragingival tooth portion the coronal side of (or above) a gum line 107 is visually exposed for digital impression, standard impression or other tooth measurements without performing invasive procedures to reveal the subgingival regions, e.g., cord packing. A preparation finish line 108 delineates the border between a prepared tooth portion in the coronal direction (above) and a natural tooth portion in the apical direction (below) Preparation finish line 108 separates between the natural tooth which includes the tooth enamel coating and the prepared tooth from which the enamel has generally been removed. A subgingival preparation area is the tooth area apical of (below) gum line 107 and coronal of (above) preparation finish line 108 and includes a subgingival preparation margin. Generally, the subgingival preparation margin has a step like shape (the step shape can be rounded). The step like shape is around at least a portion of the tooth where subgingival preparation finish line 108 is the outer edge of the step.

Generally, a well-fitting crown or bridge covers all portions of the tooth which have been shaped or prepared (e.g., by drilling), the tooth portions above or coronal of preparation finish line 108. In some embodiments, for construction of a prosthetic which fits the prepared tooth well, measurements of tooth subgingival area is accurate to about 200μ or about 100 μm or about 40 μm or about 30 μm or about 10 μm or intermediate or better accuracies. A reason for covering all prepared areas of the tooth with the crown is as, during preparation, tooth enamel is often removed leaving any uncovered portions vulnerable to decay.

FIG. 1C is a schematic drawing of a crowned tooth and illustrates a crown 112 which has been affixed (usually glued) over prepared tooth 104. Gingiva 102 meet the crown at a crown gum line 114. Typically, crown 112 restores the general shape of the original tooth. FIG. 1C illustrates a well-fitting crown with a smooth subgingival join/junction between the crown at subgingival preparation finish line 108 which, in this case, is also a finish line of the crown. A smooth surface junction between the prosthetic and the natural tooth is often desirable as any cracks or crevices can provide a hospitable environment for bacteria. Bacteria can cause gum inflammation resulting in tooth decay and/or bone resorption and even tooth loss. Subgingival placement of the preparation finish line and/or the prosthetic finish line is for example, for aesthetic reasons (color difference or visible junction between the natural tooth and a prosthetic) and/or for covering preexisting restorations (e.g. fillings) which extend beneath the gum line.

Generally, it is desirable that an inclination (slope, gradient) of the crown surface at the crown finish line will be the same as the inclination of the natural tooth surface adjacent to the crown finish line in the apical direction to provide a smooth or gentle incline/gradient over the crown finish line. In some embodiments, (e.g., in order to match the crown/prosthetic inclination with the natural tooth inclination) the 3D surface dimensions of the tooth portion above line 110, where line 110 is approximately 0.5 mm-1 mm or approximately 0.1 mm-5 mm beyond (in the apical direction of) subgingival preparation area 108 is measured.

Exemplary Subgingival Measurement Device

Figure 2A:
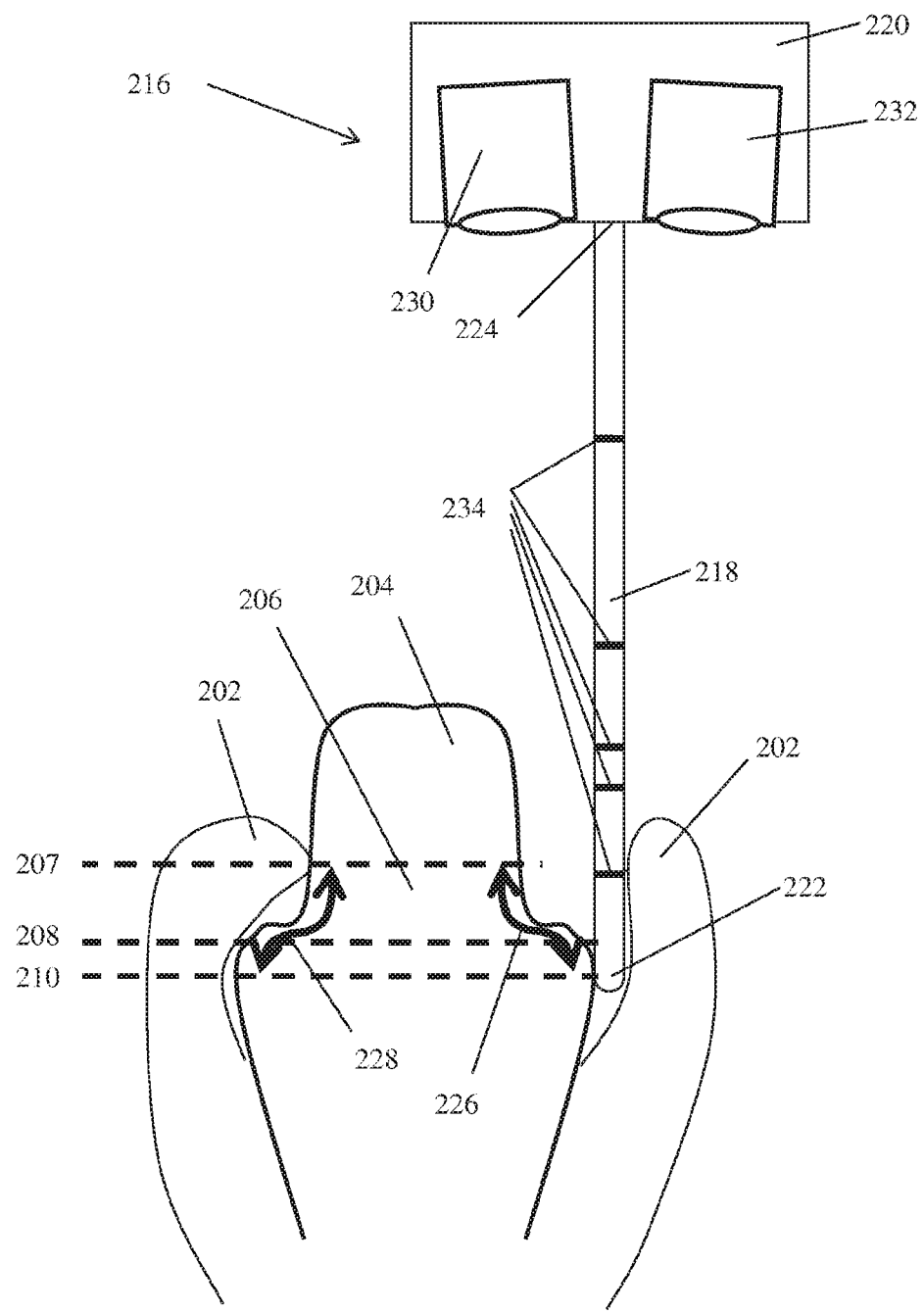
FIG. 2A is a schematic drawing of an embodiment of a device for measuring subgingival tooth portions in accordance with an/some exemplary embodiment/s of the invention.

FIG. 2A is a schematic drawing of a side view of an embodiment of a device for measuring subgingival tooth portions 216 which is also termed a Subgingival Margin Probe (SGMP), in accordance with some exemplary embodiments of the invention. As shown, SGMP 216 includes a stylus 218 (or other elongate measurement element) and a main body 220. In the illustrated embodiment main body 220 optionally houses an imager and the imager optionally includes cameras 230 and 232. In an exemplary embodiment of the invention, the imager has a field of view which can image stylus 218, an area of a tip thereof and/or an area of the tooth against which the stylus is placed. Optionally, the imager is used to capture information about the tooth which can be used to register and/or generate to a tooth model, and/or is used to collect information about the stylus. In FIG. 2A, SGMP 216 is illustrated in position for measuring subgingival tooth portions where a stylus tip 222 at a distal end of stylus 218 has been inserted between gingiva 202 and prepared tooth 204.

In some embodiments, tooth measurement is by inserting stylus 218 in between ginviva 202 and prepared tooth 204. In some embodiments, the imager (e.g. cameras 230 and 232) is used to measure a stylus tip position, for example, directly (stylus tip visible to imager) and/or indirectly (stylus tip invisible to imager). In some embodiments the stylus tip position is estimated from images with respect to a visible tooth portion. In some embodiments the imager includes two cameras 230 and 232 which provide images of the same 3D feature from which depth information is extracted. In some embodiments the images are matched (possibly at a later time) to a model of the tooth, so that the relative position of the stylus tip and the tooth can be ascertained therefrom.

In some embodiments, rigid attachment of stylus to main body and rigid stylus 218 mean that the stylus end location with respect to the main body is known and maintained during scanning. In some embodiments, a stylus proximal side 224 is attached to main body 220. In some embodiments, attachment of stylus proximal side 224 to main body 220 is rigid. In some embodiments, stylus 218 is rigid.

In some embodiments, attachment of stylus proximal side 224 to main body 220 is rigid but stylus 218 is flexible allowing stylus tip 222 to move with respect to main body 220. In some embodiments, attachment of stylus proximal side 224 to main body 220 is flexible allowing stylus 218 to move with respect to main body 220. In an exemplary embodiment of the invention, movement of the stylus is used for one or both of identifying contact of the stylus with a tooth (e.g., if the tooth deflects the stylus) or to allow scanning motion of the stylus and estimation of a tip location based on movement of the stylus relative to body 220.

In some embodiments, as illustrated in FIG. 2A, the imager is located in main body 220. The example schematically shown in FIG. 2A includes two cameras 230 and 232. In some embodiments, the imager (e.g., cameras 230 and 232) captures images of tooth 204 from different directions and may be used to image the 3D contour of tooth 204 and/or optionally the 3D contour of gingiva 202, gum line 207 on tooth. In some embodiments, reconstruction of 3D features (e.g., visible tooth surface) from images uses, for example Moire topography methods (fringe pattern modeling), stereoscopy or other methods known in the art of oral or non-oral 3D scanning or shape reconstruction from images.

Optionally, main body 220 includes one or more illumination elements for example light/s (e.g., LED, standard bulb) and/or pattern projector/s. Optionally, the illumination elements are used for 3D shape reconstruction (e.g., by projecting patterned light). Optionally or alternatively, the element(s) are used for providing light for the imager and/or dentist and/or to illuminate the stylus.

In some embodiments, during measurement with the SGMP, stylus 218 lifts gingival tissue 202 revealing a portion of subgingival area 206, optionally including preparation finish line 208, temporarily to cameras 230, 232. The revealed portion of subgingival area 206 can then be measured using image/s collected by cameras 230, 232 optionally including stylus 218 and/or stylus marking/s 234.

Methods

Figure 2B:
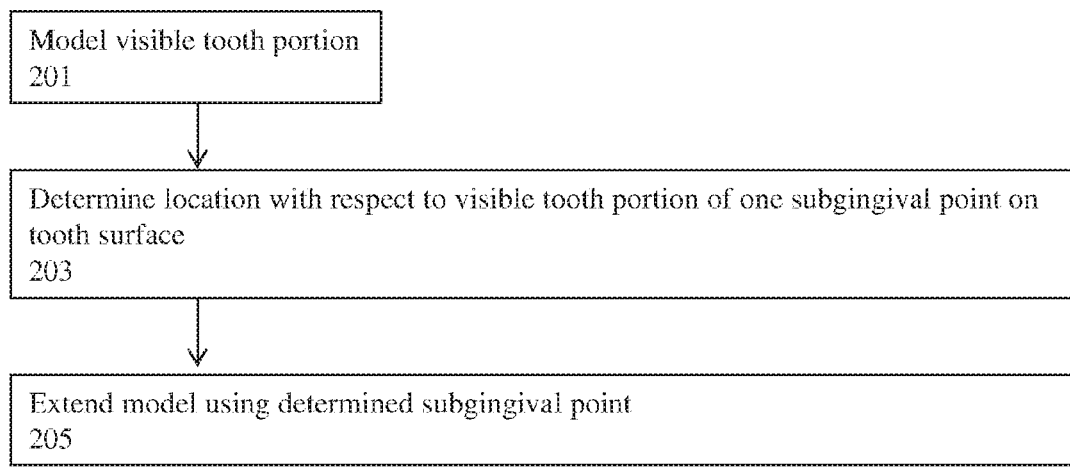
FIG. 2B is a flow chart of a method of extending a tooth model by one subgingival point in accordance with an/some exemplary embodiment/s of the invention.

FIG. 2B is a flow chart of a method of extending a tooth model by one subgingival point in accordance with an/some exemplary embodiment/s of the invention.

At 201, a visible tooth portion is modeled. In some embodiments, modeling of the visible tooth portion is by processing images collected by the imager and/or by scanning the visible tooth portion with the stylus. In some embodiments, modeling of the visible tooth portion uses intraoral digital scanning. In some embodiments, modeling of the visible tooth portion uses standard impression without separation of the gums from the teeth followed by 3D scanning of the impression or impression cast. In some embodiments, modeling of the visible tooth portion is using CT, MRI or X-ray images. At 203, a location of one subgingival point on the surface of the tooth with respect to the visible tooth portion is then determined.

At 205, the model is then extended using the location of the subgingival point. In some embodiments, this method is repeated for multiple subgingival points in order to provide a 3D tooth model including subgingival areas. In some embodiment the 3D tooth model is a surface topography model.

In some embodiments, for example, if the model to be extended is a supra-gingival model (e.g., acquired with the SGMP) and/or is a model built up using locations, the extending may be carried out after the fact. For example, raw images and/or sensor measurements are collected and sent to a processor which then generates a model and/or extends a model and/or combines two models. Optionally, a low quality model may be quickly reconstructed, for example, to support basic Q/A by the dentist.

When extending the model, extending may be of a point or more at a time, or, for example, a model is built up using the points and that model is merged with an existing model (e.g., using smoothing where there is overlap).

Figure 2C:
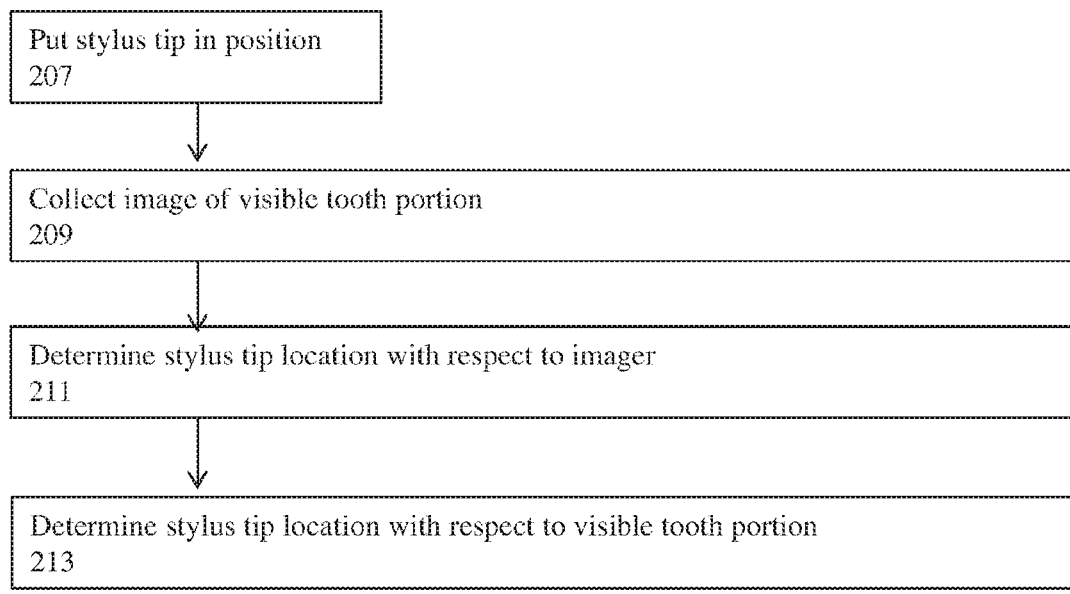
FIG. 2C is a flow chart of a method in accordance with an/some exemplary embodiment/s of the invention.

FIG. 2C shows a method of determining a location of a point on a subgingival tooth surface with respect to a visible tooth portion.

At 207, a stylus is put into position in contact with a point on a subgingival (or non-visible) tooth surface.

At 209, an image of a visible tooth portion is collected. Optionally, the image of the tooth portion provides information as to the tooth portion dimension/location with respect to the imager.

At 211, the stylus tip location with respect to the imager (or other fixed point) is optionally determined. In some embodiments, this is a fixed distance due to the stylus being rigid. In other embodiments, the stylus is moved and/or may move or deflect and sensor measurements which capture this information may be used to correct the determination. In some embodiments, act 211 is not carried out as such, rather the calculation of stylus tip position relative to the tooth may mathematically incorporate this determination without actually performing it explicitly.

At 213, the stylus tip location (and/or location of contacted tooth surface) with respect to the visible tooth portion is optionally determined from the tooth portion dimension/s with respect to the imager and the stylus tip location with respect to the imager.

In some embodiments, marker/s are affixed to the tooth or another mouth structure. In some embodiments, determining a location of a point on a subgingival tooth surface is with respect to such a marker, for example, as follows:

(i) An image of a marker is collected.

(ii) The image and/or other detection of the marker provides information as to the marker location with respect to the imager.

(iii) The stylus tip location with respect to the imager is optionally determined (e.g., 211).

(iv) The stylus tip location with respect to the marker is optionally determined from the marker location with respect to the imager and the stylus tip location with respect to the imager.

In some embodiments, the location of marker/s in relation to the visible tooth portion is known (e.g., by a processing circuitry, for example, based on user entry, contacting a marker with the stylus tip and/or code entry, which code is associated with such information) and the stylus tip location with respect to the visible tooth portion is determined from the stylus tip location relative to the marker/s, for example, using analytical geometry methods.

In general, it is noted that item positions in this and other embodiments may be extracted from images using various methods, including such as known in the field of image processing. Various geometric calculation methods may be used, for example, as known in 3D geometrical processing. Model/image matching and/or reconstruction may use method known in the art of image matching and 3D and/or surface model matching. In some embodiments, the location of marker/s in relation to the visible tooth portion is determined by measuring, using the stylus tip and images, a set of locations on the visible tooth portion, and integrating or matching (e.g., using cloud-of-points matching techniques) the set of measured locations in relation to the visible tooth portion model to find the marker/s location and subgingival point in relation to the visible tooth portion model.

Scanning

In some embodiments, multiple subgingival measurements according to the methods described in this document are made (e.g., as described in FIG. 2B and FIG. 2C). In some embodiments, multiple measurements for different subgingival surfaces are manual, where the user places the stylus tip into contact with different subgingival surfaces or moves the stylus tip along the tooth surface (scans) manually.

In an exemplary embodiment of the invention, by providing multiple measurements a shape of a surface of the tooth can be reconstructed. In an exemplary embodiment of the invention, the surface to be reconstructed is between 10% and 100%, for example, between 20% and 70% of the sub-gingival (and above bone) surface of the tooth, for example, up to 1 mm, 2 mm, 3 mm, 5 mm or intermediate or greater depth below the gum line and/or below a step formed in the tooth for crowning. Optionally, the scanned area is between 10% and 100% (e.g., between 20% and 70%) of the circumference of the tooth. In some cases surfaces of more than one tooth are reconstructed. Optionally or alternatively, scanning also includes supra-gingival parts of the tooth. In some embodiments, scanning is repeated, for example, a dentist modifying the tooth shape after reviewing a model (or other visualization) generated from the tooth data.

Some of the methods described herein provide faster acquisition and/or increased accuracy while measuring, for example, by incorporating substantially continuous measurement of tip location (which may be useful even for manual scanning) and/or data acquisition at a rate faster than image acquisition.

In some embodiments, scanning is where the stylus tip is moved coronal-apically (approximately vertically) whilst remaining in contact with the tooth surface (similar to the scraping movements generally employed by dentists when cleaning plaque from a tooth or when conducting a pocket survey.) as illustrated by arrows 226 and 228 in FIG. 2A. Although referred to in this document as coronal/apical movement, vertical movement, up/down movement, as the stylus remains in contact with the surface of the tooth the movement may also include a non-coronal/apical movement component of the stylus tip. In some embodiments, as described in more detail below, scanning is by coronal/apical movements of the main body, and/or of the stylus proximal end but, due to stylus deflection and/or deformation, the stylus tip performs the coronal/apical whilst remaining in contact with the tooth surface movement as described above. In some embodiments, for the stylus to remain in contact with the tooth, the stylus is contacted to the tooth with a lateral force in the direction of the tooth surface. In some embodiments, lateral force is provided by elasticity of the stylus attachment to the main body, and/or stylus elasticity. In some embodiments, lateral force is provided by application (e.g., by an actuator) of a shift manually or automatically of the stylus and/or main body towards the tooth center.

In some tooth preparations, the prepared tooth includes sharp angles e.g., a step shape at the tooth preparation finish line (the junction between prepared tooth and natural tooth). If the prepared tooth includes a step shape vertical stylus scanning in the coronal-apical direction whilst staying in contact with the tooth surface may be difficult to perform. This may be due to the high angle between the step shape and the natural tooth (e.g., the stylus gets caught by high angles, the stylus looses contact and jumps across high angles).

In some embodiments, difficulties in vertical stylus scanning can be overcome by scanning perpendicular to the tooth surface. In some embodiments, stylus scanning movements, which are automatic in some embodiments, are vertical movements over some tooth surface and movements perpendicular to the tooth surface over some tooth surfaces (e.g. the stylus scans an upper portion of a tooth step shape vertically and a base section of a tooth step shape perpendicular to a tooth surface. In some embodiments, stylus scanning movements, which are automatic in some embodiments are combined vertical movements and movements perpendicular to the tooth surface or along tooth surface (e.g., helical movements in space or circular movements relative to tooth surface).

Figure 2D:
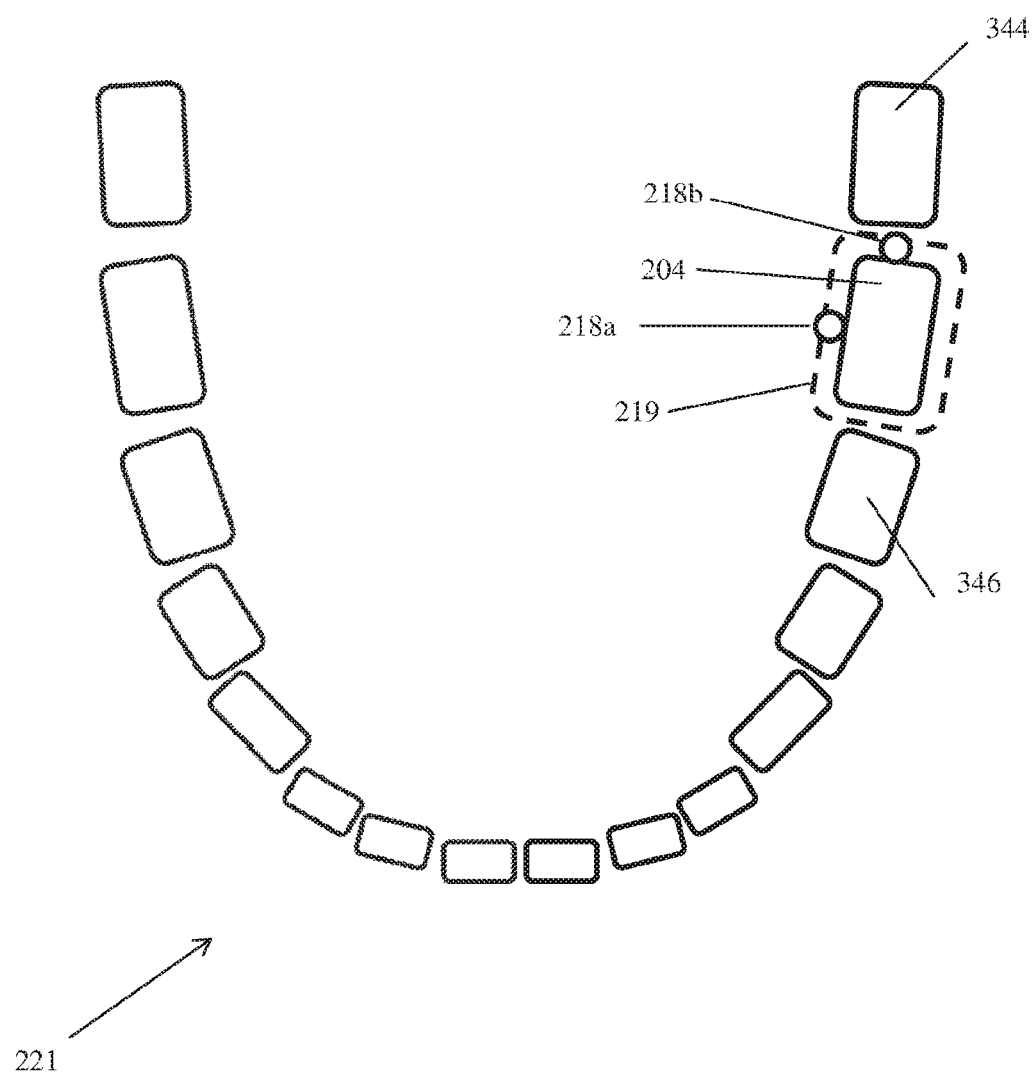
FIG. 2D is a schematic drawing of a stylus path with respect to a top view of teeth in a jaw in accordance with an/some exemplary embodiment/s of the invention.

FIG. 2D is a schematic drawing of a top view of teeth in a jaw. Prepared tooth or tooth peg 204 is shown in context with other teeth in a jaw 221. A stylus first position 218a, a stylus second position 218b and a stylus path 219 show a stylus scanning movement around prepared tooth 204. In some embodiments, scanning movement is clockwise along path 219 around prepared tooth 204. In some embodiment scanning movement is anticlockwise along path 219 around prepared tooth 204. In some embodiments, scanning movement is continuous along path 219 around prepared tooth 204. In some embodiments, scanning movement is non-continuous along path 219 around prepared tooth 204.

In some embodiments, scanning of the subgingival margin is by repetitive stylus movements in one general direction whilst moving the stylus in another general direction. For example, the coronal-apical stylus movement whilst remaining in contact with the tooth surface, as described above, in some embodiments, is combined with stylus movement around stylus path 219 (e.g. the stylus vibrates vertically while it is scanned around the tooth).

In some embodiments, the coronal/apical movement whilst remaining in contact with the tooth surface is achieved by the stylus tip moving with respect to the main body while the stylus movement around path 219 is by both the stylus and the main body. In some embodiments, the stylus moves with respect to the main body for both coronal/apical movements whilst in contact with the tooth surface and stylus movement around path 219. In some embodiments, main body 220 is fixed to the prepared tooth, and/or another tooth, and/or teeth, and/or or the jaw and/or to an external fixture and/or by the patient biting down on one or more portion of the device.

In some embodiments, scanning is by successive stylus movements around the prepared tooth (e.g., around path 219) at different depths (coronal-apical positions) on the tooth.

In some embodiments, stylus scanning of the tooth can be automatic where, for example, motor/s (e.g., actuator/s) move the stylus and/or the stylus body. In some embodiments, the device can scan the tooth partially automatically e.g., where coronal/apical whilst in contact with the tooth surface movements as described above are automatic and the user manually moves the stylus around path 219.

Surrounding mouth structures to prepared tooth 204 include, for example teeth, palate, tongue, cheeks, gingiva. The surrounding mouth structures differ at stylus positions 218*a* and 218*b*: At 218*a* the stylus is not adjacent to other teeth, but is adjacent to the tongue. At 218*b* the stylus is adjacent to adjacent tooth 344. In some positions around path 219 surrounding mouth structures can form obstructions to imaging.

In an exemplary embodiment of the invention, vertical scanning is provided by a coupling between the stylus and the body, which coupling includes a length changing element, such as a linear actuator or a piezoelectric element. Similar structures and/or structures such as described below, may be used to provide stylus movement.

In an exemplary embodiment of the invention, during signal processing of acquired signals, data relating to when the stylus tip is in contact with the tooth is saved, while other data is optionally discarded and/or not used for imager reconstruction.

In an exemplary embodiment of the invention, image acquisition continues during scanning, optionally, the rate of image acquisition and/or timing thereof, being matched to scanning parameters.

While scanning is described herein to collect information to construct a tooth model, in some embodiments, scanning or single contact is used for data entry. In one example, a user can "mark" on a tooth by indicating such to a user interface and then contracting the tooth and or scanning along a portion thereof. Due to the earlier indication, this information may be stored, optionally together with a reconstructed or other tooth model, as (also) indicating something other than a mere surface. One example, is marking of a finishing line. Another example, is a marking of a boundary where sub-gingival scanning is needed.

Exemplary Shape and Dimensions

In some embodiments, a stylus tip thickness is between 0.1 mm and 2 mm or between 0.5 mm and 1.5 mm potentially preventing insertion of stylus 218 from damaging the patient's gingiva, and assisting the user (dentist) in inserting and moving the stylus during measurements. If the stylus tip has a circular cross section the stylus tip thickness is the stylus diameter. If the stylus tip has a non-circular cross section the stylus tip thickness is the smallest distance between two points on the circumference of the cross-section which can be connected by a straight line through a center point of the cross-section. In some embodiments, the stylus tip thickness is smaller than 1 mm. In some embodiments, stylus 218 has a varying thickness along the stylus length between 0.05-7 mm, or between 0.5-3 mm. In some embodiments a varying stylus thickness along the stylus length (e.g., stylus tip has a smaller thickness than the stylus thickness at the stylus attachment to the main body) enables the stylus to deflect without collapsing.

In some embodiments stylus is shaped that the tip is cone shaped with a stylus body having approximately the same diameter as the circular base of the cone shaped tip (e.g., stylus shape is similar to a pencil shape).

A thin stylus (e.g., where the stylus body excluding stylus tip is less than 3 mm in diameter or less than 1 mm diameter) can be flexible, deflecting when force is applied during scanning. In some embodiments, attachment of the stylus to the main body is not fully rigid resulting in mechanical tolerances in the connection of the stylus the main body. In some embodiments, stylus flexibility and mechanical tolerances of stylus-main body connection allow the stylus tip to move 10-100 m relative to the main body during scanning (due to forces applied for stylus insertion and scanning movements). In some embodiments the stylus tip can have larger movements relative to main body for example, the stylus tip moves up to 2 mm with respect to the main body. In some embodiments, as are described in more detail below, a stylus tip location relative to the main body is estimated.

In some embodiment SGMP main body 220 is held by the dentist when scanning the tooth. In some embodiments, a vertical part of SGMP including the stylus and at least a portion of the main body which is connected to the stylus can be put into a patient's mouth e.g., a height 978 illustrated in FIG. 9A. In some embodiments, a height or vertical dimension of SGMP, from the stylus tip to a top of main body (e.g., height 978 illustrated in FIG. 9A) is less than 10 cm or less than 7 cm or less than 5 cm or less than 3 cm. As described previously, in some embodiments, measurements are taken when stylus is inserted in an apical-coronal (vertical) orientation. In some embodiments, a stylus length is less than 8 cm, or less than 5 cm or less than 3 cm, or less than 2 cm. In some embodiments, a final optical element, e.g., camera/s, mirror, is within 8 cm or within 4 cm or within 2 cm of the stylus tip.

Subgingival Device including Four Cameras

In some embodiments, multiple cameras, (e.g., four cameras) collect images of adjacent teeth. For example, in FIG. 3B, adjacent tooth 344, is seen by cameras 332 and 342. In some embodiments, images of adjacent teeth are used to obtain measurement or models which include adjacent teeth. In some embodiments, measurement or models which include adjacent teeth are used to determine the boundaries of a crown, bridge or other prosthetic. In some embodiments, images of adjacent teeth are used in registration of collected images with a tooth model (e.g., tooth model from intraoral scanner, scanning standard impression, CT).

Figure 3A:
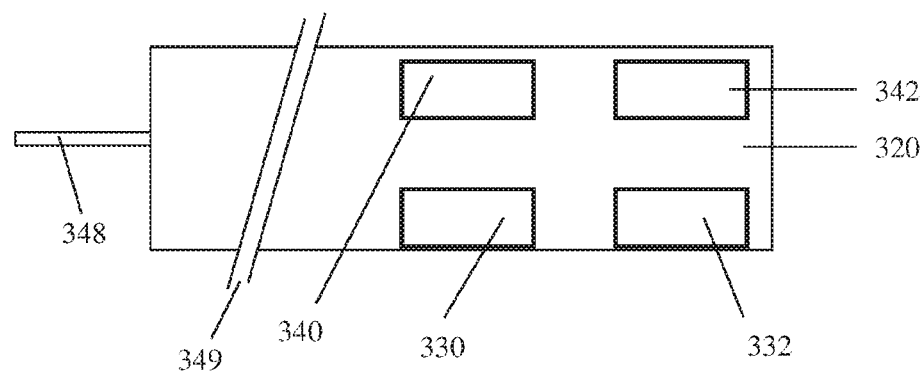
FIG. 3A is a schematic drawing of a top view of an embodiment of a device for measuring subgingival tooth portions with four cameras in accordance with an/some exemplary embodiment/s of the invention.
Figure 3B:
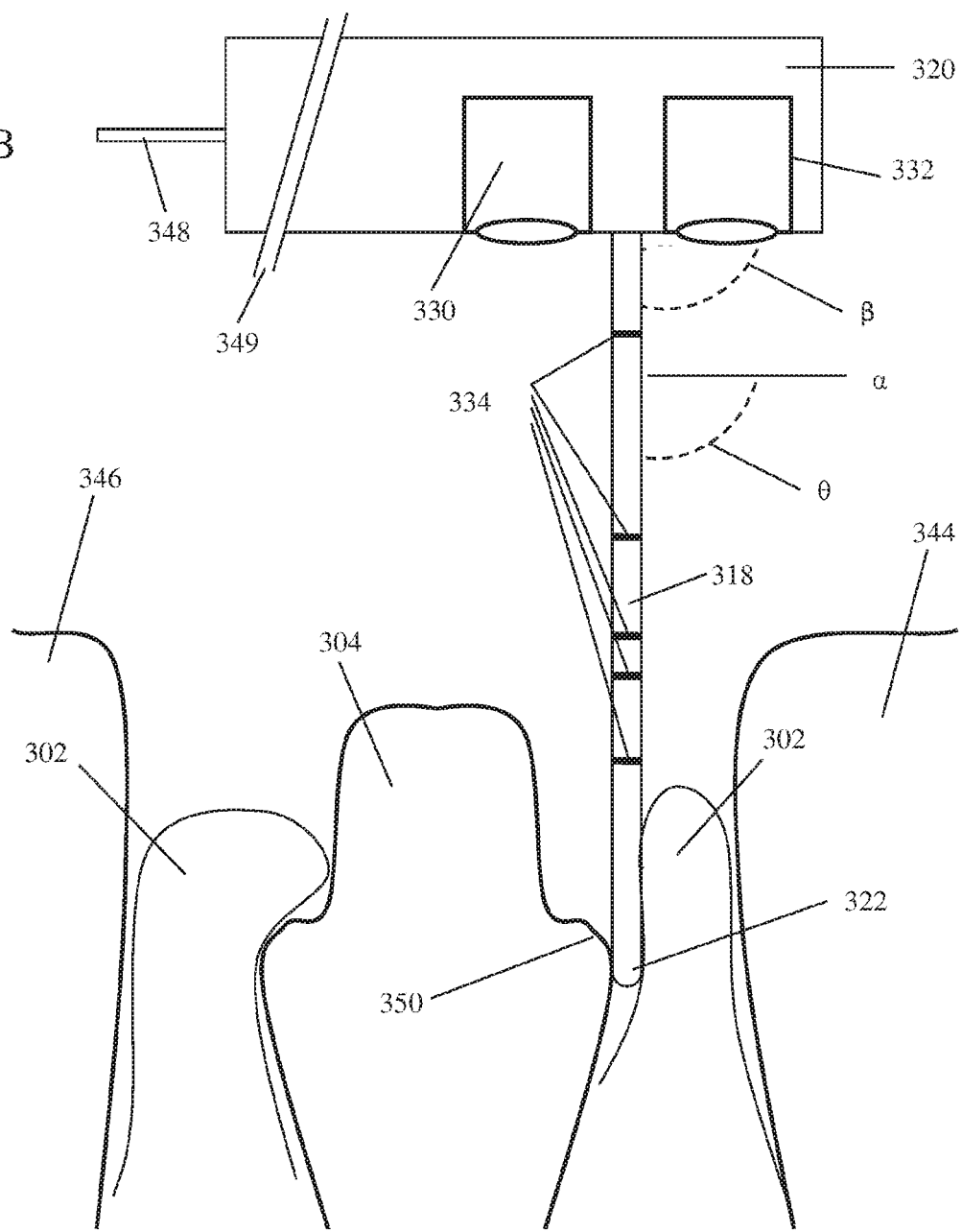
FIG. 3B is a side view of an embodiment of a device for measuring subgingival tooth portions with four cameras in accordance with an/some exemplary embodiment/s of the invention.

Referring now to FIG. 3A and FIG. 3B. FIG. 3A illustrates a top view of an embodiment where a main body 320 includes four cameras 330, 332, 340 and 342. Also visible is a main body cable 348. In some embodiments, main body is elongated and in some embodiments, main body hangs out of the patient's mouth during measurement. An elongated main body is illustrated by break 349.

FIG. 3B illustrates a side view SGMP including the main body of FIG. 3A. Also illustrated in FIG. 3B are stylus 318, stylus markings 334, tooth 304, gingiva 302, adjacent teeth 344 and 346, cable 348, break 349. FIG. 3B illustrates stylus 318 in between prepared tooth 304 and adjacent tooth 344, similar to stylus second position 218*b* illustrated in FIG. 2D.

In some measurement stylus positions (e.g., around path 219 in FIG. 2D) surrounding mouth structures can form obstructions to imaging. Increasing the number of SGMP cameras means that if a camera's view is obstructed, another camera or cameras may have an unobstructed view. For example, at least a portion of the subgingival margin region 350, shown in FIG. 3B, can be seen by two cameras 330 and 340.

In some embodiments, four cameras image stylus 318 and stylus markings 334 and the stylus tip location is estimated at a high accuracy (e.g., accurate to within 10 µm) relative to tooth 304.

FIG. 3A and FIG. 3B also schematically show cable 348 that can connect main body 320 with an external power supply and/or a processing application (e.g., processing application 1280). In some embodiments, (including the embodiment illustrated by FIG. 2A.) SGMP 216 is wireless, with, for example, an internal battery for power supply. In some embodiments, wireless SGMP 216 includes a wireless communication infrastructure e.g., for communication with an external processor or processing application.

In some embodiments, during measurements with the stylus, as illustrated in FIG. 3B, the stylus is orientated in the coronal-apical direction where a tilt angle θ to a distal-mesal direction (horizontal) a is approximately 90°. In some embodiments, the stylus is orientated at approximately 90° to a buccal-lingual direction (not illustrated).

However, in some embodiments, measurements can be collected where the stylus is inserted at a different angle, for example where tilt angle to the distal-mesal direction and/or to the buccal-lingual direction is less than 90°, or less than 45° or less than 20°. In some embodiments, the stylus is tilted for tooth measurement below the preparation finish line or for tooth measurement of tooth surfaces where the angle of the tooth to the apical-coronal direction increases (e.g., the tooth narrows towards the tooth root). Whilst travelling around path 219 the stylus can move through different angles or orientations. For example, in some embodiments, an angle at which the stylus is inserted at first stylus position 218a and an angle at which the stylus is inserted at second stylus position 218b are different. In some embodiments, a gap between the prepared tooth and an adjacent tooth is smaller than the stylus tip diameter and the stylus is inserted for measurement of subgingival surfaces from the side (e.g., from a buccal or lingual direction) at a high tilt angle (e.g., at a tilt angle to the buccal-lingual direction of less than 45°). In some embodiments, an angle of a stylus portion orientation adjacent to main body (as illustrated in FIG. 3B by angle β) with respect to main body is 90°, or angled and between 45° and 90°, or angled below 45°.

Imaging and Cameras

FIG. 4A, FIG. 4B, FIG. 5A, FIG. 5B, FIG. 6A and FIG. 6B are top views of embodiments showing cameras' field of view (FOV) for three exemplary embodiments of the device. Illustrated top views are of a cross section of the cameras FOV above the tooth, (and a stylus cross section) as cameras FOV and overlap varies with depth: In some embodiments cameras three dimensional shape is a truncated cone shape, the truncated tip of the FOV at the camera lens.

Figure 4A:
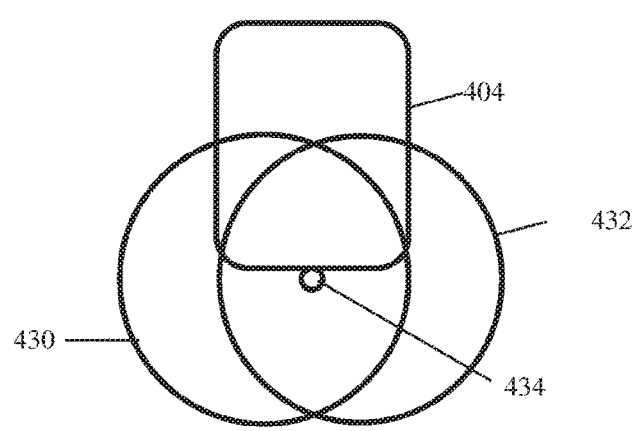
FIG. 4A and FIG. 4B are top views of an embodiment with two cameras measuring a tooth in accordance with an/some exemplary embodiment/s of the invention.
Figure 4B:
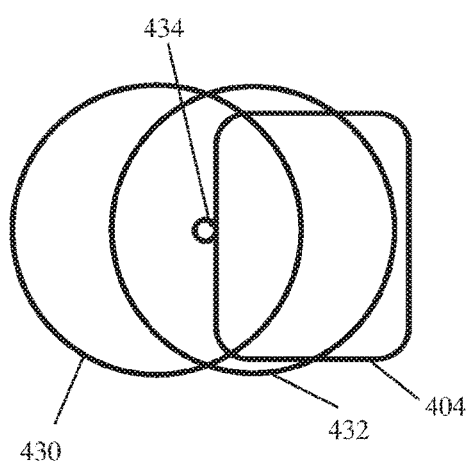

FIG. 4A and FIG. 4B show a top view of a tooth 404 being measured by an embodiment with two cameras. Also illustrated are cameras' FOVs 430, 432 for the two cameras and a stylus 434 (for clarity the main body is not illustrated). In FIG. 4A both cameras view tooth 404 and the stylus. FIG. 4B illustrates the device of FIG. 4A where the device has been moved around the tooth, but without rotating the main body and/or cameras. In FIG. 4B stylus 434 and tooth 404 somewhat obstruct the view of the cameras. In some embodiments, the overlapping FOV of the cameras is set to be at the tooth and stylus.

Figure 5A:
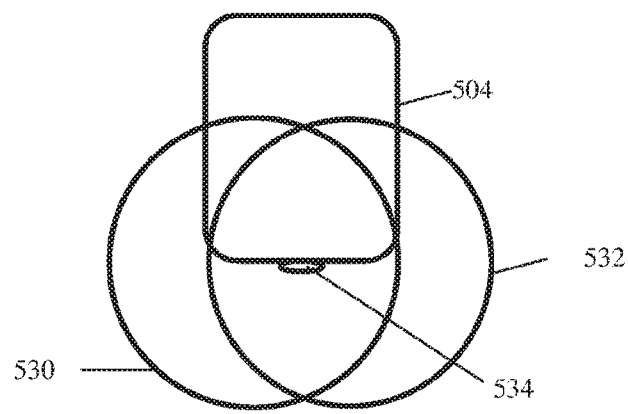
FIG. 5A and FIG. 5B are top views of an embodiment with two cameras and a flattened cross section stylus measuring a tooth in accordance with an/some exemplary embodiment/s of the invention.
Figure 5B:
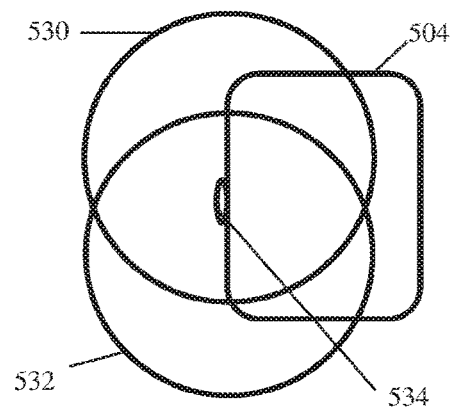

FIG. 5A and FIG. 5B illustrate an embodiment with a stylus which has a flattened cross section. A flattened stylus cross section means that as the stylus is moved around the tooth it tends to rotate: In FIG. 5B the cameras' FOV 530, 532 and stylus 543 have rotated with stylus 534 as stylus 534 has been moved around tooth 504 and FOV 530, 532 of the cameras remains unobstructed. In some embodiments, as illustrated in FIG. 5A and FIG. 5B the cameras rotate as the stylus is moved (or scanned) around the tooth. In some embodiments, the stylus, imager/cameras and main body rotate as the stylus is scanned around the tooth. In some embodiments the imager is rotated (e.g. the camera FOV movement as illustrated in FIG. 5A and FIG. 5B) without rotating other part/s of the main body during stylus scanning around the tooth. A potential advantage of the imager rotating while one or more part of the main body does not rotate is that the main body can have one or more dimension which can not fit into a human mouth, (e.g., cable 348). For example, in some embodiments, the stylus and imager/cameras are mounted to the main body through a rotating head which can be rotated automatically or manually during the stylus scan around the tooth.

Figure 6A:
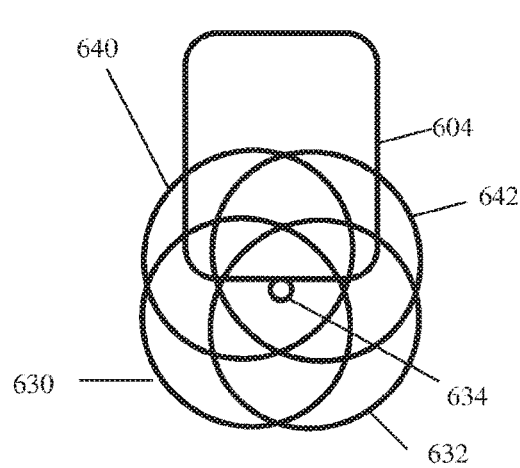
FIG. 6A and FIG. 6B are top views of an embodiment with four cameras measuring a tooth in accordance with an/some exemplary embodiment/s of the invention.
Figure 6B:
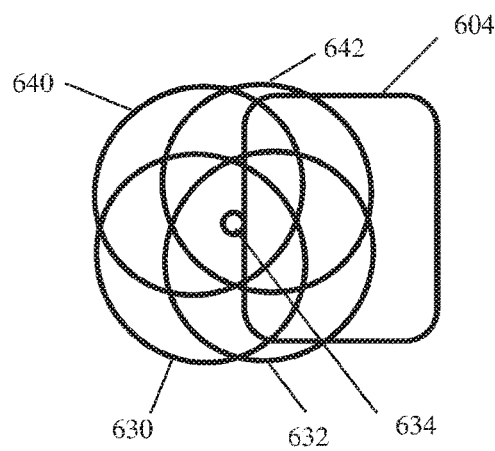

FIG. 6A and FIG. 6B illustrate an embodiment similar to that illustrated in FIG. 3A and FIG. 3B with four cameras. FIG. 6A and FIG. 6B show tooth 604, stylus 618 and cameras' FOV 630, 632, 640, 642. FIG. 6B shows that, when stylus 618 is moved around the tooth, at least two cameras have an unobstructed view.

Optionally, structured light can be projected onto the visible tooth portion/s and/or visible mouth portion/s in order to improve the accuracy of estimations of surface topography (e.g., of supragingival tooth portion surface topography) from collected images. In some embodiments, the SGMP includes one or more pattern projector for illuminating structured light. In some embodiments, patterns known in the art of 3D shape reconstruction using structured light are used. In some embodiments, patterns with spatial coding and/or wavelength coding and/or temporal coding (alternating structured patterns) as are known in the art of pattern projection are used. In some embodiments, a structured light projector is located on main body (e.g., 855 on FIG. 8). Alternatively, in some embodiments, a structured light projector is located on a separate unit from stylus and main body. A potential benefit of using structured light is that 3D depth information can be collected with one camera.

In some embodiments, the device includes cameras in addition to cameras in main body which are external to the main body and stylus. For example, a separate unit with an imager can be temporarily attached onto a tooth adjacent (e.g., tooth 344 or tooth 346 on FIG. 3B.) to the tooth to receive a crown or other prosthetic, whilst collecting measurements with SGMP (e.g., stylus scanning, collecting images). In some embodiments, the separate imager unit tracks stylus 318 and/or collects images of the tooth being measured and/or other mouth structures. In some embodiments, a structured light projector is located on an external cameras module/unit.

In some embodiments, an imager or cameras unit can be located at an opposite side of the jaw to the tooth being measured providing a side view of the tooth being measured and the stylus.

In some embodiments, a portion or portions of a main body and/or an imager unit can have a thickness such that the patient who is having a tooth measured can hold it in position by biting down on a portion of the imager or cameras unit. In some embodiments, an imager or cameras unit is used to keep the patient's mouth open during measurements. In some embodiments, an imager or cameras unit is held on an external fixture.

Figure 20:
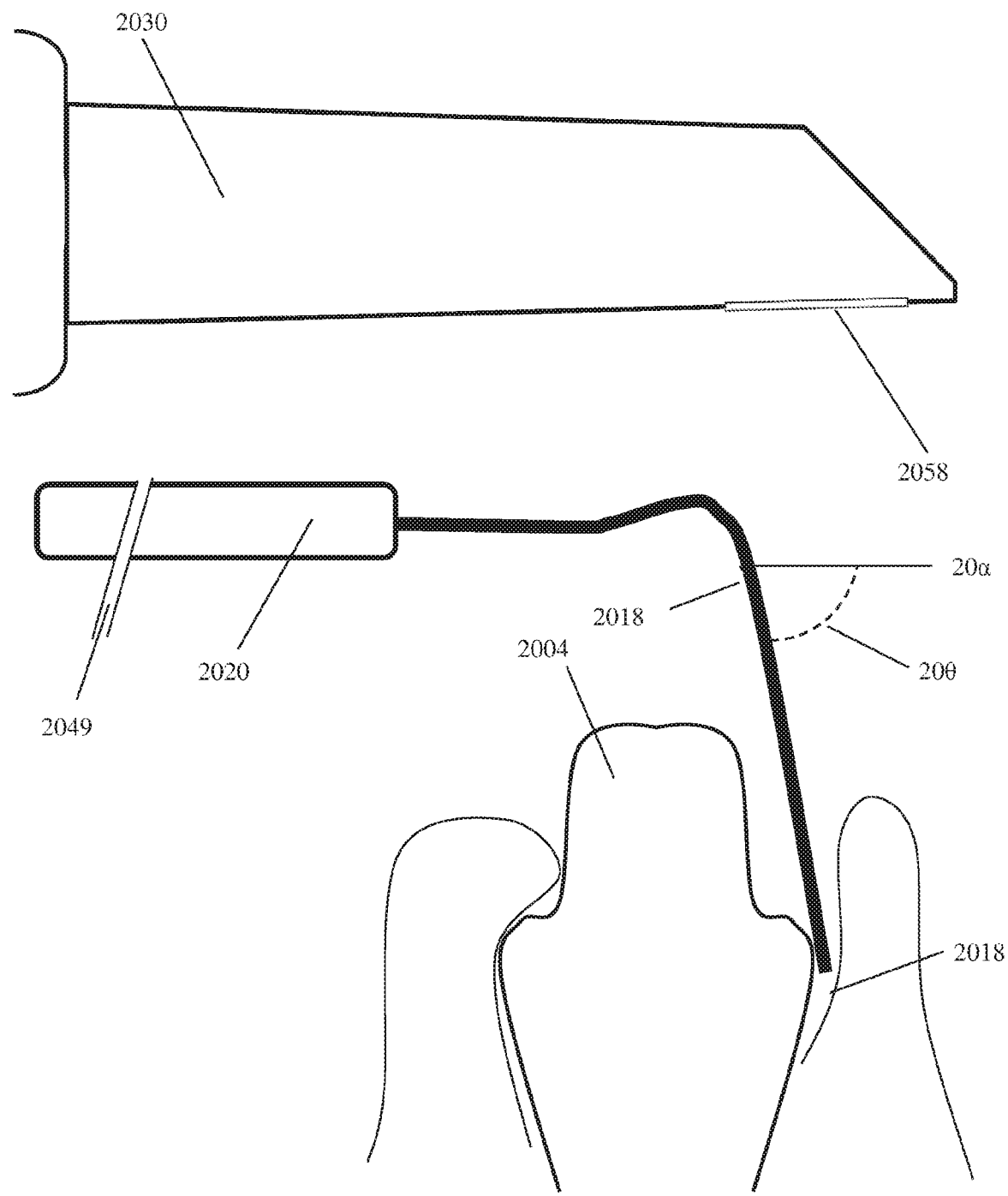
FIG. 20 is a schematic diagram of an embodiment where the stylus and imager are separate parts in accordance with an/some exemplary embodiment/s of the invention.

Optionally, in some embodiments, the main body does not include an imager/cameras, and the imager (e.g., cameras) are located on an external unit or units. In some embodiments an imager external unit or units are affixed to the patient's teeth and/or jaw and/or are hand held by a user. FIG. 20 is a schematic diagram of an embodiment where the stylus and imager are separate parts: A stylus 2018 is attached to a main body 2020. In some embodiments, main body 2020 is elongated as illustrated by a break 2049. An imager 2030 which includes a window 2058 is not attached to stylus 2019 or main body 2020. In some embodiments imager 2030, is a commercially (e.g., supra-gingival) available intraoral scanner, but the software of such scanner is modified, for example to support sub-gingival imaging and/or ignore the stylus during reconstruction, for example, as described below. As illustrated by FIG. 20, in some embodiments, stylus 2018 contacts tooth 2004 at a stylus tilt angle 20θ to the horizontal 20a, which is not 90° (e.g., as illustrated, tilt angle 20θ is less than 90°). A potential advantage of a camera-free main body is that is that stylus can have a very thin and lightweight handle (main body), as is common with dental tools e.g., dental probes. In some embodiments, a camera-free main body and stylus are disposable.

Optical measurement using high magnification cameras can be challenging as the Depth Of Field (DOF) or the range of depths for which the camera is in good focus may be relatively small (such as in microscopes). Depending on the lens numerical aperture of a camera, the camera DOF can be e.g. below 0.1 mm. Some existing intraoral scanners which do not use focus scanning (e.g., 3M ESPE Lava™ Chairside Oral Scanner), to collect measurements guide the user to in holding the scanner at the correct distance, through a user interface, for focus.

In embodiments where the stylus is attached to the imager, the distance between the stylus tip and the imager is mechanically stabilized meaning a range of focus distances of camera/s are set (e.g. at device manufacture and/or by the user before and/or during scanning). In some embodiments the range of focus distances (distances where images collected by camera are in focus) of the camera are set to cover a region of space at the stylus tip (e.g., at device manufacture). In some embodiments the rage of focus distances of the camera are set to cover an estimated region of space which includes the subgingival margin and/or visible tooth portion/s when the stylus is in contact with a subgingival tooth portion. A potential benefit of mechanically setting the distance between camera/s and/or final optical element/s is that the user is not involved with focusing the device or holding the device at the correct distance from the tooth to be measured for focusing. Another potential benefit of mechanically setting the distance between camera/s and/or final optical element/s is that focusing is more accurate and rapid making scanning faster and/or more accurate than existing dental scanners.

In some embodiments, measurements can be taken by collecting several images for each camera position at different focus distances (e.g., scanning lens focus), for example by moving the camera lens. In this embodiment scanning lens focus is combined with mechanical stabilization of the distance between the camera/s and the areas to be imaged, where mechanical stabilization is by stylus mechanical coupling to the imager final optical element. A potential benefit of scanning lens focus combined with mechanical stabilization of the focus distance to the region of interest in the tooth is that the number of focus distance steps (and/or required range of focal lengths) for a particular image sharpness (e.g. over the whole tooth) may be reduced. One manner of reduction (e.g., and speedup and/or accuracy improvement) is that images for focus distance steps to compensate for an unknown distance between camera and the region of interest in the tooth are not collected.

Some embodiments include one or more camera with a wider field of view which is used to collect additional images of the prepared tooth, and/or other teeth and/or mouth structure/s. In some embodiments, registering images of prepared tooth with wider field of view images are used to orientate the main body and/or in registration of measurements with a whole tooth model or teeth model.

In some embodiments, images including the tooth being measured and additional mouth structures (e.g., one or more image collected by one or more wider field of view camera) are matched with one or more image of the prepared tooth from the imager. This provides an orientation to collected images of the prepared tooth within the mouth assisting matching of prepared tooth images and/or measurements.

In some embodiments, a wider field of view camera is attached to the main body. In some embodiments, a wider field of view camera is attached to a mouth structure, or is held in position outside the mouth. In some embodiments, a camera with a wider field of view is used to collect images for construction of a coarse 3D model of neighboring teeth to the tooth being measured and/or of the whole jaw.

Optionally, the main body includes one or more additional camera/s where the camera/s are pointing in the opposite direction, for example additional camera/s are pointing approximately 180° from the direction of cameras collecting images of the prepared tooth (field of view is inverted). In some embodiments, camera/s pointing in the opposite direction collect of images of the opposite jaw to the tooth being measured.

In some embodiments, images of the tooth or teeth opposite to a planned prosthetic (e.g., crown, bridge) in the opposite jaw are used to provide a prosthetic which fits the tooth/teeth in the opposite jaw giving the prosthetic a good bite or closure with opposite teeth.

In some embodiments, the additional cameras FOV is located further from the prepared tooth than FOV/s of the imager, so that the location of additional camera/s may be less restricted than that of the imager (e.g., additional cameras can be placed in a SGMP handle). This may assist in maintaining a form factor and/or size suitable for intraoral use.

In some embodiments, the imager includes one or more mirrors with different angles which provide two or more fields of view to one camera. This may reduce the number of imaging sensors while allowing images from multiple points of views to be acquired.

In some embodiments, image processing (e.g., by processing application 1280 described below) of images (e.g., of marker, and/or stylus and/or stylus markings and/or visible tooth portion) can use subpixel resolution or super resolution providing resolution of $\frac{1}{10}$ of a pixel or more. In some embodiments, multiple interactions between a feature (e.g., marker, marking, tooth features) and pixels are used. In some embodiments, multiple images are used. For example, images can be aligned with each other and/or a model and/or markings can be measured with a sub-pixel accuracy using techniques that take advantage of the fact that an image feature (such as a tooth surface feature or marker) to be matched/measured intersects multiple pixels.

In some embodiments, imaging is during movement or vibration of one or more part of the SGMP. In some embodiments, one or more device parameters, such as a main body mass, a main body mass relative to a stylus mass and/or a main body mass relative to lateral movement spring forces, are selected so that movement or vibration of the stylus has a reduced or a known effect (e.g., by causing image smear). In some embodiments, a main body mass is high relative to a stylus mass and/or to lateral movement spring forces, reducing vibration of main body 820 during stylus 818 movement. In some embodiments, main body mass is more than 10 g or more than 20 g or more than 50 g or more than 100 g or more than 500 g. In some embodiments, ratio of a main body mass to a stylus mass is more than 2:1 or more than 5:1 or more than 10:1 or more than 50:1 or more than 100:1 or more than 1000:1.

In some embodiments, optionally or alternatively movement of the imager due to stylus vibration or movement is compensated. In some embodiments, movement of the imager is compensated by using image stabilization techniques as known in the art e.g., by synchronizing a movement of one or more imager lens and/or imager final optical element to the stylus movement. In one embodiment an imager lens moves with oscillations of the same frequency as vertical stylus scanning movements. Optionally or alternatively, a sensor, such as an accelerometer or gyroscopic sensor coupled to the main body, can also be used for detecting the scanning motions or vibrations and predicting them so that synchronization between movement, image processing and/or image acquisition, can be provided.

In some embodiments, an imager includes an imaging sensor and other optical elements (e.g., lenses), which together define an optical pathway which defines a field of view in the mouth. Optionally, one or more imager part is at a separate location from other imager part/s. The imager part with the shortest direct visible optical path to the stylus tip is herein termed 'imager final optical element' or 'final optical element' (e.g. a path folding mirror or lens or transparent solid optical port). In some embodiments, 'camera/s' are described and it is to be understood that, in these cases the words 'camera', 'cameras' and 'camera/s' are to be understood as equivalent to the word 'imager'.

In some embodiments, the stylus tip location is measured (e.g., by force sensor) at a higher rate than the camera/s collect images.

In some embodiments, the stylus tip location is calibrated to a tooth model coordinates system and the stylus tip location is measured at a higher rate than imaging.

Stylus Markings and Self-Calibration Optionally, as illustrated in FIG. 2A (and FIG. 3B), stylus 218 includes one or more markings 234 (and 334) along the stylus. In some embodiments cameras 230 and 232 optically track stylus 218 by taking images of stylus 218, including markings 234 along its body. Using stylus markings 234 the location of stylus body 218 and accordingly the location of stylus tip 222 relative to tooth 204 can be estimated from the images taken by said cameras even when stylus tip 222 is not visible to the camera.

In some embodiments, as illustrated in FIG. 2A and FIG. 3B, stylus markings are contrast color markings on the stylus. In some embodiments stylus marking/s can be mirror/s. In some embodiments stylus marking/s can be high contrast markers e.g. retroreflector, specular sphere, planar mirror, spherical shaped mirror. In some embodiments one or more stylus marking is self illuminating, (e.g. LED), optionally one or more self illuminating marking is powered by one or more wire which run through a hollow stylus connecting LED/s to a power source (e.g. battery). In some embodiments the stylus is hollow, illuminated from within (e.g., using an internal fiber optic and/or a light source attached at a base of the stylus), and marking/s are window/s or beam shaping elements in the stylus.

Optionally, stylus marking/s can be used for SGMP self-calibration of the imager: Known stylus dimensions and/or marker dimensions and/or distance between marker/s and/or displacement along the stylus of marker/s can be used to calibrate the imager where images of known distances/dimensions provide a scale to the imager. In one example, an image of the stylus including markings is acquired and the position of the markings on the image extracted. A comparison of the extracted positions to known positions can be used to determine calibration settings. A potential benefit of SGMP self-calibration is if the imager/camera/s suffer a mechanical shock (e.g. the device is dropped) or undergo thermal changes. Mechanical shock/s or thermal changes to SGMP can cause elements within the imager (e.g. cameras, camera lenses) to move meaning that any previous calibration (e.g. factory calibration) is no longer accurate.

In some embodiments the SGMP can self-calibrate the stylus tip location with respect to the imager (e.g. calibrate stylus length). In some embodiments SGMP stylus tip self-calibration is by imaging the stylus tip and stylus marking/s together and estimating the stylus tip 3D location in relation to the stylus body and stylus marking/s from the collected images.

In some embodiments the SGMP can self-calibrate the stylus tip location with respect to the imager using a tooth model (tooth coordinates system). The stylus tip 3D location in relation to the tooth coordinates system is estimated from collected images of the stylus and/or stylus marking/s and visible tooth portion or tooth marker/s. The SGMP imager or main body location with respect to the tooth coordinates system is estimated from images of tooth (or tooth marker/s). The stylus tip 3D location relative to SGMP main body is then estimated.

In some embodiments self-calibration is performed before starting measurements, e.g., in the clinical setting, outside of the patient's mouth. In some embodiments, (e.g. stylus tip self-calibration) is conducted following replacement of a part (e.g. replacement of a disposable part).

In an exemplary embodiment of the invention, calibration is used to adjust (and optionally match) the calibration settings of two cameras (e.g., if so provided). After calibration, the two cameras should estimate the location of a same marking (or the tip) to be the same.

In some embodiments at least some calibration is performed in the factory and/or after usage, for example, periodically or for a new batch of disposable components and/or per use. Different calibration levels and/or parameters may be performed at different times.

The calibration can include one or both of both imager camera "intra" parameters (e.g., focal length, center offset, lens distortion, CMOS pixels scaling and/or skew factors) and "inter" camera parameters (e.g., relative position, orientation, rotation and/or offset), the latter case being sometimes useful for stereophotogrammetry configurations whether passive or active. "inter" parameters relating camera position and/or orientation to SGMP body and/or stylus may be of interest (instead or in addition). In an exemplary embodiment of the invention, matching of points upon the stylus surface and/or given background/calibration target/projected pattern, whether in single or in multiple cameras images, together with the a-priori marking proportions reference is used for calibration parameters extraction and correction.

One example is a standard checkerboard pattern with given square size upon a plane: The distinguishable squares' cross points are detected and compared between the reference and resultant image. The reference image can be a theoretical pattern in case of a single camera calibration or an image acquired by a different camera. The deviation between the resultant grid vs. the reference one is then optionally formulated into a calibration parameters equation system and solved for parameter extraction.

Due to the perspective nature of the 3D into 2D camera projection (e.g., size vs. distance ambiguity), such a solution may miss one scaling parameter in the general case (e.g., occasional matching points and not specific calibration target) and a reference object of a known size may be used for a full calibration—the relative size of the object in the image plane with respect to its known size, reveals the missing scaling factor. Optionally, the markers upon the SGMP (e.g., stylus) are used to fulfill requirements for a full calibration.

Figure 21:
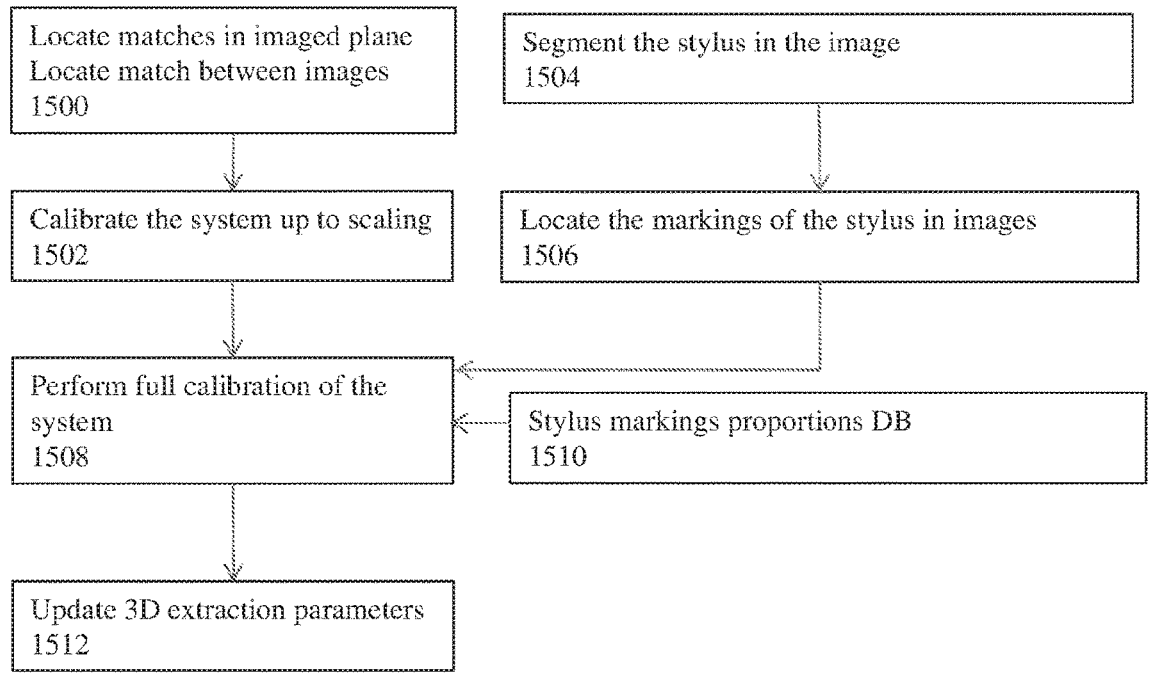
FIG. 21 is a schematic flow chart of a full calibration procedure, in accordance with an exemplary embodiment of the invention.

FIG. 21 is a schematic flow chart of a full calibration procedure, in accordance with an exemplary embodiment of the invention, which may be implemented for example, on a computer or other circuitry.

At 1900, first match points are located in the series of images/image pair/calibration target.

At 1902, various methods, for example, an 8 point algorithm in case of a stereo pair, may be used for system calibration up to scaling.

At 1904, optionally in parallel, the stylus is segmented out from the image 1904. Optionally, at 1906, markings of the stylus are detected.

At 1908, the relative markings locations in the calibrated up to scale system are optionally scaled 1908, for example, using a proportions database 1910.

At 1912, the resultant calibration parameters are optionally updated for 3D model calculation.

Stylus Tracking

In some embodiments, the stylus can move during scanning of a tooth. Such motion may be, for example, intentional (e.g., due to vibration) and/or unintentional (e.g., due to deflection of the stylus due to force exerted on it by a tooth). Optionally, the stylus tip 3D location is tracked with respect to the imager or main body e.g. tracking the movement of the stylus during scanning. In some embodiments, the location of the stylus markers is tracked, which can then be processed to yield a position of the tip.

In some embodiments tracking comprises optical tracking of visible portion/s of the stylus and/or stylus marking/s, optionally using images collected by imager. In some embodiments optical tracking is alternatively or additionally using an optical position sensor, e.g. position sensitive diode (PSD). In some embodiments optical tracking is by measurement of a direction of a beam reflected from the stylus or stylus marking/s.

In some embodiments images (frames) are collected by the imager determining the position of the stylus and/or stylus markings in each frame. In some embodiments the imager collects images at a frame duration and/or a frame rate is timed for capture stylus movements, such that the path of the stylus and/or stylus marking/s at each frame is seen as smeared image. Smeared stylus and/or marker/s images can be used to estimate the 3D path of stylus relative to main body during each frame period. For example, in some embodiments, the start and end of an image smear are used to calculate a stylus and/or marking/s starting and a finishing position respectively, the length of an image smear and/or the frame rate is used to estimate a stylus and/or markings speed of movement.

In some embodiments, the effect of stylus movement (e.g. vibration) on image smear measurements is reduced, and/or an image smear created by stylus movement is reduced by collecting images at a high sample rate and/or high shutter speed (e.g. 1 μsec), and/or increasing illumination (e.g., increased illumination facilitates high shutter speed). In some embodiments, the illuminator pulses and/or is synchronized with imager image capture (e.g. shutter speed and rate) In some embodiments, pulsing the illuminator saves power and/or reduces heat created by the illuminator.

Optionally, the location of stylus tip (e.g. relative to the main body) is tracked by using magnetic tracking where magnet/s or electromagnet/s (DC or AC modulated) are mounted to the stylus. For example, in some embodiments, one or more magnet and/or one or more electromagnet is attached to the stylus and one or more magnetic sensor is attached to the main body. In some embodiments magnetic tracking is of a scanning or vibrating (e.g. vertical scanning) stylus tip.

Optionally, the location of the stylus tip (e.g. relative to the main body) is tracked by mounting at least one mirror to the stylus, illuminating the stylus with collimated light and measuring a reflected beam direction with a Position Sensitive Diode (PSD) to measure stylus deflection. In some embodiments a PSD is attached to the main body. Optionally, the location of the stylus tip (e.g. relative to the main body) is tracked using one or more proximity sensor e.g. capacitive proximity sensor, optical proximity sensor. Optionally, the stylus position is estimated using one or more linear encoder/s e.g. capacitive encoder, optical encoder. Optionally, the stylus position can be estimated using one or more LVDT (linear variable differential transformer) sensor. In some embodiments proximity sensor/s and/or linear encoder/s and/or LVDT sensor/s provide stylus tip location to within 10 μm at a 10 kHz sampling (measurement) rate.

Optionally, the location of the stylus, and in particular of a vibrating stylus relative to scanner main body is tracked optically using two cameras. In some embodiments tracking is with a global shutter synchronized to stylus movements (e.g. vibrations) which captures the vibrating stylus smeared image. In some embodiments, a global shutter is synchronized to stylus vibrations by driving vibrations and camera using the same circuit and/or by adapting acquisition time to match the vibrations. In some embodiments, the stylus smear in captured image typically depends on the ratio between stylus vibration period and camera integration time. In some embodiments stylus vibration has a non-constant speed and the image smear depends on phase of the stylus vibration. In some embodiments the imager includes global shutter camera/s. In some embodiments rolling shutter cameras are used and optionally temporal distortion is compensated.

Optionally, a smeared path of one or more than one marking (e.g. high contrast marking) are mounted on the stylus during vibration is extracted from collected images.

Figure 10:
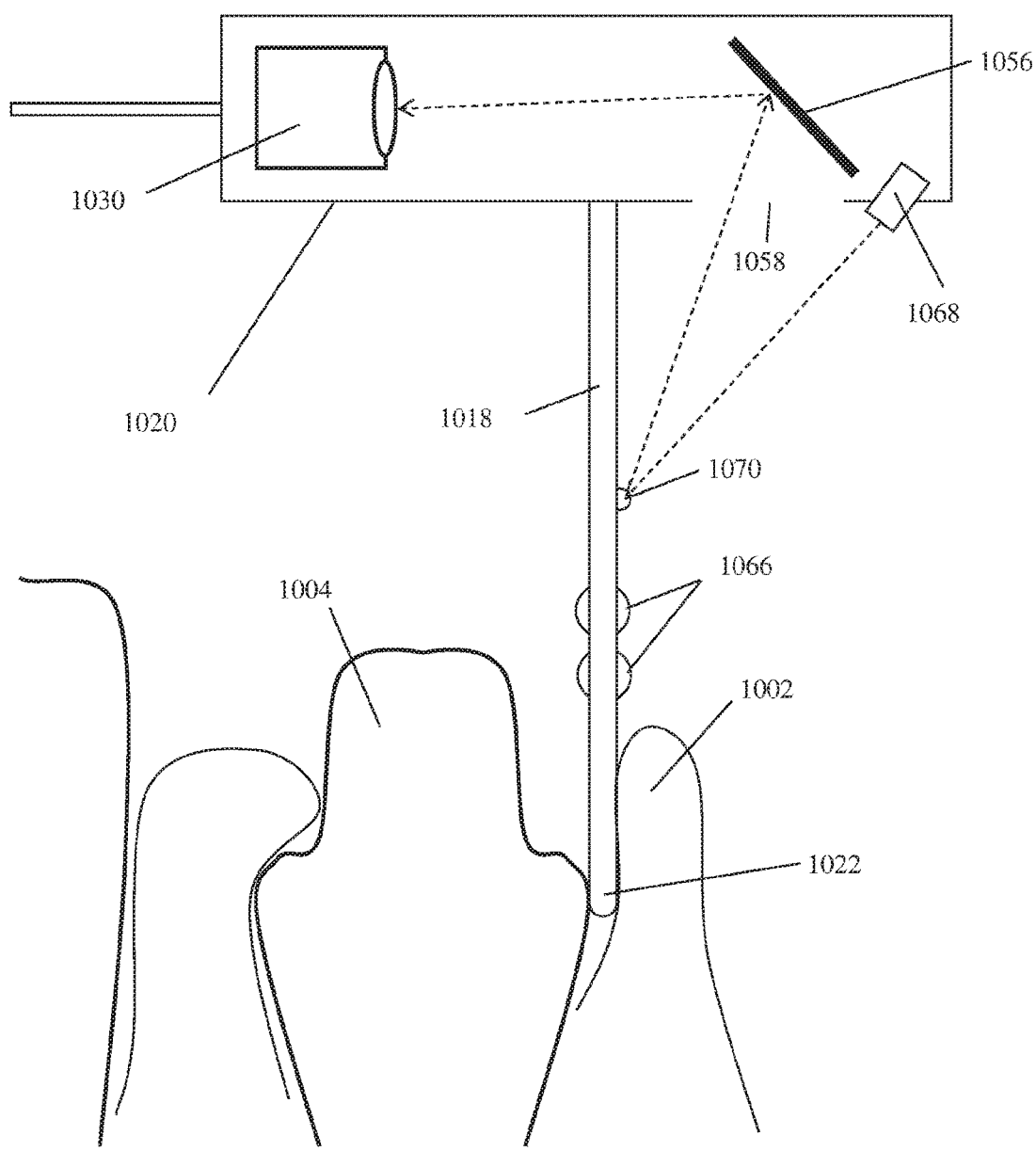
FIG. 10 is a schematic diagram of an embodiment where stylus movement is optically tracked in accordance with an/some exemplary embodiment/s of the invention.

FIG. 10 is a schematic diagram of an embodiment where stylus movement is optically tracked. A light source, for example a LED 1068 mounted to main body 1020 illuminates, stylus markings which, in some embodiments are selected so that reflection to the imager final optical element is specular and with known geometry relative to position. In some embodiments stylus markings are for example, specular spheres 1066 and/or a bump (e.g. 0.5 mm diameter spherical bump) 1070 mounted to stylus 1018. The dashed arrows emanating from LED 1068 show the light path from LED to camera/s 1030: LED light is reflected off of bump 1070 to mirror 1056 and is reflected from mirror to camera/s 1030. Camera/s 1030 see an image of a tiny very high contrast specular spot over bump 1070. The location of the specular spot is on the patch of bump 1070 with a normal parallel to the bisector of the angle formed by the light ray originating from LED light source 1068 to the specular spot and light ray reflected from said specular spot to mirror 1056 and camera 1030 (schematically indicated by dashed arrows). In some embodiments, estimation of the spherical bump 3D location from collected images takes into account the effect of slight movements of the imaged spot location over the specular bump.

In some embodiments, measurement is from a portion of collected images, a region of interest (ROI) which surrounds the stylus location. In some embodiments only the ROI is imaged (imaging is of a portion of the cameras FOV). A prospective benefit of using a ROI is reduction in imaging and/or processing. In some embodiments, the ROI is changed with time in order to track the moving stylus. In some embodiments, if the stylus is not found in the ROI, the ROI is enlarged.

In some embodiments the location of a vibrating stylus relative to main body is tracked using two fast cameras, e.g. cameras operating at a rate of 120 frames per second or higher, which image the vibrating stylus markers with a small (e.g. about 30% or about 20% or about 10% or about 1% of the image size) region of interest (ROI) for stylus tracking at an even higher rate for example about ×5 or about ×10 or about ×100 the fast cameras base images rate e.g. 1200 frames per second. In some embodiments images of the whole camera/s FOV can be taken at lower rate, for instance at 60 frames per second while the imaging at the ROI are collected at a high rate.

Device with rounded Stylus Tip

Figure 7:
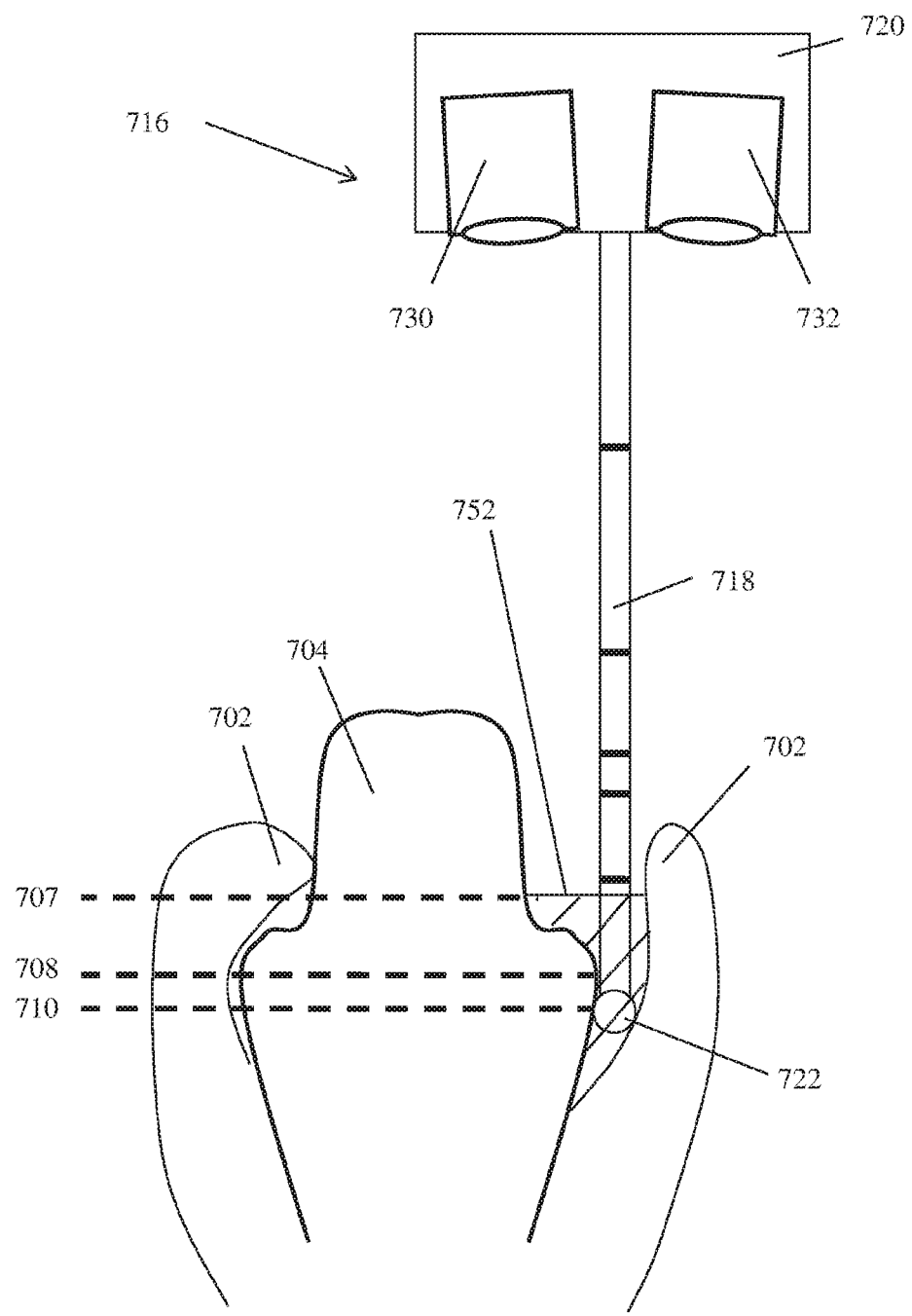
FIG. 7 is a schematic diagram of an embodiment with a spherical stylus tip in accordance with an/some exemplary embodiment/s of the invention.

The stylus tip can have various shapes, depending, for example, on one or more of desired effect, spacing between teeth, angle of access, damage to gums and/or accuracy considerations. For example, the tip shape can be a cone shape, an inverted cone shape, a flattened shape, a spherical shape or another rounded shape such as an ellipsoid. In this and other embodiments the tip can be rounded, for example, spherical or non spherical. As an example, spherical tip shapes are described herein with respect to some embodiments. FIG. 7 is a schematic diagram of an embodiment with a spherical stylus tip. FIG. 7 illustrates an embodiment for tooth measurement below the preparation finish line 708 and/or of a natural tooth emergence profile, and/or below a line of maximum tooth cross section, and/or of tooth surfaces where the angle of the tooth to the apical-coronal direction increases. FIG. 7 illustrates an embodiment where stylus 718 has spherical stylus tip 722 with a wider diameter than the stylus. For example, as illustrated in FIG. 7 stylus 718 and stylus tip 722 are in position to measure a tooth surface below or apical of preparation finish line 708.

A potential benefit of embodiments where the stylus tip is wider than the stylus body is that the tilt angle θ (illustrated in FIG. 3B) of the stylus to the horizontal may be reduced for subgingival measurements.

A potential benefit of measuring the emergence profile of the natural tooth below the preparation finish line is that prosthetics constructed using the emergence profile measurements which match or blend with the emergence profile have a smooth surface junction with the natural tooth. Introduction of a prosthetic which has a smooth surface junction with the natural tooth does not provide a gap or crevice for bacteria to grow.

In some embodiments other stylus tip shapes collect measurements apical of the preparation finish line, for example a stylus with a spade shape with a flattened tip which is wider than a stylus body portion adjacent to the tip is inserted easily by inserting the flattened side of the tip parallel to the tooth surface. The spade shaped stylus tip is then rotated 90° for measurements. A conic stylus tip or other shapes known in the art for stylus scanner tips are also envisioned and encompassed.

FIG. 7 also illustrates the ability of many described embodiments to measure visually obscured tooth surfaces: Stylus tip 722 is submerged under fluid 752. Fluid 752 can be from crevicular fluid in the sulcus and/or gingival bleeding caused e.g. damage to the gingival tissue during tooth preparation and/or periodontal inflammation. A potential benefit of the above described ability to measure under fluid is improved speed over subgingival measurement existing techniques where bleeding or other fluids must be absorbed or prevented before measurement is possible.

FIG. 7 also illustrates an embodiment of cameras 730, 732 positions/orientations within/on main body 720. Cameras 730, 732 are angled towards stylus 718 so that cameras' FOV are orientated towards the tooth and stylus. In some embodiments, the stylus and/or stylus tip is constructed of a softer material than tooth material (e.g. enamel, dentine). In some embodiments, scanning a tooth with the stylus does not scratch the tooth surface. In some embodiments, the stylus is constructed of metal coated, at least at the stylus tip, with a soft coating where the soft coating is made of a material softer than tooth material (e.g. enamel, dentine).

Mirror Imager Final Optical Element

Figure 8:
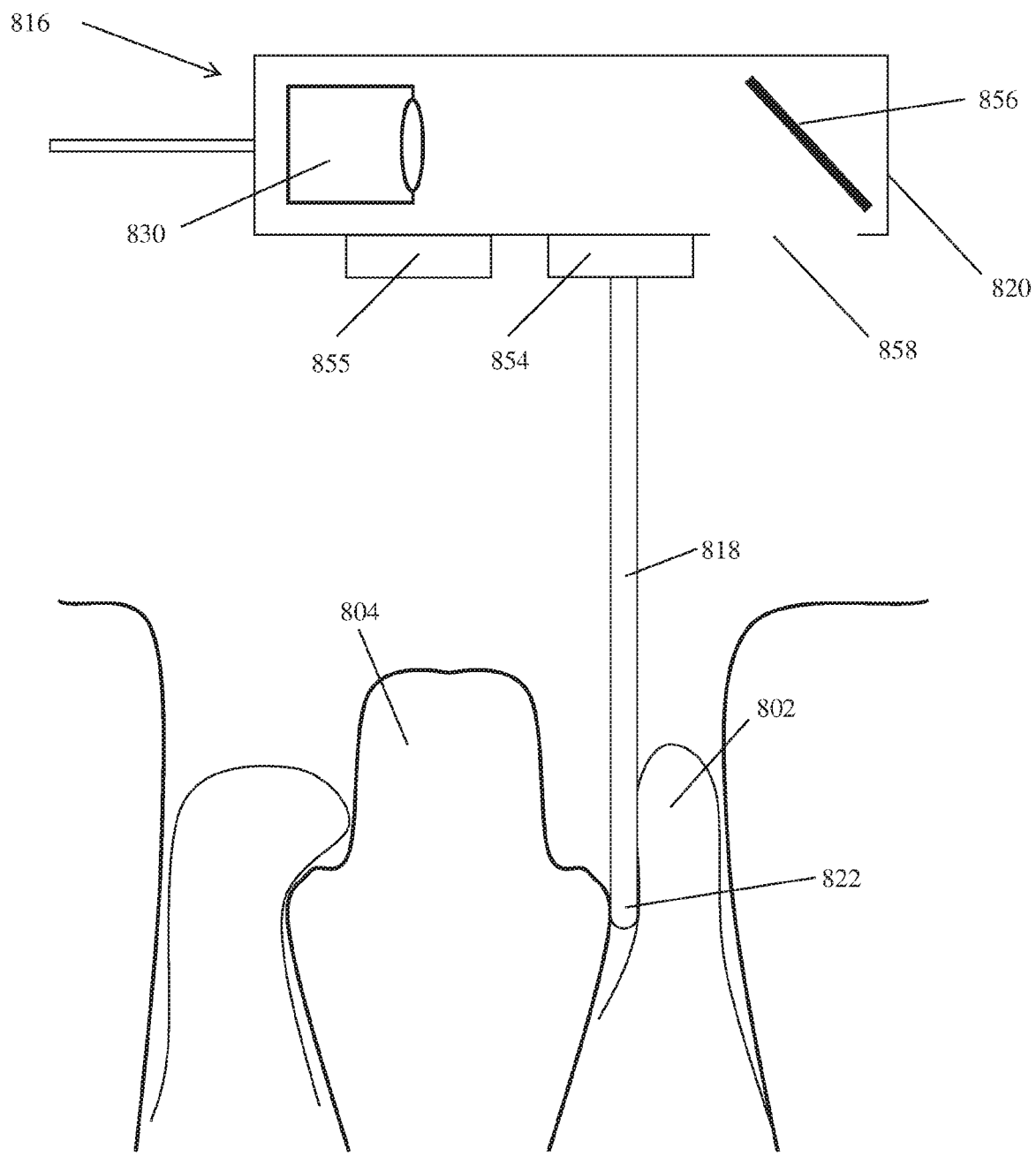
FIG. 8 is a schematic diagram of an embodiment including a sensor in accordance with an/some exemplary embodiment/s of the invention.

Optionally, SGMP 816 can include an angled (or folding) mirror 856. FIG. 8 illustrates a mirror 865, an imager final optical element which, as described above, fits into the patient's mouth and is in close proximity (e.g. within 4 cm of) to stylus tip 822. Mirror 865 reflects a FOV (e.g. including prepared tooth 804 and/or stylus 818 and/or mouth structure/s) to an imager or camera/s 830 which allows the imager or camera/s 830 to be at a larger distance from the tooth than the distal end of stylus 818.

Optionally, a main body entrance aperture 858 is covered by a transparent window (not shown in FIG. 8), such as a glass window. The transparent window protects the mirror from liquids (e.g. droplets, spills) and/or dirt and can be cleaned easily. In some embodiments the window and/or other optical elements (e.g. camera/s) include one or more heating system (e.g. to heat the window and/or camera lens) to prevent condensation from obscuring imaging.

Sensors

In some embodiments, SGMP 816 includes one or more sensor. FIG. 8 is a schematic diagram of an embodiment including a sensor. Sensor/s are located for example, on the stylus (including stylus body, stylus proximal end and the stylus tip) and/or on the main body and/or mounted to a mouth or facial surface (e.g. tooth, gum, lip, cheek) and/or mounted to another component (e.g. pointer, alternative dental tool).

In an exemplary embodiment of the invention, stylus 818 is connected to main body 820 through a sensor 854. In some embodiments sensor 854 is a load cell. In some embodiments load cell 854 measures the applied force on stylus 818 connection to main body 820 in up to three directions. In some embodiments the location of the stylus tip 822 (stylus deflection) relative to main body 820 (stylus end location) can be determined from load cell measurements. In some embodiments stylus 854 moves with respect to main body 820 and load cell 854 measures stylus movement with respect to main body.

In some embodiments measurements of stylus deflection are used to determine stylus tip location. In some embodiments, to determine stylus tip location from stylus deflection measurements are calibrated. For example, in one embodiment, the force measured by the load cell is calibrated with possible deflections of the stylus including stylus tip lateral and/or vertical movement. In an exemplary embodiment of the invention, a jig is used to provide the deflections.

In some embodiments mechanical stylus deflection measurements (e.g. load cell measurements) can be made at high sample rates e.g. 10 kHz for load cells. High rates of stylus deflection measurement facilitate rapid scanning (and measurement) of subgingival surfaces with the stylus tip 822. A potential benefit of using mechanical measurements to track/determine stylus tip location is that mechanical measurements can partially or fully replace stylus optical tracking. In some embodiments mechanical measurements are used to track stylus tip location at a high rate e.g. 10 kHz sample rate (compared to a 60 Hz sample rate for common 60 FPS imagers).

In some embodiments combining mechanical measurements or tracking of the stylus tip with imaging where the stylus tip location is not determined from images (even where low rate mechanical measurements (e.g. below 10 kHz) are used) which reduces the image processing requirements on the imager and/or the resolution and/or sample rate of images. In some embodiments mechanical stylus measurements, such as those collected by load cell 72 are combined with measurements/mode (e.g. from an existing current intraoral scanner) to generate a tooth model including subgingival tooth regions. Combining mechanical stylus measurements with an existing model (as opposed to combining image measurements) reduce image processing as alignment is of mechanical measurements to a model, not of multiple images to a model.

Optionally, the stylus end location can be alternatively or additionally determined from stylus deflection measurement by one or more strain gauge (as described in more detail with reference to FIG. 9A below). In some embodiments strain gauges can be applied to the stylus at several locations (e.g. sensors 921 on FIG. 9A). In some embodiments, the bends in a known manner. In some embodiments, the stylus is designed to have a weak point (e.g. where stylus thickness is smaller than one or more adjacent stylus portion), where most bending occurs. In some embodiments stylus deflection is measured by a strain gauge located at the weak point.

In some embodiments stylus deflection can be measured using a combination of measurement methods, such as optical measurement of markers (as described previously) and mechanical measurement (e.g. by load cell).

In an exemplary embodiment stylus 818 scans tooth 804 vertically whilst remaining in contact with the tooth surface: The stylus body is moved in the vertical (apical-coronal) direction and the stylus tip is deflected by the tooth following the surface of the tooth apically (downward). The vertical scan can be, for example 2 mm long at 50 Hz. In some embodiments, whilst the stylus is scanning vertically, the stylus deflection is measured at a high rate e.g. by load cell 854 at 10 KHz, such that for an exemplary 50 Hz scan cycle, for each vertical scan cycle the location of 200 points is measured.

In some embodiments, the user moves the vertical scanning (or vibrating) stylus horizontally around the tooth (e.g. following path 219 illustrated in FIG. 2D), at a rate compatible with the imager scanning rate. For example, if the imager scanning rate is 10-60 frames per second, to image at least 500 scan positions around the tooth, the stylus is moved around path 219 in 8-50 seconds.

In some embodiments the SGMP includes a Position Sensitive Diode (PSD) (e.g. for optical scanning). In some embodiments the PSD is attached to the main body. In some embodiments the SGMP includes one or more proximity sensor e.g. capacitive proximity sensor, optical proximity sensor (e.g. for stylus tracking). Optionally, the SGMP includes one or more linear encoder/s e.g. capacitive encoder, optical encoder and/or one or more LVDT (linear variable differential transformer) sensor (e.g. for stylus tracking). Optionally, the SGMP includes magnet/s or electromagnet/s (DC or AC modulated) mounted to the stylus (e.g. for stylus tracking).

Optionally, measurement from sensor/s can be used to verify that the stylus tip is in contact with the tooth subgingival surface.

In some embodiments verifying contact of the stylus tip with the tooth is by a measure of stylus deflection. In some embodiments stylus contact with the tooth subgingival surface is verified for a stylus deflection direction or a range of stylus deflection directions. In some embodiments stylus contact with the tooth subgingival surface is verified when stylus deflection direction is perpendicular to tooth surface: The tooth surface direction can be extracted directly from an updated tooth model and/or from the direction of stylus tip movement when scanning around the tooth (e.g. following path 219 illustrated in FIG. 2D.) In some embodiments a specific stylus deflection or pressure range indicates that the stylus is in contact with the tooth. In some embodiments stylus deflection is measured by one or more strain gauge on the stylus and/or by a load cell and/or by other methods of measuring stylus deflection and/or force as described above (e.g. optical), and/or other methods known in the art.

In some embodiments verifying contact of the stylus tip with the tooth is by verifying a magnitude and/or direction measure of force applied to the stylus tip. In some embodiments, contact of the stylus tip with the tooth is verified for a threshold applied force magnitude (e.g. measured by load cell 854 on FIG. 8 and/or measured by a force sensor at the stylus tip) at the stylus tip. In some embodiments, contact of the stylus tip with the tooth is verified for an applied force direction, which depends on the location of the stylus with respect to the tooth (e.g. position of stylus on path 219 illustrated on FIG. 2D). In some embodiments the applied force direction is calculated (e.g. by processing application 1280 on FIG. 12) from real-time images.

In some embodiments verifying contact of the stylus tip with the tooth is by verifying that the stylus is within a depth and/or height range (e.g. stylus tip depth with respect to a preexisting model, stylus depth with respect to a marker on the tooth).

If the stylus body contacts a tooth surface (e.g. when measuring below the preparation finish line, between adjacent teeth) stylus deflection measurement to verify stylus tip contact with the tooth surface can provide a false positive. In some embodiments one or more estimates of stylus location in relation to a known teeth model is used to ascertain a risk that the stylus body touches a tooth surface (e.g. prepared tooth surface above the surface being measured) and is used to discount false stylus contact verification. In some embodiments an algorithm identifies false stylus contact verification using the stylus tilt angle and/or a measured tooth gradient/slope of decent (in the apical direction) during scanning; e.g. if the gradient zeros or is less than expected, indicating that the stylus tip is being prevented from reaching the tooth surface (e.g. by stylus body), the algorithm indicates a false contact verification.

Figure 9A:
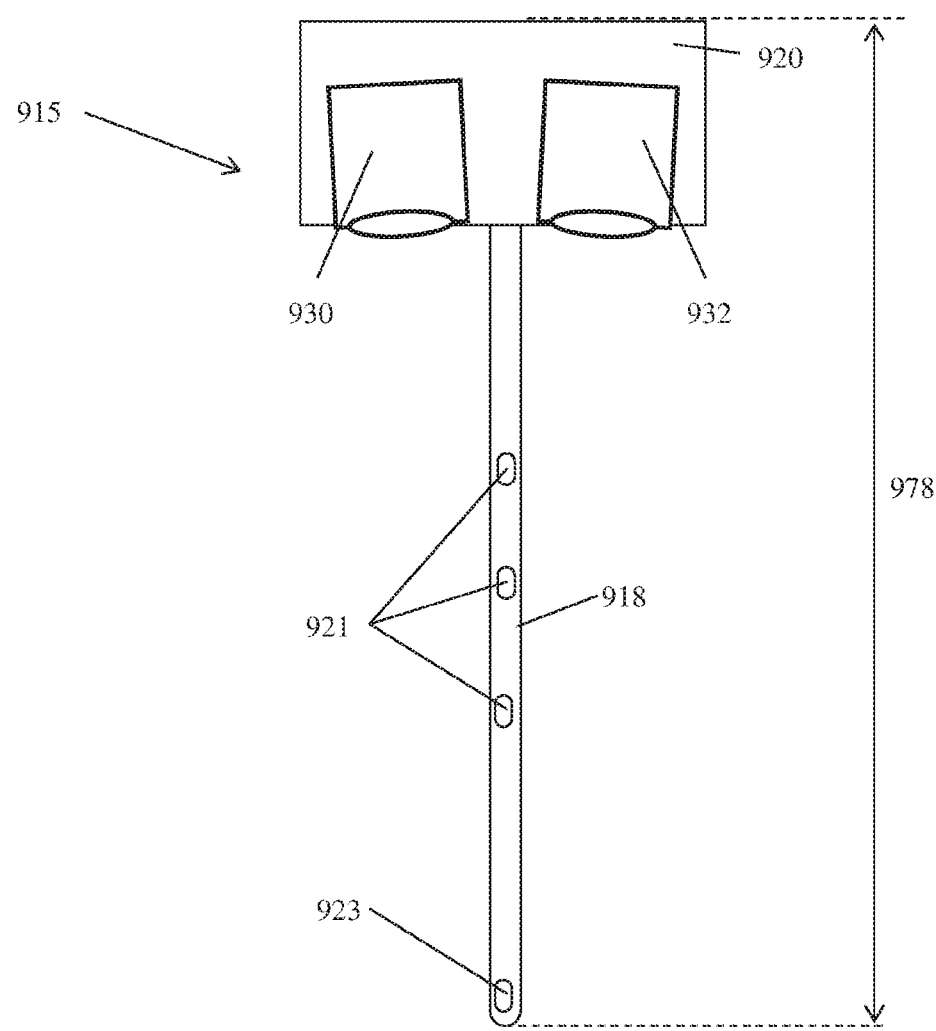
FIG. 9A is a schematic diagram of an embodiment with a sensor at the stylus tip in accordance with an/some exemplary embodiment/s of the invention.

FIG. 9A is a schematic diagram of an embodiment with a sensor located at the stylus tip. FIG. 9A illustrates an embodiment with a sensor 923 at the stylus tip and sensors along stylus length 921. In some embodiments sensors 921 are strain gauges. In some embodiments sensor 923 is a force sensor such as load cell, strain gauge. The force sensor located at the stylus tip 923 measures the force applied at the tip and not over all of the stylus as, for example when measuring stylus deflection at stylus base or over the whole stylus body.

In one embodiment contact of the stylus tip with the tooth is verified using a two part stylus where the stylus tip moves with respect to a second stylus part. Imaging or tracking of this movement, optionally assisted by markers, can be used to verify stylus tip contact with the tooth surface.

Figure 9B:
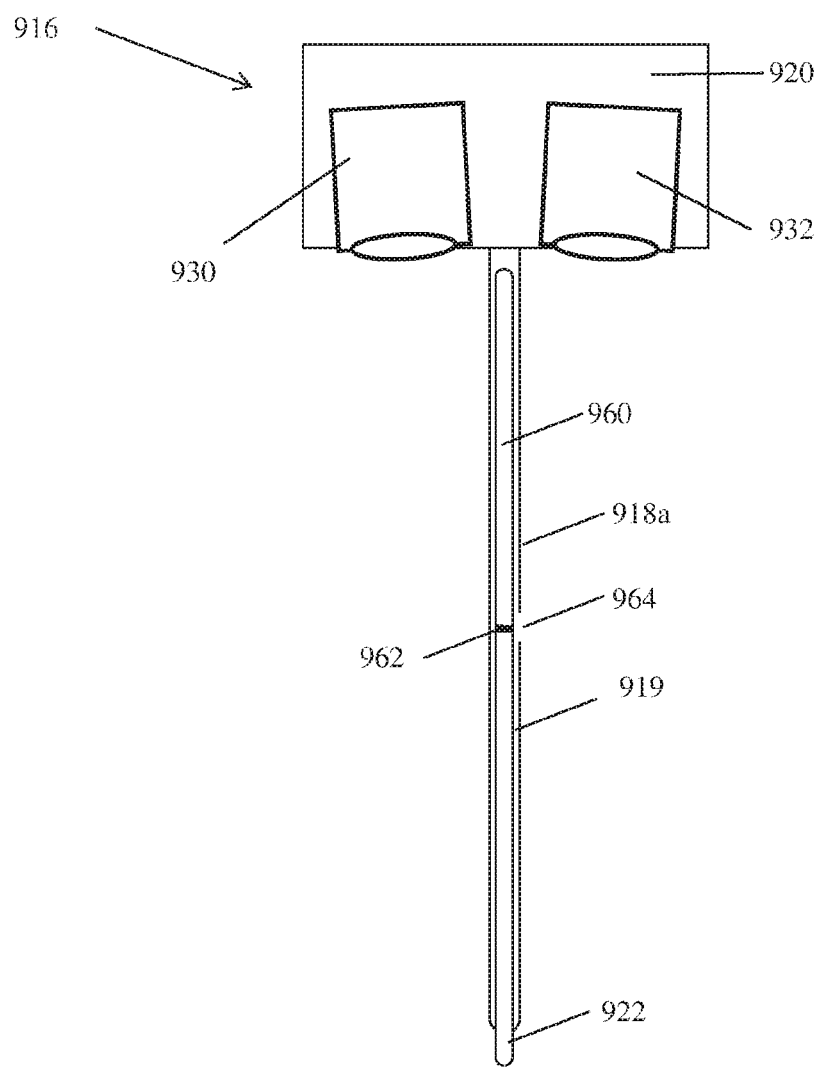
FIG. 9B is a schematic diagram of an embodiment with a mechanism for optical verification of contact between the stylus and subgingival preparation margin in accordance with an/some exemplary embodiment/s of the invention.

FIG. 9B is a schematic diagram of an embodiment with a mechanism for optical verification of contact between the stylus tip and subgingival preparation margin. Stylus 918 is hollow and includes an internal post 960, optionally coaxial, that is connected to stylus tip 922. Post 960 is slightly smaller in diameter than the inner diameter of hollow stylus 918 and can slightly move laterally and/or vertically) within hollow stylus 918*a* when force is applied to stylus tip 922. In some embodiments movement of internal post 960 is be viewed and measured by cameras 930 and 932.

Optionally, measurement of post movement (e.g. lateral movement) is by viewing a marking 962 on post 960 through a window 964 in hollow stylus 918*a*. In some embodiments hollow stylus 918*a* has multiple windows corresponding to multiple markings on post 960. Optionally, the windows include markings (e.g., graduations and/or edge markers) so they can be identified in the acquired images of the stylus. The windows in hollow stylus 918*a* can be used in addition to or instead of stylus markings.

Optionally, post movement (e.g. lateral movement) is measured electrically: In some embodiments post 960 is electrically isolated from hollow stylus 918*a* and electrical measurement of post movement with respect to hollow stylus is, for example by measurement of the capacitance between post 960 and hollow stylus 918*a*.

In some embodiments filling a gap 919 between internal post 960 and external stylus 918 is filled with a flexible material, e.g. silicone or RTV (Room Temperature Vulcanizing) silicone which provides stability to stylus tip 922 whilst allowing movement of post 960 relative to hollow stylus 918.

Lateral Actuation

In some embodiments a stylus connection to the main body is using a movement mechanism which allows the stylus tip to move and/or a mechanism which causes it to move horizontally. Exemplary movement amounts are 2 mm, 1 mm, 0.5 mm and/or intermediate or smaller amounts of movement, optionally symmetrical. Optionally, movement is used to assist the stylus in following a subgingival tooth surface contour e.g. during vertical stylus scanning. During vertical scanning, the stylus tip can be caught by a step like subgingival preparation margin and not descend apically of the step. In some embodiments the SGMP includes a movement mechanism which moves the stylus laterally when the stylus encounters a high angle feature (e.g. subgingival margin step). In some embodiments a movement mechanism to move the stylus laterally or horizontally is a flexure. In some embodiments the movement mechanism includes a vertical actuator. In some embodiments the vertical actuator can move and/or vibrate stylus tip 612 vertically by 1-5 mm. In some embodiments vertical stylus movements are less than 15 mm or less than 10 mm and lateral movements are less than ±10 mm or less than ±5 mm.

In some embodiments the movement mechanism comprises a flexure that includes a vertical actuator (for vibrating stylus tip vertically by 1-5 mm) and two tilting actuators (optionally with electrical or optical encoding) which can move the stylus tip laterally by ±1 mm. In some embodiments the stylus tip is scanned vertically over tooth surface contour whilst preventing the stylus tip from colliding and/or being caught by into sharp angled features (e.g. a step shaped preparation margin) by moving the stylus laterally to avoid the sharp angled feature/s. In some embodiments avoiding contact or scanning of sharp angled features is by control of the lateral actuators using real time information of the force applied to stylus tip (e.g. using force sensor/s as described above), and/or a preexisting tooth model (e.g. a tooth model indicating a likelihood of and/or location of a step shaped contour). Optionally, a scanning control software determines and/or predicts (e.g., using prediction methods known in the art) where the stylus may get caught and moves the stylus away from such a problem location.

Side Attached Stylus

Figure 11:
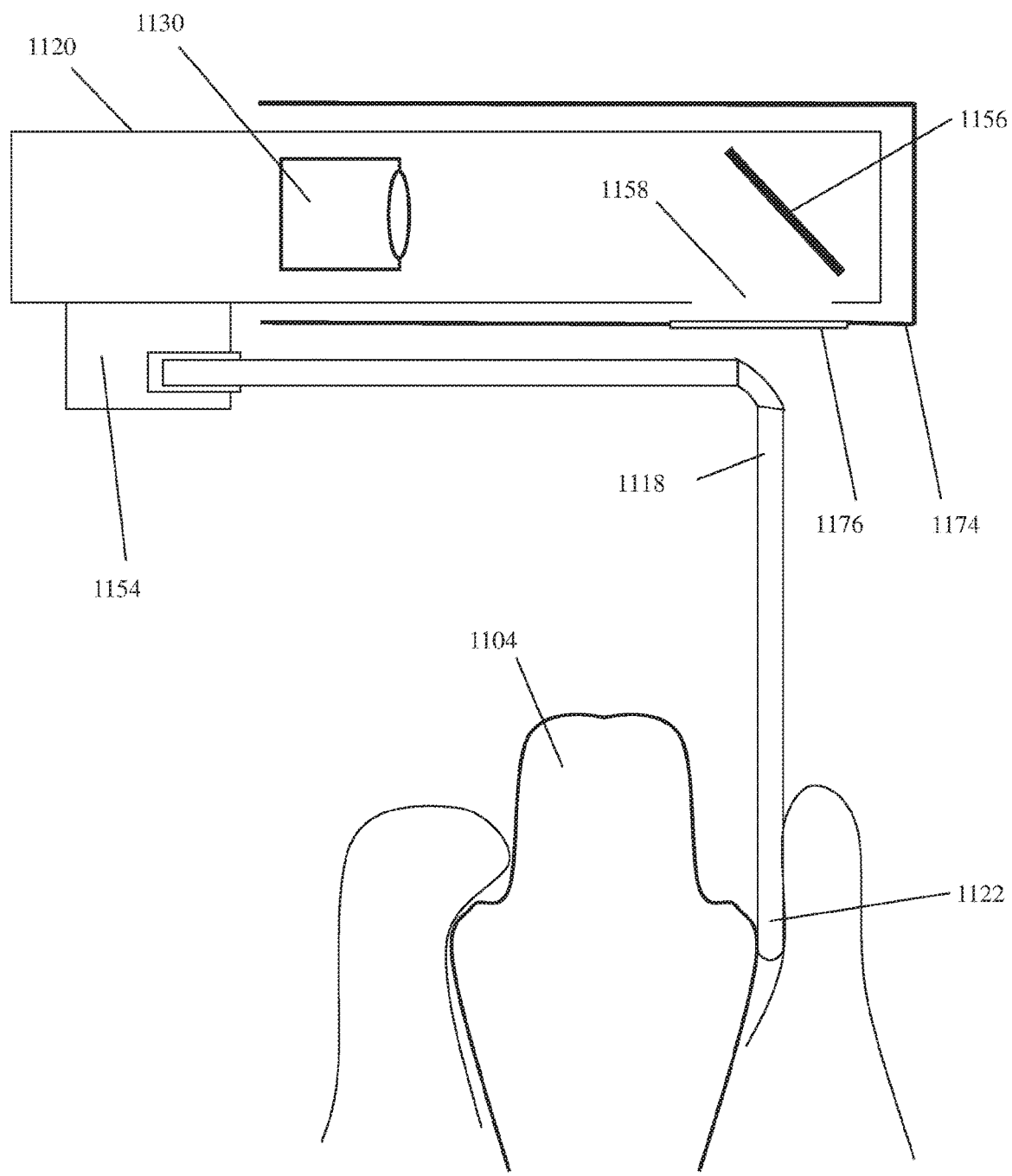
FIG. 11 is a schematic diagram of an embodiment with a side attached stylus in accordance with an/some exemplary embodiment/s of the invention.

FIG. 11 is a schematic diagram of an embodiment with a side attached stylus: Stylus 1118 is connected to main body 1120 to the side of the imaging port/window. In this example, stylus 1118 is L-shaped including a measurement portion (vertical in FIG. 11) and an attachment portion (horizontal in FIG. 11). In some embodiments, as illustrated in FIG. _11, an angle of connection between stylus attachment portion and measurement portion is approximately 90°. In some embodiments the angle of connection measurement portion of stylus 1118 is tilted and is at more or less than 90° to the attachment portion. Stylus 1118 connects to main body 1120 through housing 1154. In some embodiments housing 1154 includes a load cell and/or other force sensor/s.

A potential advantage of connecting stylus 1118 at the side of main body (and embodiments where the imager is not attached to the stylus as illustrated in FIG. 20) 1120 is that an optical path between tooth 1104 and the imager is not obscured by the connection between the stylus and the main body. In some embodiments, as described above, the imager, e.g. camera/s 1130, collects images which are used to track stylus 1118.

Optionally, the stylus can be disconnected from the main body. In some embodiments SGMP includes a mechanical connector element (e.g. dove tail shaped joint, ball and socket joint, optionally with a hexagonal connector preventing rotation) that enables easy connection and disconnection of the stylus from the main body. In some embodiments the connector includes a release button (e.g. release button 1999 on FIG. 19) which, when pressed by a user releases and/or opens the connector. In some embodiments the mechanical connector element ensures a good connection of the stylus to the main body with small movement (<10 µm) of the stylus (e.g., at the connection point and/or stylus tip) and main body relative to each other (due to mechanical connector tolerances) during measurement. In embodiments where the stylus and main body have small movement relative to each other during measurement, stylus tip location measurements can be using force measurements as described above. In embodiments where the stylus is tracked optically larger movements between stylus and main body may be tolerated.

A potential benefit of a removable stylus is that the stylus may be sterilized by autoclave, as the current common practice for dental probes. This is in contrast to sterilization of existing intraoral scanners which is generally achieved by cleaning of the scanner intraoral portion with alcohol/chlorhexidine/peroxide wipes, since autoclaves can damage cameras or other components. Another potential benefit of a removable stylus is that the stylus can be disposable and/or the stylus can be replaced in the event of damage or natural wear, without requiring the SGMP itself to be replaced.

A potential advantage of a side connection is that a cover (e.g., a condom) may be placed over the SGMP and not interfere with the stylus connection, which is further away from the SGMP tip.

Disposable Parts

Optionally, portion/s of the device are disposable. In some embodiments the stylus is disposable. In some embodiments the device includes a disposable imager cover. In some embodiments the stylus can be easily connected and/or disconnected to and from main body. In some embodiments an easily connectable/removable stylus is disposable.

In some embodiments a disposable cover, which is replaced between different patients, covers at least one camera or optical window reducing the risk of contamination between patients. FIG. 11 illustrates a cover 1174 which can be disposable. Cover 1174 includes a cover transparent portion 1176 over window 1158.

In some embodiments the stylus is connected to (or integral with) a cover outside of the cameras viewing area (e.g. at the side) with the housing connecting the cover and main body. In some embodiments stylus is connected to a cover forming one disposable part. In some embodiments stylus is connected to a cover and stylus and cover dismantle into two or more units of which one or more unit is disposable.

In an exemplary embodiment of the invention, a load cell for measuring stylus movement is provided on the SGMP body, adjacent to an expected location of the stylus. When a cover with a stylus is placed on the SGMP, the stylus can be read by the load cell (and/or other sensor). Optionally, the stylus includes a portion which extends past the cover towards the SGMP. Such an extension may assist with alignment and/or relative locating. Optionally or alternatively, other matching features between the cover and the SGMP body are used for locking and/or alignment between the cover and/or stylus and the SGMP body. In one example, the matching feature comprises a ring (e.g., a notch and a matching groove).

In some embodiments, the disposable part includes only plastic parts, possibly with some metal used for ensuring desired rigidity. Optionally or alternatively, the disposable parts include some electronics (e.g., sensors, amplifiers for the sensors and/or illuminators, optionally with power supplies). In such embodiments, the electronics optionally include one or more contacts which match one or more contacts in the SGMP, for example, on a body thereof and/or in a socket thereof. Optionally or alternatively, wireless link methods, such as Bluetooth are used for communicating between the disposable electronics and the rest of the SGMP. In some embodiments, the disposable part may include optical elements (e.g., a reflector and/or a lens). In some embodiments, an imager is included in the disposable parts.

Tooth Model

In some embodiments measurements including imaging and stylus measurements are used to produce a tooth model. This tooth model may, for example, be used as is or may be registered to and/or combined with a separately acquired tooth model.

In some embodiments, estimate/s of stylus tip position with respect to supragingival tooth portions are used to generate a model of a subgingival surface topography of the tooth. In some embodiments images of visible tooth portion/s are combined with subgingival measurements to create a model of subgingival and supragingival surface topography of the tooth.

Optionally, gingiva position with respect to supragingival tooth portions is estimated from images, for example, by identifying gingiva tissue, e.g., based on color, and calculating a location in the image coordinates. In some embodiments gingiva position with respect to supragingival tooth portions is estimated from preexisting models/measurement (e.g. from digital imaging, CT, MRI scan). In some embodiments gingiva position with respect to supragingival tooth portions is used to generate a gingival (or gum) line on a model of the surface topography of the tooth.

In some embodiments a preparation finish line is indicated on the tooth model e.g. to assist matching of a crown finish line to the preparation finish line. In some embodiments a preparation finish line is estimated from a tooth surface topography model (e.g. by identifying a step shape). In some embodiments the preparation finish line is estimated from a subgingival margin tooth surface topography model. In some embodiments the preparation finish line and/or a prosthetic finish line can be added to the tooth model by the user manually scanning the stylus tip over the preparation finish line or over a desired prosthetic finish line. Optionally, the user controls a user interface (e.g., a touch screen, mouse based interface and/or a button) to indicate that a stylus contact is for marking rather than and/or in addition to measurement. Such a marking is optionally added to the model and may be viewed and/or otherwise used downstream for example, by a technician. Optionally, this enables a dentist to decide and/or provide input on the size and shape (e.g., does it surround the whole tooth or not and where) of the crown, rather than only a technician applying his own judgment.

In an exemplary embodiment of the invention, such marking may be used as part of scanning process, for example, to indicate to the system where a better scanning is needed and/or where a step in the subgingival area is formed. Optionally, the system uses such markings to ensure that sufficient data points are acquired where needed for reconstructing a tooth model showing those parts for which an accurate model is needed according to the markings. Optionally or alternatively, such marking is done on an image on a screen, for example, on an image of a preexisting tooth model.

Combining Models

Figure 15:
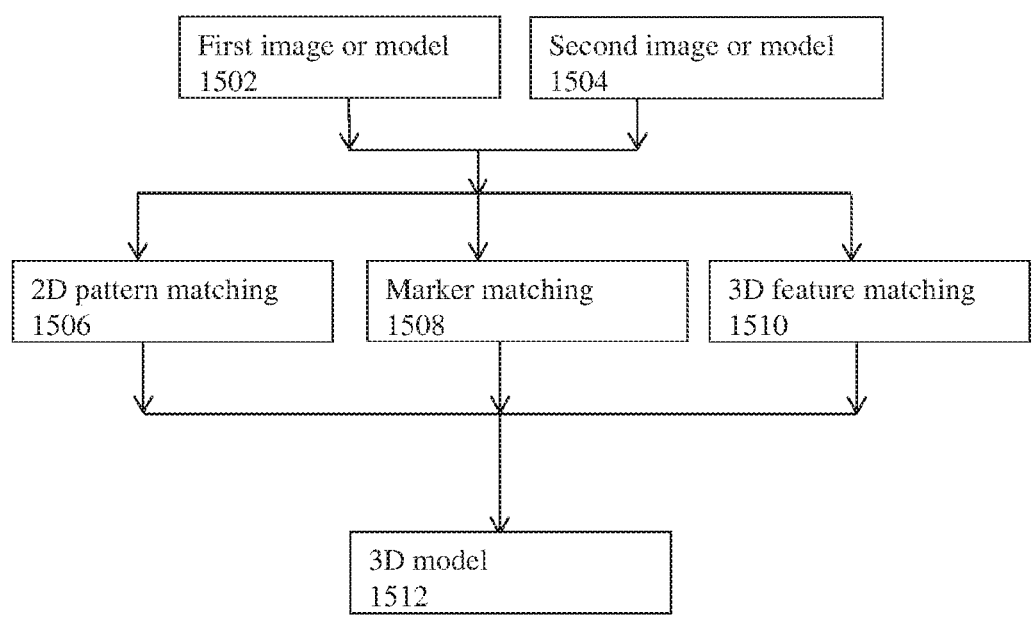
FIG. 15 is a flow chart which shows a method and algorithm for alignment in accordance with an/some exemplary embodiment/s of the invention.

FIG. 15 is flow chart which shows a method for alignment of one or more images and/or one or more models, in accordance with an exemplary embodiment of the invention. In some embodiments images are aligned to provide 3D modeling, for example, to combine multiple stylus measurements with their associated images, the images are aligned (in some embodiments creating a 3D model). In some embodiments, two or more tooth models (e.g. tooth models from different measurement devices) are combined.

FIG. 15 illustrates combining a first image or model 1502 with a second image or model 1504 to generate a 3D model 1512. The models (or images or image and model) 1502 and 1504 are aligned. For example, one or more of 2D pattern matching 1506, marker matching 1508 and 3D feature matching may be used. Other image alignment methods and/or surface model alignment methods and/or image to surface alignment methods may be used as well.

In some embodiments 2D pattern matching is, for example, of marks or patterns or features of a tooth surface. In some embodiments 2D pattern matching is, for example, matching a light pattern illuminated onto a tooth (and/or teeth and/or mouth structure) e.g. by a pattern projector. In some embodiments matching is of a light pattern is by identifying spatial and/or wavelength and/or temporal coding of the light pattern in at least one image and fitting the pattern to a known reference pattern or to light patterns in other images.

In some embodiments 3D matching is, for example, of tooth 3D surface/s (including the prepared tooth and/or other tooth/teeth). In some embodiments marker matching is when marker/s in both image/s and/or model/s are used to combine the image/s and/or model/s. Although described with reference to combining two image/s/model/s in some embodiments the method for alignment described above is used to align more than two image/s and/or model/s (e.g. combining multiple images collected in a tooth scan).

In some embodiments marker/s and/or fiducial/s can be attached (e.g., marked using a marker or attached by adhesive) to the prepared tooth and/or other teeth and/or other mouth structures. In some embodiments the marker/s are used to combine or register a model of the visible part of the tooth, such as the supragingival part of the tooth (e.g. measured by current available intraoral devices, scanned impressions) with the subgingival or invisible part of the tooth (e.g. measured using one or more of the methods or embodiments described in this document).

A potential benefit of combining two models, as described above, is that the SGMP can be simpler and/or smaller and/or enable faster subgingival scanning and/or lower cost since, for example, the imager, in some embodiments, identifies marker/s and does not measure a full model of visible part of the tooth (e.g. using pattern projection and high resolution imaging).

In some embodiments a supragingival model of a prepared tooth including marker/s and optionally of other mouth structures such as adjacent teeth is acquired. The supragingival model is acquired for example by using intraoral scanners available on the market or by making a standard impression and converting it into a digital 3D file. Optionally, the SGMP is used for acquiring images for reconstructing a model of the supra-gingival portions of the tooth as well.

In some embodiments the SGMP is used to scan the subgingival tooth margins and measurement of subgingival points on the tooth, as described above, is with respect to the marker/s. In some embodiments an imager is used for estimating marker/s position with respect to the main body. In some embodiments, for example two cameras or use of a single camera with two or more viewing angles (e.g. a plenoptic camera). In some embodiments a portion of the camera/s field of view, a Region Of Interest (ROI) which includes markers is imaged at a high rate, (e.g. 250 Hz). In some embodiments the location of marker/s in camera/s images are tracked (e.g. by a processing application) and the ROI is updated during scanning so that the ROI includes the marker/s throughout scanning.

In some embodiments the subgingival margin 3D information (subgingival model) is combined or registered with the supragingival tooth (or teeth) model using marker information to provide a subgingival and supragingival tooth model. In principle, to combine two 3D models together, three markers or fiducials are needed. However, a single marker or fiducial on the tooth (or other mouth structure) with at least three features can provide three anchoring points for combining the two 3D models (supragingival and subgingival) together. In some embodiments the marker includes more or fewer than three features. In some embodiments natural feature/s of the tooth are used as one or more markers.

In some embodiments supragingival scanning (e.g. by intraoral scanner, standard impression scanning, CT) is not able to provide marker information in the model (e.g. color contrast markers cannot be measured by many existing intraoral scanners as existing intraoral scanners generally provide 3D measurement without color contrast information), and produces a marker-free supragingival model.

In some embodiments SGMP stylus is scanned over some supragingival tooth portions of prepared tooth and/or neighboring tooth/teeth for example by scanning several lines and/or measuring points across or around the visible tooth e.g. scanning a cross over the prepared tooth. The SGMP then takes subgingival measurements with respect to the marker/s (as described above). The supragingival SGMP measurements (scanned lines or measured points) relative to the marker/s position are used to combine the marker-free supragingival model (e.g., acquired using one or more of intraoral scanner, scanning standard impression, CT and/or MRI) with the subgingival model. In some embodiments measuring (e.g. scanning lines and/or measuring points) on at least one neighboring tooth reduce a rotation error in alignment between the marker-free supragingival and subgingival models.

As can be seen, in some embodiments, scanned points are added to an existing supragingival model. In other embodiments, the collection of scanned points are themselves joined to form a model which may then be aligned with an existing model. In some embodiments, both models are acquired simultaneously.

In some embodiments, a thick marker (e.g. 50 µm or more thick) is attached to the tooth before supragingival scanning when scanning is with a scanner not able to provide marker information in the model. In some embodiments, the thick marker is attached to a coronal part of the prepared tooth, where the accuracy of the scan is lower. The thick marker appears as a 3D feature in the marker-free model which, in some embodiments is used to combine the marker-free supragingival model as described above (e.g. obtained from a device that cannot capture printed marker/s) with the subgingival model (from SGMP measurements). In some embodiments the thick marker/s are removed from the combined supragingival and subgingival model in model post-processing e.g. by processing application (described below). In some embodiments the thick marker is removed and the tooth area previously under the marker is re-scanned providing a partial supragingival model for combining with the supragingival and subgingival models to provide a tooth model which includes the area under the thick marker.

In some embodiments, while the supra-gingival model is a surface model, it may have images registered therewith and/or include image and/or color information. These images may be used for aligning with images acquired by the SGMP during scanning.

Drill Stylus

Optionally, the stylus is a dental drill. In some embodiments images are collected during drilling and/or grinding preparation of the tooth. In some embodiments the drill tip is tracked using methods described above during preparation of the tooth providing the shape of the prepared tooth 204. Optionally, the drill can have color contrast markings, similar to markings 234 (illustrated in FIG. 2A) or other markings more suited to dental drills (e.g. a pattern printed over or in between drill abrasive powder particles). Optionally, the location of preparation margin finish line 108 is not collected when tracking the drill. In some embodiments the preparation finish line is measured using a stylus similar to those described above. In some embodiments, the drill itself when it is not rotating is used as stylus, the drill tip forming stylus tip 222 for measurements of preparation finish line 108. In some embodiments the drill tip or end is replaced with a stylus similar to stylus 218, optionally including stylus markings 234. Other devices and methods described above can be used for drill tracking.

Exemplary Implementations

Figure 13:
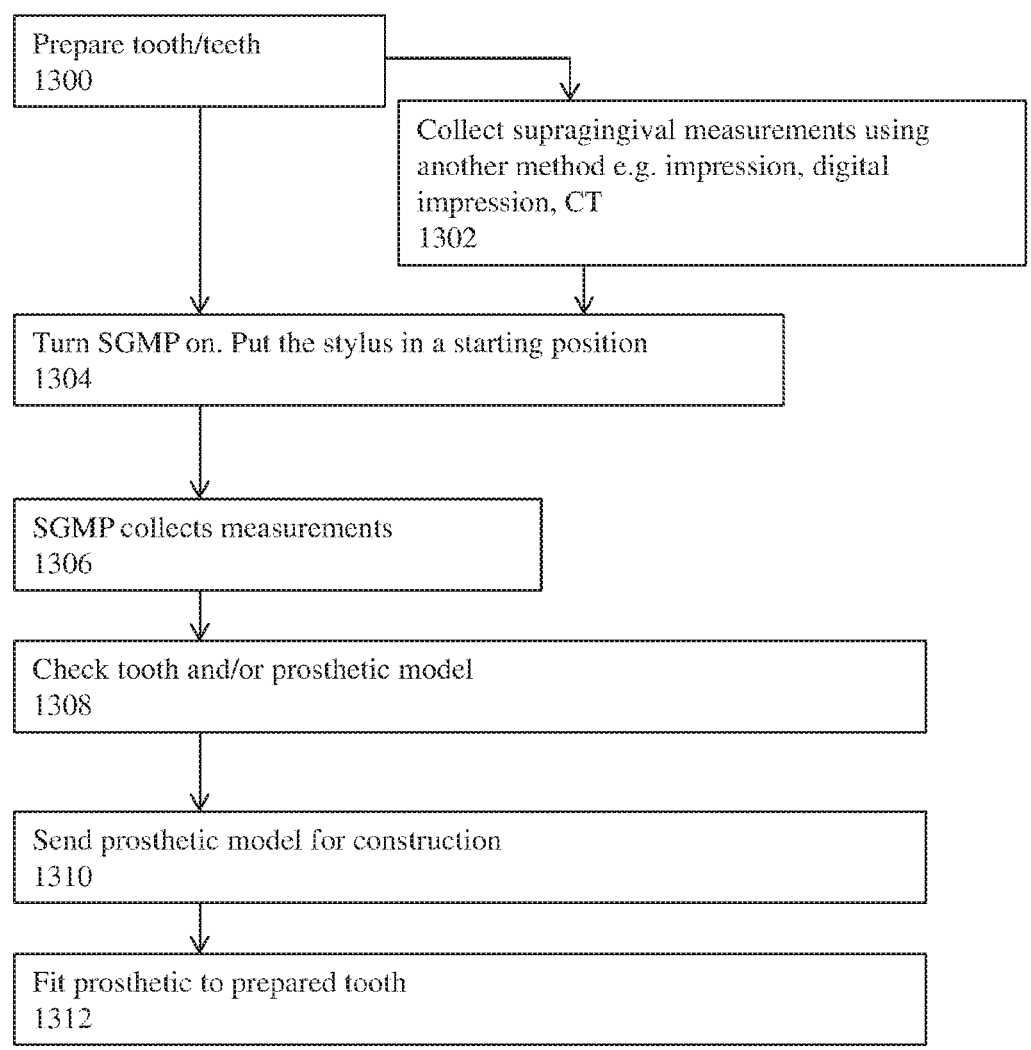
FIG. 13 is a flow chart that illustrates an exemplary method for creation of tailored dental prosthetics in accordance with an/some exemplary embodiment/s of the invention.

FIG. 13 is a flow chart that illustrates an exemplary method for creation of dental prosthetics, in accordance with an exemplary embodiment of the invention. The dentist prepares the tooth or teeth (1300) to which the prosthetic will be affixed. After preparation, optionally, supragingival measurements of the prepared tooth are collected using another device or method, e.g. impression, digital impression, CT, MRI (1302). Optionally a gum receding material (e.g., retraction paste) is applied to the gingiva to cause it to retract away from the tooth. Optionally or alternatively, other materials, such as to reduce bleeding, are used. The SGMP device is then turned on, and the stylus is put into a starting position (1304). SGMP then collects measurements (1306). Measurements can be, for example, optical (e.g. images), mechanical using stylus tracking etc. (e.g., as described above). In some embodiments, for example as described above, collecting measurements involves the user guiding SGMP around the tooth. Optionally, the user can then check the tooth (1308) and/or prosthetic models produced e.g., through a user interface, such a computer with a display and optionally a mouse and/or keyboard. Optionally, the user can manually add a prosthetic finish line to the prosthetic model through the user interface and/or by marking desired prosthetic finish line and/or parts thereof, using the stylus, on the tooth. The user then sends the prosthetic model for construction (1310). Once the prosthetic is received by the user, it is fitted/attached to the prepared tooth (1312). The supra gingival model and sub-gingival model are optionally combined by the user (e.g., using local processing or sending a request to a remote server). Optionally, the user can view the combined model to make sure that the model is correct and optionally modify the combining manually, for example, by rotating, scaling and/or translating a model and/or by defining the process to used for combining overlapping parts of two models. Alternatively, they may be combined by a clinic which manufactures the tooth. Optionally, the combining is at a remote server, which may receive the data from the user, clinic and/or both. Optionally, usage of this remote server is charged.

In some embodiments, the stylus holds a portion of the gingiva away from the tooth at each measuring point around the tooth (as described above). Images are collected of the tooth, including subgingival portions. A model of the tooth (tooth model) can be constructed from the collected images. In an exemplary embodiment of the invention, this can use a device which is otherwise adapted only for supra-gingival imaging. Optionally or alternatively, the device is programmed to recognize the stylus (or other tool, such as a hook, used to retract the gingiva). Optionally, the recognition is used to remove the stylus so that it is not formed into the model. Optionally or alternatively, the recognition is used so that location where sub-gingival portions are visible can be identified (e.g., at the tip of the stylus). Optionally, the device indicates if the entire sub-gingival portion was imaged. In general, it is noted that if a device is made aware of the extent and/or general shape of the sub-gingival areas (e.g., using a CT model or manual entry, such a device (SGMP or other scanner) can automatically detect if sufficiently accurate and/or dense samples are acquired of the areas of interest.

In some embodiments, the stylus holds a portion of the gingiva away from the tooth at each measuring point and the stylus is scanned around the tooth preparation finish line. Estimation of the position of the tip of the stylus with respect to the tooth portions visible to the imager for each point measured around the tooth is used to add a preparation finish line to the tooth model constructed from the collected images. Optionally, the user is prompted to perform such a scan by the user interface (e.g., visible and/or audio display).

Figure 14:
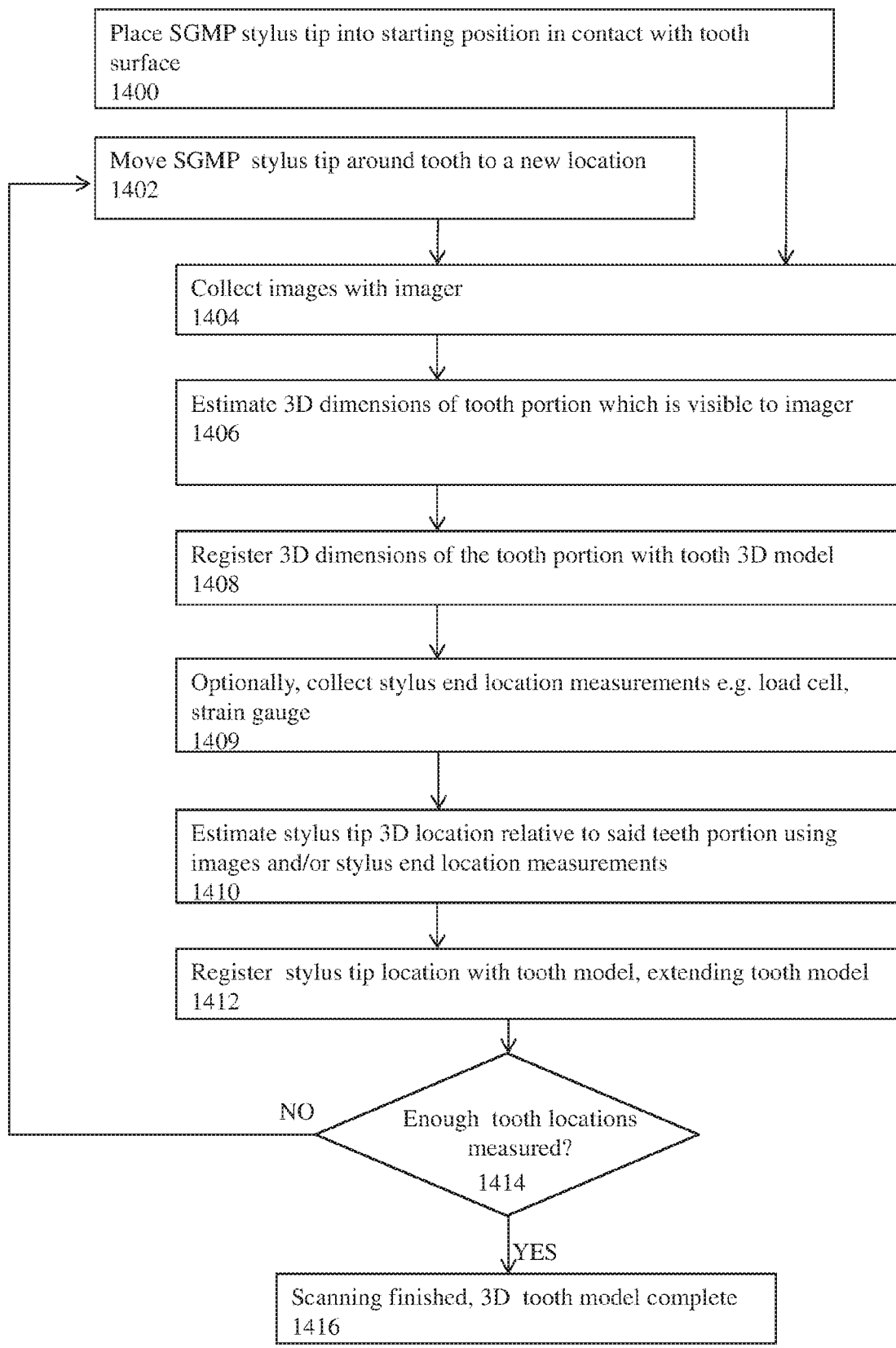
FIG. 14 is a flow chart which shows a method and algorithm for creating a 3D model of a tooth in accordance with an/some exemplary embodiment/s of the invention.

FIG. 14 is a flow chart which shows a method and algorithm for creating a 3D model of a tooth, in accordance with an exemplary embodiment of the invention. The SGMP stylus tip is placed into a starting position in contact with a surface of the tooth 1400. The SGMP then collects images with the imager 1404. From the collected images, the dimensions (surface topography) with respect to the imager of a tooth portion visible (visible tooth portion) to the imager are estimated 1406.

In some embodiments the visible tooth portion is visible to two cameras. In some embodiments the visible tooth portion is a visible to at least one camera and a pattern projector. In some embodiments the visible tooth portion is visible to at least two viewing angles of a plenoptic camera. In some embodiments the visible tooth portion is visible to at least two apertures of a multi-aperture camera. In some embodiments a tooth portion including visible feature/s and/or marker/s is visible to at least one camera.

The estimation of the dimensions of the tooth portion is then registered with a tooth 3D model 1408. Optionally or alternatively, the images are combined into a model, for example, using tooth model building methods known in the art. Optionally, if a part of the model is corrected, the same correction may be applied to the sub-gingival portion whose position was simultaneously acquired. In some embodiments, the subgingival portions are acquired after at least data of a coarse supragingival model is acquired and/or reconstructed.

In some embodiments feature/s and/or marker/s locations are known a priori or feature/s/marker/s location images from other viewing angles enable feature/maker location estimation, the location of feature/s/marker/s are registered with tooth 3D model. In some embodiments, the tooth 3D model is preexisting for example, from another method/device (e.g. traditional impression, digital impression, CT, previous measurements using SGMP). In some embodiments the tooth 3D model is generated by the SGMP during measuring/scanning. Optionally, registration is by matching marker/s which can be physical marker/s on the tooth and/or tooth features that appear in 3D model (3D matching) and/or tooth features that appear in imagers 2D images (2D pattern matching). Optionally, stylus end location (stylus tip location with respect to cameras) measurements are collected using methods described above for example by force sensor (e.g. load cell, strain gauge 1409). The location of the stylus tip with respect to the visible tooth portion (stylus tip location) is then estimated 1410. The stylus tip location is then registered with the tooth 3D model 1412. If enough tooth locations have been measured 1414 scanning is finished and the 3D tooth model is complete 1416. If more tooth locations are to be measured the SGMP stylus tip is moved around the tooth to a new location 1402 where measurements 1404, 1409, estimations 1406, 1410 and registration with tooth 3D model 1408, 1412 are repeated for the new location.

Optionally, the user receives an alarm or other indication when scanning is complete. Optionally, SGMP can indicate to the user to conduct additional scanning and/or areas of the tooth to scan. Optionally, a user display an image of a scanned tooth model with an indication of missing tooth portions or other tooth portions to be scanned.

Optionally, in some embodiments, the method described in FIG. 14 can be repeated, with stylus measurements for more than one tooth whilst registering with a model, to create 3D models of more than one tooth, for example when making measurements for a bridge. Optionally, in some embodiments, the method can include taking stylus measurements for one tooth whilst registering measurements and collecting images of other mouth structures e.g. other teeth, gums.

Optionally, in some embodiments, the user generates a prosthetic finish line and/or a preparation finish line from SGMP stylus tip locations when scanning around the tooth (e.g. the user selects a user interface option to 'define prosthetic finish line' and then scans the stylus tip around a desired prosthetic finish line).

Optionally and alternatively, more than one measurement at a time is registered with the tooth model (e.g. after scanning). Optionally SGMP measurements can be collected before collecting or accessing a 'preexisting' model.

Optionally, after scanning is complete, a processing application uses the gathered images and stylus locations to provide a better accuracy model. This may be useful if, for example, the model is generated incrementally. An optimization process, for example, iteratively applied, can modify parts of the model so that the overall error is reduced. In one example, an optimization algorithms that uses some or all the acquired information (e.g., global optimization or Iterative Closest Point (ICP) algorithm) is used to minimize the difference between clouds of points that are generated by different parts of the scanning process. ICP is optionally used to reconstruct 2D or 3D surfaces from different scans. In an iterative method, the existing model is taken as a starting point and then "corrected" using the acquired data so as to, for example, reduce errors and/or artifacts therein. This process is optionally repeated.

In an exemplary embodiment of the invention, the estimation of tip location is updated when the model is updated and thus the matching of images to the model may also change. Optionally or alternatively, assumptions on the tooth model (e.g., continuity and smoothness) and/or stylus motions are used to define constraints on the model which are minimized by a global (and/or local) optimization method.

System for Producing Dental Prosthetic

Figure 12:
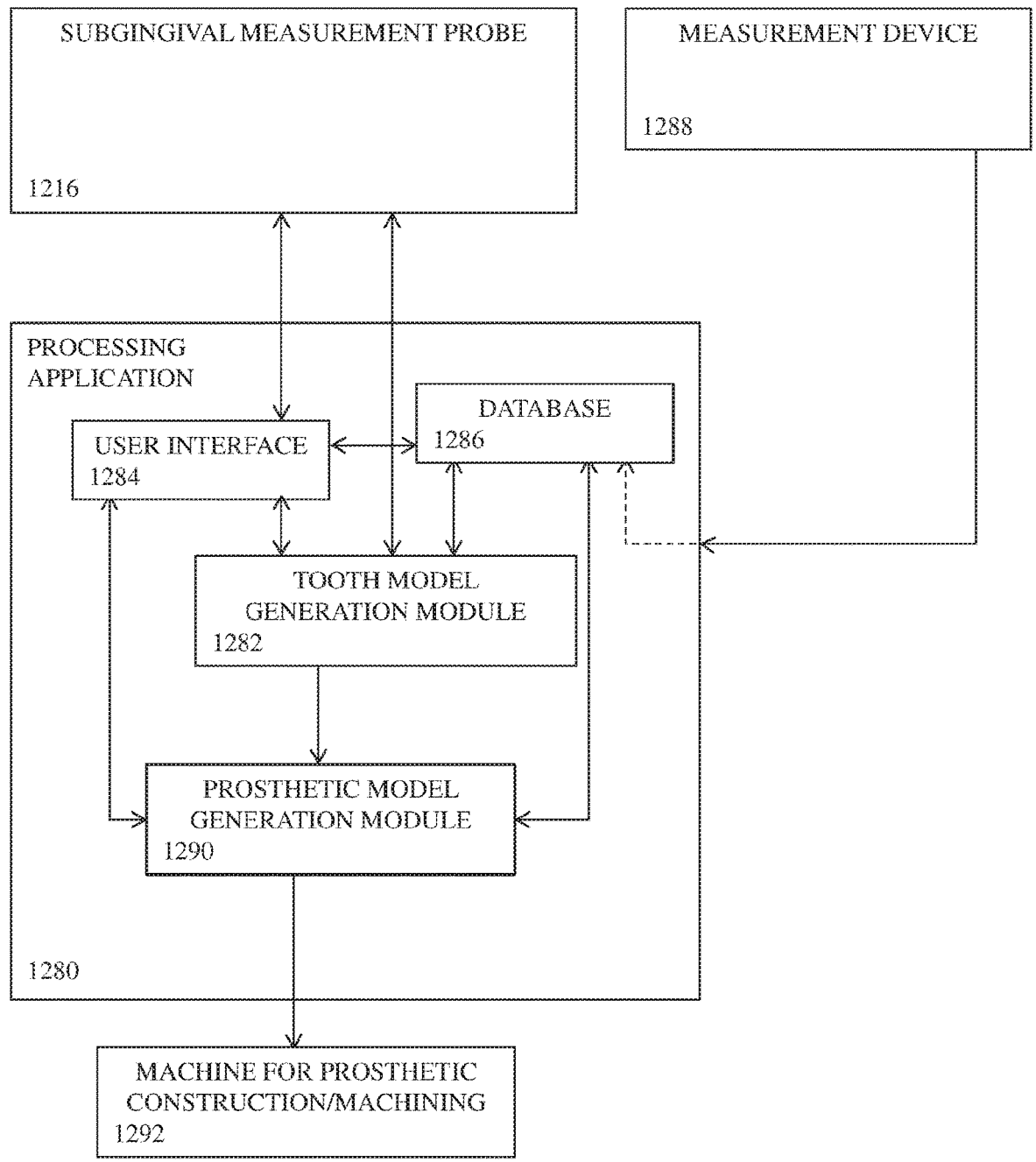
FIG. 12 is a schematic diagram of an embodiment of a system for producing a dental prosthetic in accordance with an/some exemplary embodiment/s of the invention.

Optionally, embodiments of SGMP can be part of a system for producing a fitted dental prosthetic (e.g. crown or bridge). FIG. 12 is a schematic diagram of an embodiment of a system for producing a fitted dental prosthetic. A subgingival margin probe (SGMP) 1216 is connected to a remote processing application 1280. As described above, in some embodiments connection is wireless and in some embodiments connection is by cable. In some embodiments remote processing application 1280 is entirely or partially hosted by a machine in proximity to the user (e.g. machine in dentist's office). In some embodiments remote processing application 1280 is entirely or partially hosted by a remote server. Communication between SGMP 1216 and remote processing application 1280, in some embodiments, is via standard communications techniques. SGMP 1216 collects measurements which can be, for example, optical e.g. images, mechanical, magnetic, and passes the measurements to a tooth model generation module 1282 within processing application 1280. Tooth model generation module 1282 generates a model of the tooth from the collected measurements. In some embodiments the generated tooth model includes subgingival regions of the tooth. Tooth model generation module 1282 can also access information held in a database 1286. Database 1286 can hold previously collected measurements by SGMP and/or previously generated tooth model/s and/or information collected by another measurement device 1288 or devices (e.g. impression, digital impression, CT, MRI, X-ray images). A user, through user interface 1284, can control and/or send instructions to SGMP 1216 and interact with tooth model generation module 1282 and database 1286.

A prosthetic model generation module 1290 constructs a prosthetic model, using information from tooth model generation module 1282 regarding one or more than one tooth and optionally using user instructions from user interface 1284 and optionally using information from database 1286. In one embodiment database 1286 includes a model of the tooth before preparation, which was provided by SGMP scanning or another method. In some embodiments the model of the tooth before preparation is used to construct a prosthetic model which matches the patient's original tooth. In some embodiments user interface 1294 is connected to prosthetic model generation module 1290 so that, for example the user can view the prosthetic before sending it for construction. In some embodiments the user manually indicates a prosthetic finish line: The user, through user interface 1284, indicates the prosthetic finish line on the generated tooth model or on the generated prosthetic model.

Optionally SGMP includes processing application 1280 or SGMP includes an additional processing application. Optionally SGMP includes a user interface. For example, a SGMP processing application and user interface could provide real time feedback regarding measurements and/or generation and display of a basic tooth model guiding the user in measurement collection, leaving processing application details of model generation to processing application 1280.

Optionally, the user evaluates the quality of the tooth preparation, (e.g., to determine if the margin has a proper shape and/or dimensions and/or if a crown or bridge will be strong and/or durable enough) by viewing the tooth model through the user interface, optionally deciding to continue preparation (e.g. drilling) and re-scan.

Optionally, the user evaluates the quality of the measurements by visually checking the tooth model, e.g. through the user interface.

Optionally, the processing application evaluates the quality of the measurements or the scan, for example by checking that a preparation finish line is detected (e.g. by evaluating tooth surface slope and finding a preparation margin step feature). In one embodiment the processing application, through the user interface, indicates that a portion or portions/s of the tooth should be rescanned. It should be appreciated that multiple processing models may be provided, for example, at a dentist office, at a prosthesis manufacture clinic and/or at a remote server. Each such application may provide only some or all of the functionalities described herein, for example, as modules. In an exemplary embodiment of the invention, one or more of the following modules are provided: image to model registration module, stylus tip locating module, image depth extraction module, marking analysis module, self-calibration module, moving stylus tracking module, sensor processing module, model combining module, model registering module, image-image combining module, supra-gingival model creating module and/or subgingival model creating module. The functionality of one or more of the modules may be, for example, as described herein. Optionally, the modules are provided in transitory and/or non-transitory storage (e.g., flash memory and/or mechanical hard disk).

In some embodiments the SGMP and processing application produce a tooth model which is physically constructed (e.g., by 3D printing and/or milling) and the physical model is used, as is known in the art of traditional and/or digital impression, for construction of a prosthetic.

It is noted that, optionally, the sub-gingival model is added to a supra-gingival model, after the supra-gingival model is acquired by scanning (or otherwise imaging) a cast of the patient's tooth.

Exemplary Calibration Details

In an exemplary embodiment of the invention, the SGMP imager is calibrated to relate a point or feature seen by at least one camera to its 3D location in relation to imager or imager final optical element. Such calibration may use methods known in the art of image calibration.

The calibration may include at least one imager camera "intra" parameter (e.g. focal length, center offset, lens distortion, CMOS pixels scaling and/or skew factors) and "inter" parameters that relates cameras to each other (e.g. relative position, orientation, rotation and/or, offset), the latter case being relevant to stereophotogrammetry configurations whether passive or active. In the active case the calibration optionally includes at least one pattern projector "intra" parameters (e.g. pattern, focal length, center offset, lens distortion, scaling, skew factors) and/or "inter" parameters that relates said at least one projector to one or more cameras (e.g. relative position, orientation, rotation and/or, offset).

The calibration can be done, for example, at the factory and/or using or by a known target. One example is a standard checkerboard pattern with given square size upon a plane: The distinguishable squares' cross points are detected and compared between the reference and resultant image. The reference image can be a theoretical pattern in case of a single camera calibration or an image acquired by a different camera.

The deviation between the resultant grid vs the reference one may be formulated into a calibration parameters equation system and solved for parameters extraction. Optionally, scaling is also provided by imaging an element (e.g. a stylus marking) of a known scale.

If the SGMP is dropped or suffers other mechanical shock and/or thermal variations, calibration may be repeated, for example, as the geometric relationship between camera(s) and/or projector(s) can be changed thereby. Optionally, such calibration is provided with a user interface for use by a dentist.

Other Applications—

In some embodiments, the above described methods and device are used for measurement in additional dental procedures, such as 3D scanning of preparation for inlays, onlays, and fillings. In some embodiments the above described methods and device are used to measure implant connections and implant abutments including one or more of the implant neck, hexagon, and outer surface connected to the abutment. Once measured, a model may be displayed to a user and/or an existing model updated. For example, a measurement of nearby teeth may be used to show the orientation and/or position of an implant relative to other teeth and/or a jaw and/or a CT data set.

In some embodiments the methods and device are used to measure sulcus or pocket depth. The sulcus or pocket depth is the distance between the free gingival line (or gum line) and the sulcus or pocket bottom. The sulcus depth is a common measure used in evaluating periodontal disease or other pathological conditions. Pocket depth can be tracked over time in order to evaluate the effect of a dental treatment. In some embodiments SGMP is used to measure sulcus or pocket depth by applying a constant insertion force while inserting the stylus into the sulcus or pocket, similar to measurements taken using a periodontal probe. In some embodiments the device measures the applied insertion force (e.g. using load cell 854 and/or by using force sensor 923) verifying that the applied insertion force is within a valid range. In some embodiments device and method described in this document are used to measure other common dental or periodontal markers, such as Clinical Attachment Level (CAL).

Another use for the device is the marking of areas with certain interests on the teeth and the gum, such that the dentist can touch or scan features on teeth or in the mouse to mark them on tooth or teeth model, by a special indication. Such features can be, for example, features that should be marked for other dentists or technicians or users for further treatment. Some examples include the boundary between the artificial part of the prepared tooth (filling or build-up) and the organic part of the tooth (Dentine or Enamel), which in many cases cannot be seen in the intraoral scanners 3D models.

Another example is marking an area of the new gum line that the dentist would like to create via surgery. This procedure may be of interest for esthetic reasons to design and demonstrate the result to the patient or other dentists. In this example, the system measures a contact with the gum relative to the tooth peg, but display may be, for example, overlaid on a 3D model showing the tooth with the crown.

Another example is collecting marks and/or data with the device on tooth or teeth or mouth cavity model for transfer to a third party, for example, other attending dentists and technicians and/or oral surgeons, for example, for further treatment and/or consultation-.

Optionally, the data collected is presented to the patient to enhanced information about the treatment and provide visual explanation of the outcome of the treatment. This usage may enhance patient approval and acceptance of the treatment and increase patient satisfaction.

Exemplary Implementations

Figure 16:
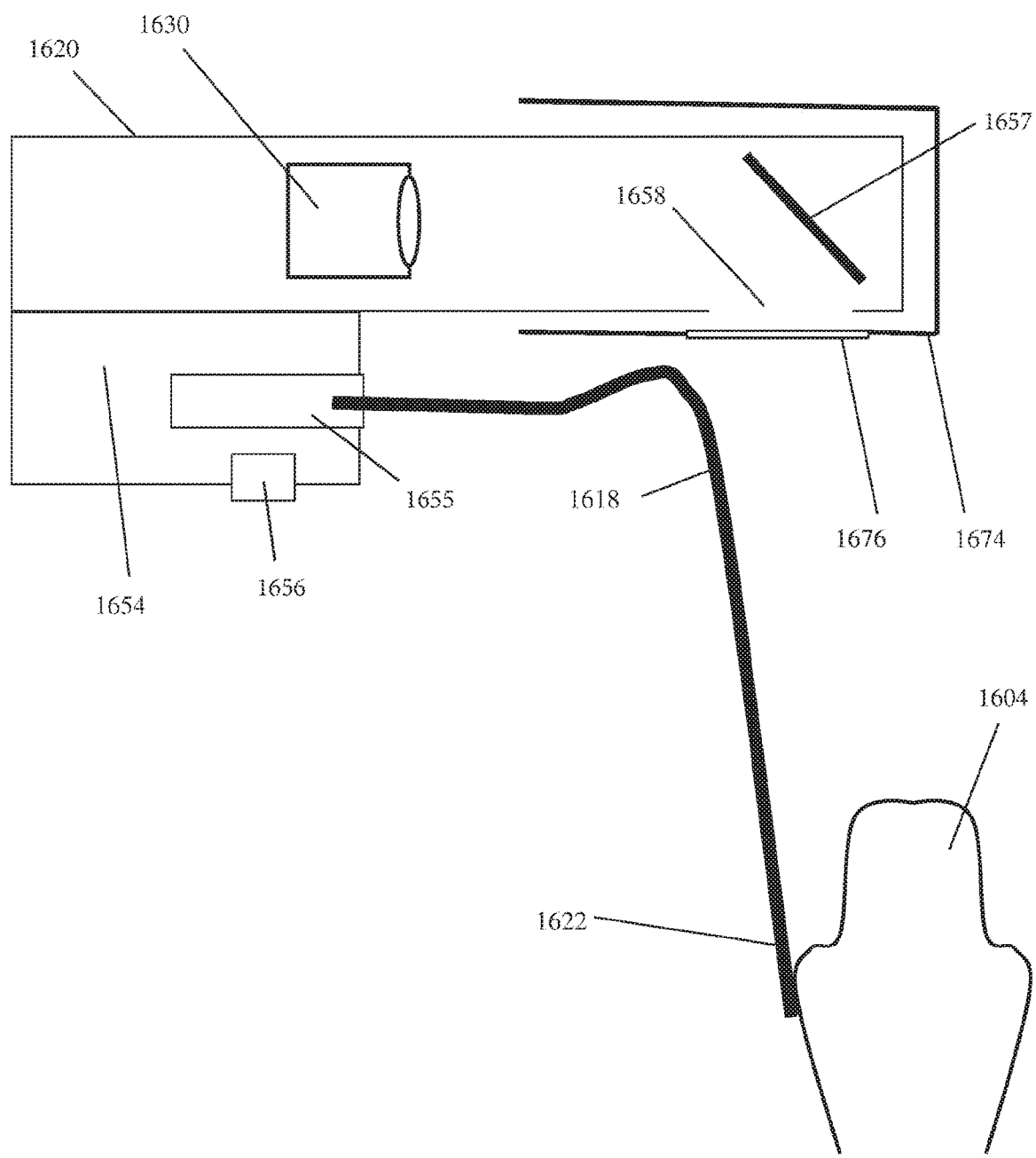
FIG. 16 is a schematic diagram of an embodiment with a side attached angled stylus in accordance with an/some exemplary embodiment/s of the invention.

FIG. 16 is a schematic diagram of a side attached angled stylus. FIG. 16 shows an exemplary stylus shape where stylus 1618 contacts prepared tooth 1604 at a stylus tilt angle which is not 90°. Stylus 1618 is attached to main body 1620 at the side through housing 1654. SGMP also includes a cover 1674 including a transparent window 1676, a mirror 1657 (final optical element).

In some embodiments SGMP includes an adaptor which attaches to an imager. In some embodiments the adaptor includes a stylus, a cover, and a connector for attaching the adaptor to the imager. In some embodiments attachment of the adaptor to the imager is rigid, for example, being a snap or thread attachment. In some embodiments the adaptor connection to the imager allows the adaptor some freedom of movement causing movement of the stylus with respect to the imager. In some embodiments the movement of the stylus with respect to the imager can be compensated for by optical tracking. In some embodiments the adaptor is used with an existing intraoral scanner. In some embodiments the adaptor is a standard cover for existing intraoral scanner to which a stylus has been attached. In some embodiments the imager sits inside the adaptor. In some embodiments the adaptor is side attached to the imager and includes an angled mirror to provide the imager with views of the stylus, and stylus tip. In an exemplary embodiment of the invention, however, the cover is made rigid enough to avoid unwanted movements of the stylus.

In an exemplary embodiment of the invention, a dentist can purchase a set of covers or covers with integral styluses or styluses (e.g., depending on the implementation). For example, a kit including 10, 15, 40 or 100 (or intermediate or greater numbers) of covers, styluses and/or integrated covers with styluses may be provided.

In some embodiments, housing 1654 connecting between main body 1620 and stylus 1622 includes a mechanism to measure stylus movements and/or deflection and estimate tip location, for example, such as described before. In some embodiments housing 1654 connecting between main body 1620 and stylus 1622 includes a mechanism to move stylus 1622 and measure tip location, for example, such as described before. In some embodiments housing 1654 is connected to electronic unit that provides power and read data from housing 1954. In some embodiments housing 1654

Figure 17:
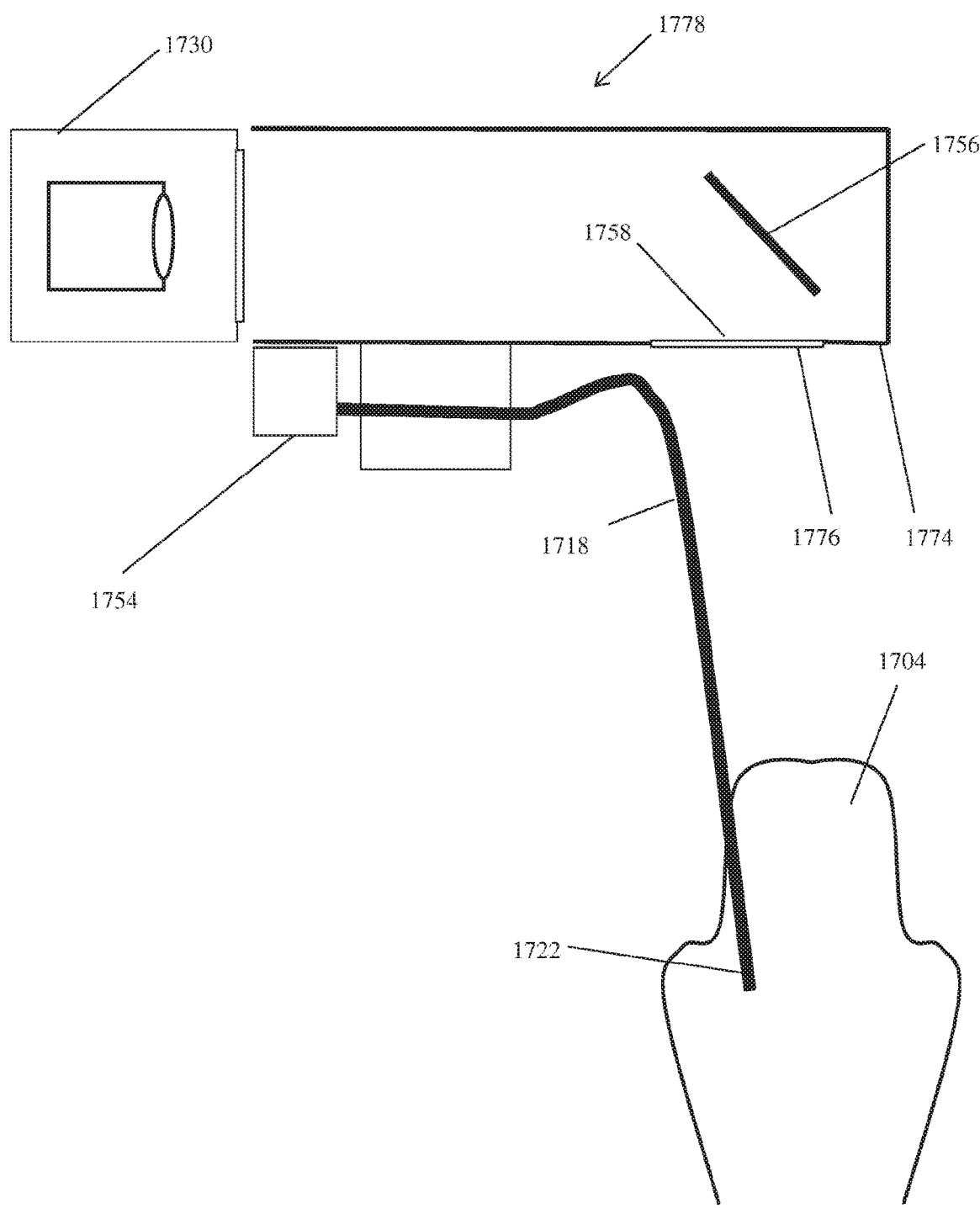
FIG. 17 is a schematic diagram of an adaptor which side attaches to an imager in accordance with an/some exemplary embodiment/s of the invention.

FIG. 17 is a schematic diagram of an adaptor including a mirror side which attaches to an imager. An adaptor 1778 includes a stylus 1718 attached to a cover 1774 through housing 1754. In some embodiments, housing 1754 includes actuator/s, and/or sensor/s (e.g., load sensor) as described previously. Cover 1774 includes a mirror 1756, a transparent window 1776 over an entrance aperture 1758. Cover 1774 attaches to an imager 1730.

Figure 18:
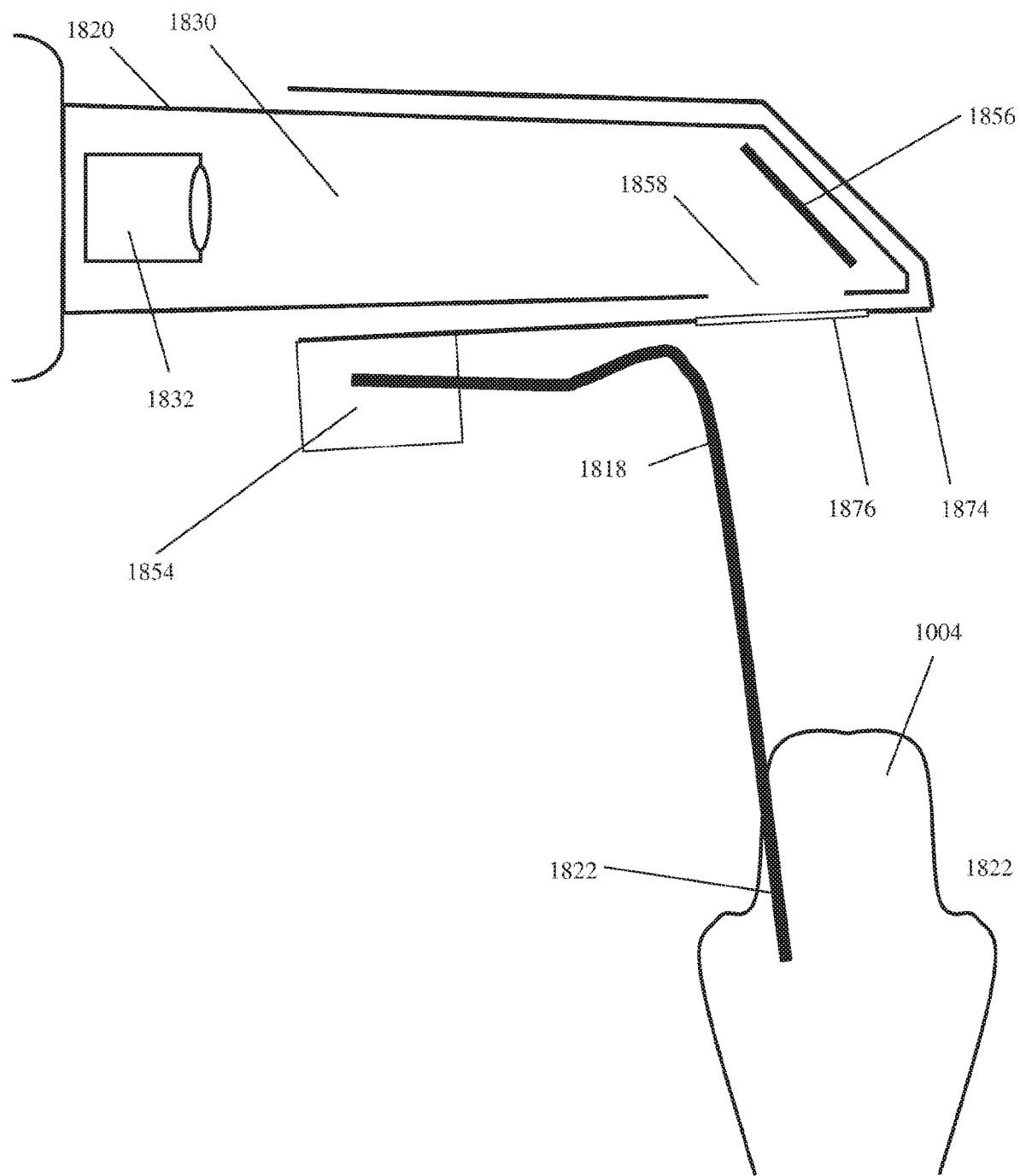
FIG. 18 is a schematic diagram of an adaptor which covers a part of an imager including a mirror in accordance with an/some exemplary embodiment/s of the invention

FIG. 18 is a schematic diagram of an adaptor which covers a part of an imager including an optional mirror, according to an exemplary embodiment of the invention. As shown, FIG. 18 schematically illustrates a SGMP with a stylus attached to an imager 1820 through an adaptor shaped as a cover 1874. The adaptor includes a stylus 1818, a housing 1854, and a cover transparent portion 1876. Imager 1830 includes an imager main body 1820, one or more camera 1832 and optionally a mirror 1856. Cover 1878 covers a portion of an imager main body 1820. Housing 1854 connects stylus 1818 to cover 1874.

In some embodiments stylus 1822 is rigidly connected to cover 1874 through housing 1854. Optionally, cover 1874 can be secured rigidly to imager 1820 with mechanical pressure applied by attachment mechanism and can optionally be released by pressing a release button.

In some embodiments housing 1854 connecting between cover 1874 and stylus 1822 includes a mechanism to measure stylus movements and/or deflection and estimate tip location, for example, such as described before. In some embodiments housing 1854 connecting between cover 1874 and stylus 1822 includes a mechanism to move stylus 1822 and measure tip location, for example, such as described before. In some embodiments housing 1854 is connected by wires (not shown in FIG. 18) to electronic unit that provides power and read data from housing 1854. In some embodiments housing 1854 is connected wirelessly to electronic unit and includes a power source that provides power to housing 1854. In some embodiments housing 1854 is also electronically connected to imager 1820 through an electric contacts between cover 1874 and imager 1820 (not shown in FIG. 18) to provide power and/or read data from housing 1854. In some embodiments, housing 1854 provides only mechanical connection between stylus 1922 and cover 1874 stylus tip location is measured through imager, for example, as described before. In some embodiments housing 1854 includes a connector for connecting stylus 1822 to cover 1874 through housing 1854. In some embodiments stylus 1822 is disposable. In some embodiments cover 1874 and stylus 1822 are a single disposable unit.

Figure 19:
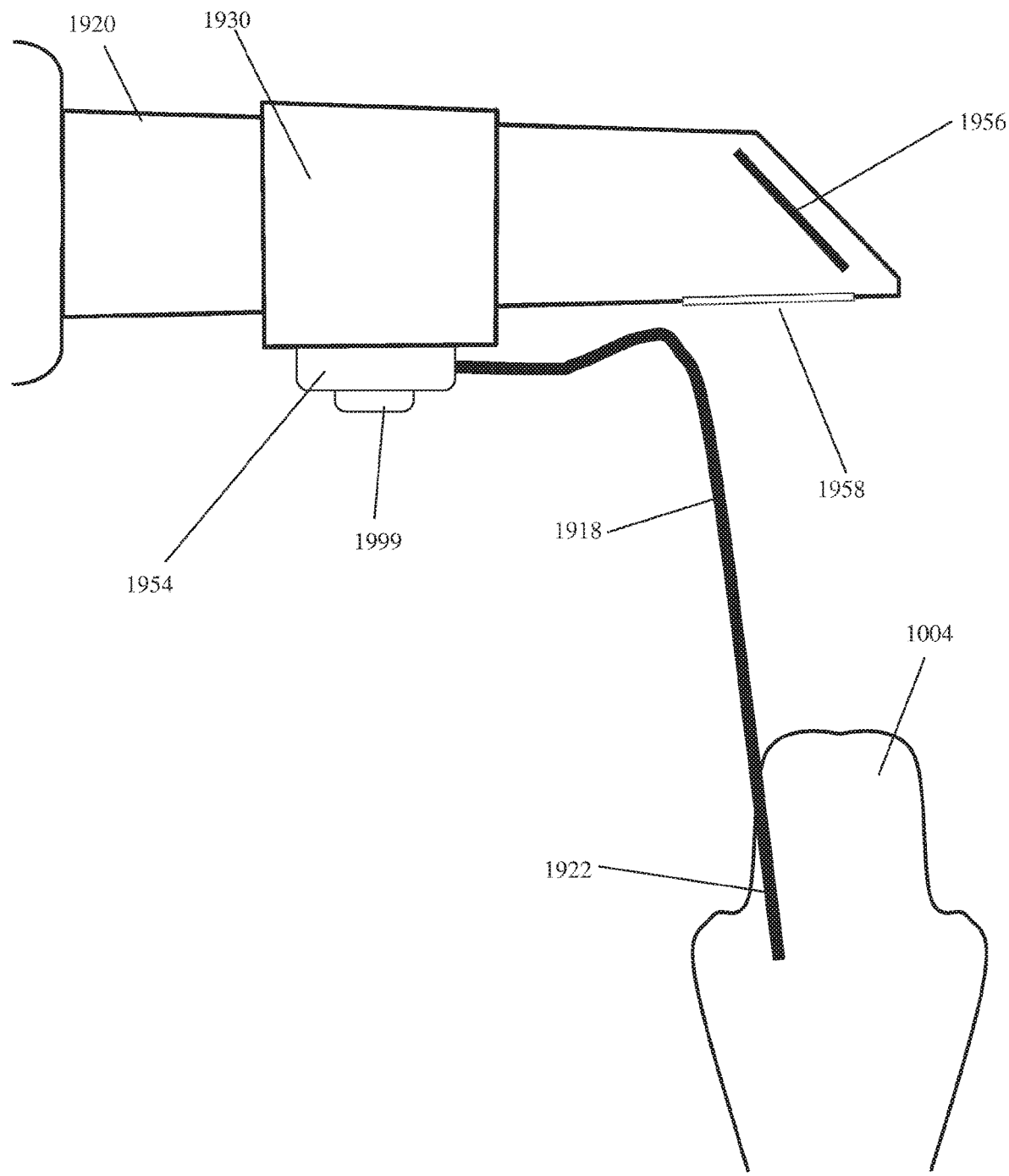
FIG. 19 is a schematic diagram of an adaptor including a sensor in accordance with an/some exemplary embodiment/s of the invention.

FIG. 19 is a schematic diagram of a SGMP with a stylus attached to imager 1920 with by adaptor 1930, in accordance with an exemplary embodiment of the invention. Optionally, stylus 1922 is rigidly connected to adaptor 1930. In some embodiments adaptor 1930 can be secured rigidly to imager 1920 with mechanical pressure applied by an attachment mechanism and/or can optionally be released by pressing release button 1918. In an exemplary embodiment of the invention, imager 1920 includes a window 1958 and may include a mirror 1956, for example as shown in FIG. 19, or other optical elements.

In some embodiments housing 1954 connecting between adaptor 1930 and stylus 1922 includes a mechanism to measure stylus movements and/or deflection and estimate tip location, for example, such as described before. In some embodiments housing 1954 connecting between adaptor 1930 and stylus 1922 includes a mechanism to move stylus 1922 and measure tip location, for example, such as described before. In some embodiments housing 1954 is connected by wires (not shown at FIG. 19) to electronic unit that provides power and read data from housing 1954. In some embodiments housing 1954 is connected wirelessly to electronic unit and includes a power source that provides power to housing 1954. In some embodiments housing 1954 is also electronically connected to imager 1920 through an electric contacts between adaptor 1930 and imager 1920 (not shown at FIG. 19) to provide power and/or read data from housing 1954. In some embodiments housing 1954 provides only mechanical connection between stylus 1922 and adaptor 1930 and stylus tip location is measured through imager, for example, as described before. In some embodiments housing 1954 includes a connector for connecting stylus 1922 to adaptor 1930 through housing 1954. In some embodiments stylus 1922 is disposable. In some embodiments adaptor 1930 and stylus 1922 are a single disposable unit.

In some embodiments imager 1820 and/or 1920 is an independent 3D intraoral scanner, for example, a commercially available intraoral scanner. In some embodiments the software of intraoral scanner is modified to include components for detection of stylus location from imager and combine it with tooth model. Optionally or alternatively, the software of intraoral scanner is modified to include components for removing stylus image from images used for creation of the tooth model. In some embodiments the software of intraoral scanner is modified to include components that use information from additional sensors for estimating tip location and/or combine that information for obtaining a tooth model.

In some embodiments attachment of the cover 1874 and/or adaptor 1930 to the imager 1820 is rigid. In some embodiments the adaptor connection to the imager allows the adaptor some freedom of movement allowing movement of the stylus with respect to the imager. In some embodiments the movement of the stylus with respect to the imager is compensated for by measurement using optical tracking and correction. In some embodiments an imager sits inside the adaptor.

As used herein the term "about" refers to ±20%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. An intra-oral scanner system comprising:
   a. an intra-oral scanner (IOS) comprising:
      i. a structured light projector; and
      ii. at least one image sensor, said image sensor defining a line of sight of the image sensor in said IOS;
   b. an adaptor comprising:
      iii. a connector configured to connect said adaptor to said IOS; and
      iv. an elongate probe coupled to said adaptor, comprising:
         A. a probe body; and
         B. an elongate section which:
            extends away from said probe body,
            upon connecting said adaptor to said IOS, extends away from said line of sight of said imager; and
            includes a tip sized and shaped to be inserted between a tooth and adjacent gingiva,
   wherein:
      said adaptor is configured so that, upon connecting said adaptor to said IOS:
         v. a long axis of said elongate section extends at an angle of 45-90° from said line of sight of said image sensor; and
         vi. at least a portion of said elongate section is illuminated by structured light of said structured light projector and viewable within a field of view (FOV) of said image sensor;
      wherein upon connecting said adaptor to said IOS, said FOV is substantially perpendicular to said line of sight of the image sensor in said IOS.

2. The system according to claim 1, wherein said connector is configured to mount on at least a portion of said IOS.

3. The system according to claim 2, wherein said adaptor, when mounted onto said IOS, extends over at least a portion of said IOS.

4. The system according to claim 1, wherein said adaptor further comprises at least one sealed transparent window aligned with the FOV of said image sensor.

5. The system according to claim 1, wherein said connector rigidly couples said adaptor to said IOS.

6. The system according to claim 5, wherein said rigid coupling allows a tip of said elongate to move, with respect to said IOS, by 10 μm-2 mm during scanning.

7. The system according to claim 1, wherein once coupled, said adaptor and said probe are configured with freedom of movement with respect to said IOS.

8. The system according to claim 1, wherein said adaptor further comprises at least one force sensor coupled to said probe.

9. The system according to claim 8, wherein said force sensor is configured to measure movement of said probe.

10. The system according to claim 8, wherein said force sensor is configured to measure deflection of said probe.

11. The system according to claim 1, wherein said adaptor further comprises at least one actuator configured to automatically move said probe.

12. The system according to claim 1, wherein said adaptor further comprises a power and/or data contact that connects said adaptor with a respective power and/or data contact on said IOS.

13. The system according to claim 1, wherein said probe includes at least one marking.

14. The system according to claim 13, wherein said marking is selected from the group consisting of: a contrast color, a sphere, a mirror, a marking illuminated from within said probe, a window or beam shaping elements in said probe.

15. The system according to claim 13, wherein said marking comprises at least one specular sphere arranged on the outer surface of said probe and is illuminated from within said probe.

16. The system according to claim 1, wherein said elongate section includes said probe tip, where said probe tip is configured to move with respect to said probe body.

17. The system according to claim 1, wherein said tip of said probe is sized for insertion between a tooth and an adjacent gingiva at a distance between said tip and said adaptor such that said adaptor fits inside an adult human mouth.

18. The system according to claim 1, further comprising at least one mirror for directing light from said FOV.

19. The system according to claim 18, wherein said elongate section of said probe is viewable within said FOV via said mirror.

20. The system according to claim 1, wherein said probe is configured for detachment from said adaptor.

21. The system according to claim 20, wherein said probe comprises a material configured for processing in an autoclave.

22. The system according to claim 20, wherein said probe is disposable.

23. The system according to claim 1, wherein said adaptor is disposable.

24. The system according to claim 1, wherein said adaptor is configured so that said elongate section of said probe extends approximately 90° to a long axis of said adaptor.

25. The system according to claim 1, wherein a distance between a tip of said probe and said adaptor is configured to fit inside an adult human mouth.

26. The system according to claim 1, wherein said adaptor is configured so that a distance between a tip of said probe and a final optical element of said image sensor is less than 4 centimeters.

27. The system according to claim 1, wherein said adaptor comprises a mirror configured for re-directing said image sensor to include a field of view (FOV) centered around 45-90° to a line of sight of said image sensor in said IOS.

28. The system according to claim 1, wherein said probe comprises at least one fiducial which is visible within said FOV of said image sensor and is illuminated by structured light of said structured light projector.

29. The system according to claim 1, wherein said image sensor of said IOS comprises a final optical element located at a distal end of said IOS; and
wherein said connector includes a housing sized and shaped to fit over said distal end of said IOS, where upon connecting said adaptor to said a portion of said housing is positioned proximal of said final optical element.

30. A method for intra-oral scanning of at least a portion of a tooth using the intra-oral scanner system according to claim 1, comprising:
mounting the adaptor on the intra-oral scanner (IOS), the IOS having at least one image sensor with a field of view (FOV) of at least a portion of a tooth;
acquiring at least one image of a least a portion of said tooth and at least a portion of said probe; and
estimating a location of said tip with respect to said tooth based on said image.

31. The method according to claim 30, wherein the at least one image sensor comprises a plurality of image sensors, said acquiring at least one image comprises acquiring a plurality of images from said plurality of image sensors, and said estimating said location of said tip with respect to said tooth is based on said images.

32. The method according to claim 31, further comprising combining location information, and producing a tooth model based on said combined location information.

33. The method according to claim 32, wherein once coupled, said adaptor and said probe are configured with freedom of movement with respect to said IOS, and wherein the method further comprises at least one of optically tracking said movement and correcting said model based on said tracking.

34. The method according to claim 31, wherein at least one of said tooth images includes at least one subgingival surface portion.

35. The method according to claim 30, wherein said mounting further comprises at least one of applying mechanical pressure and rigidly securing said adaptor to said IOS.

36. The method according to claim 30, wherein said adaptor further comprises a release button or trigger configured to release said adaptor from said IOS when pressed or triggered, respectively.

37. The method according to claim 30, wherein said adaptor further comprises a release button or trigger configured to release said probe from said adaptor when pressed or triggered, respectively.

38. An intra-oral scanner system, comprising:
a. an intra-oral scanner (IOS), comprising:
i. at least one image sensor, said image sensor comprises a final optical element located at a distal end of said IOS, said image sensor defining a line of sight of the image sensor in said IOS,
b. an adaptor comprising:
ii. a connector configured to connect said adaptor to said IOS and including a housing sized and shaped to fit over said distal end of said IOS, where upon connecting said adaptor to said IOS, a portion of said housing is positioned proximal of said final optical element; and
iii. an elongate probe coupled to said adaptor, comprising:
A. a probe body; and
B. an elongate section which:
extends away from said probe body,
upon connecting said adaptor to said IOS, extends away from said line of sight of said imager; and
includes a tip sized and shaped to be inserted between a tooth and adjacent gingiva,
wherein:
said adaptor is configured so that, upon connecting said adaptor to said IOS:
iv. a long axis of said elongate section extends at an angle of 45-90° from said line of sight of said image sensor; and
v. at least a portion of said elongate section is viewable within a field of view (FOV) of said image sensor;
wherein upon connecting said adaptor to said IOS, said FOV is substantially perpendicular to said line of sight of the image sensor in said IOS.

* * * * *